(12) United States Patent
Schall et al.

(10) Patent No.: US 7,025,968 B2
(45) Date of Patent: Apr. 11, 2006

(54) CMV VACCINES

(75) Inventors: Thomas J. Schall, Meno Park, CA (US); Mark E. T. Penfold, Mountain View, CA (US)

(73) Assignee: ChemoCentryx, Inc., San Carlos, CA (US)

(*) Notice: Subject to any disclaimer, the term of this patent is extended or adjusted under 35 U.S.C. 154(b) by 240 days.

(21) Appl. No.: 09/944,049

(22) Filed: Aug. 30, 2001

(65) Prior Publication Data

US 2003/0175681 A1 Sep. 18, 2003

Related U.S. Application Data

(60) Provisional application No. 60/229,365, filed on Aug. 30, 2000.

(51) Int. Cl.
*A61K 39/245* (2006.01)
*C12N 7/04* (2006.01)

(52) U.S. Cl. ............................. 424/205.1; 424/230.1; 435/235.1; 435/236

(58) Field of Classification Search ............... 424/205.1, 424/230.1; 435/235.1, 236
See application file for complete search history.

(56) References Cited

U.S. PATENT DOCUMENTS

| | | | |
|---|---|---|---|
| 3,379,729 A | 4/1968 | Protiva et al. | |
| 4,243,805 A | 1/1981 | Protiva et al. | |
| 5,529,771 A | 6/1996 | Hooks et al. | |
| 5,652,133 A | 7/1997 | Murphy | |
| 5,665,362 A | 9/1997 | Inglis et al. | |
| 5,720,957 A | 2/1998 | Jones et al. | |
| 5,753,476 A | 5/1998 | Jones et al. | |
| 5,756,264 A | 5/1998 | Schwartz et al. | |
| 5,763,217 A | 6/1998 | Cynader et al. | |
| 5,824,318 A | 10/1998 | Mohr et al. | |
| 5,843,458 A | 12/1998 | Jones | |
| 5,846,806 A | 12/1998 | Jones et al. | |
| 5,866,136 A | 2/1999 | Ramshaw et al. | |
| 5,877,004 A * | 3/1999 | Jones et al. ............... | 435/235.1 |
| 5,908,780 A | 6/1999 | Jones | |
| 5,939,320 A | 8/1999 | Littman et al. | |
| 5,948,775 A | 9/1999 | Koko et al. | |
| 5,965,697 A | 10/1999 | Czaplewski et al. | |
| 5,998,160 A | 12/1999 | Berens | |
| 6,028,169 A | 2/2000 | Kreider et al. | |
| 6,031,080 A | 2/2000 | Williams et al. | |
| 6,034,102 A | 3/2000 | Aiello | |
| 6,051,375 A | 4/2000 | Rose et al. | |
| 6,051,428 A | 4/2000 | Fong et al. | |
| 6,150,132 A | 11/2000 | Wells et al. | |
| 6,420,121 B1 | 7/2002 | Nelson et al. | |
| 2002/0127544 A1 | 9/2002 | Schall et al. | |

FOREIGN PATENT DOCUMENTS

EP        0 277 773 A1    8/1988
WO        WO 94/11504 A1  5/1994
WO        WO 96/23068 A1  8/1996
WO        WO 98/02151 A2  1/1998
WO        WO 98/11073 A1  3/1998
WO        WO 99/00510 A1  1/1999
WO        WO 99/09178 A1  2/1999
WO        WO 99/27122 A1  6/1999
WO        WO 99/36562 A1  7/1999
WO        WO 99/36568 A2  7/1999
WO        WO 99/61472 A1  12/1999
WO        WO 00/00491 A1  1/2000
WO        WO 00/06203 A1  2/2000
WO        WO 00/11950 A1  3/2000
WO        WO 00/34494 A1  6/2000
WO        WO 02/17900 A2  3/2002
WO        WO 02/17969 A2  3/2002
WO        WO 02/18954 A2  3/2002
WO        WO 02/062296 A2 8/2002

OTHER PUBLICATIONS

Krause et al (Infectious Disease Clinics of North America 13(1):61–81, Mar. 1999).*
Beisser et al (Journal of Virology 72(3):2352–2363, 1998).*
Beisser et al (Journal of Virology 73(9):7218–7230, 1999).*
Hwang et al (Microbiology and Immunology 43(3):307–310, 1999).*
Kropff et al (Journal of General Virology 78:2009–2013, 1997).*
Kravitsz et al (Journal of General Virology 78:1999–2007, 1997).*
Beers, M. et al. *The Merck Manual of Diagnosis and Therapy*, 17th Ed., 1999, pp. 1294–1296, Published by Merck Research Laboratories.
Hardman, J. et al. Goodman & Gilman's The Pharmacological Basis of Therapeutics, 9th Ed., 1996, p. 51, 57–58, McGraw–Hill, printed in the U.S.A.
Horuk, R. "Molecular properties of the chemokine receptor family", *Trends Pharm. Sci.*, vol. 15, (1994), pp. 159–165.
Schall, T.J. et al., "Chemokines, leukocyte trafficking, and inflammation", Curr. Opin. Immunol., vol. 6, (1994), pp. 865–873.
Sindelar, K et al. "Neurotropic and psychotropic agents", Res. Inst. Pharm. Biochem., 1976, pp. 910–922, vol. 41, No. 3, *Abstract only*.
Zlotnik et al. "Recent Advances in Chemokines and Chemokine Receptors" Critical Reviews in Immunology, 1999, pp. 1–47, vol. 19.
Branch, Andrea D.; A good antisense molecule is hard to find; *TIBS 23*; Feb. 1998; pp. 45–50.

(Continued)

*Primary Examiner*—Mary E. Mosher
(74) *Attorney, Agent, or Firm*—Townsend and Townsend and Crew LLP

(57) ABSTRACT

The invention provides methods and compositions for inhibiting CMV infection and dissemination in an animal, as well as in vitro and in vivo assay systems for identifying such compositions.

34 Claims, 11 Drawing Sheets

OTHER PUBLICATIONS

Crooke, Stanley T. et al.; *Antisense Research and Applications; Basic Principles of Antisense Therapeutics*; chapters 1–3; pp. 1–53.

Crystal, Ronald G.; Transfer of Genes to Humans: Early Lessons and Obstacles to Success; *Science*; pp. 404–410; Oct. 20, 1995; vol. 270.

Francken, Bart J.B., et al.; Human 5–Hydroxytryptamine$_{5A}$ Receptors Activate Coexpressed $G_1$ and $G_o$ Proteins in *Spodoptera frugiperda* 9 Cells; *Molecular Pharmacology*; pp. 1034–1044; May 2000; vol. 57, No. 5.

Ha, Hunjoo, et al.; Atherogenic lipoproteins enhance mesangial cell expression of platelet–derived growth factor: Role of protein tyrosine kinase and cyclic AMP–dependent protein kinase A; *J Lab Clin Med*; pp. 456–465; May 1998.

Koyama, Noriyuki, et al.; Heparan Sulfate Proteoglycans Mediate a Potent Inhibitor Signal for Migration of Vascular Smooth Muscle Cells; *Circulation Research*; pp. 305–313; Aug. 10, 1998; vol. 83, No. 3.

Kung, H.F., et al.; Dopamine D–2 Receptor Imaging Radiopharmaceuticals: Synthesis, Radiolabeling, and in Vitro Binding of (R)–(+)– and (S)–(–)–3–Iodo–2–hydroxy–6–methoxy–N–[(1–ethyl–2–pyrrolidinyl) methyl] benzamide: *Journal of Medical Chemistry*; pp. 1039–1042; 1998; vol. 31, No. 5.

Manning, William C., et al.; Use of a recombinant murine cytomegalovirus expressing vesicular stomatitis virus G protein to pseudotype retroviral vectors; *Journal of Virological Methods*; 1998; pp. 31–39; vol. 73.

McNall, Steven J., et al.; Novel Serotonin Receptors in Fasciola. Characterization by Studies on Adenylate Cyclase Activation and [$^3$H]LSD Binding; *Biochemical Pharmacology.*; pp. 2789–2797; 1984; vol. 33, No. 17.

Padia, J.K., et al.; Design and Synthesis of Novel Nonpepetide CCK–B Receptor Antagonists; *Bioorganic & Medicinal Chemistry Letters*; pp. 805–810; 1997; vol. 7, No. 7.

Padia, J.K., et al.; Novel Nonpeptide CCK–B Antagonists: Design and Development of Quinazolinone Derivatives as Potent, Selective, and Orally Active CCK–B Antogonists; *Journal of Medicinal Chemistry*, pp. 1042–1049; 1998; vol. 41, No. 7.

Palù, Giorgio, et al.; In pursuit of new developments for gene therapy of human diseases; *Journal of Biotechnology*, pp. 1–13; 1999; vol. 68.

Schall, T.J., et al.; Biology of the Rantes/SIS Cytokine Family; *Cytokine*; pp. 165–183; May 1991; vol. 3, No. 3

Schofield, J.P., et al.; Non–viral approaches to gene therapy; *British Medical Bulletin*; pp. 56–71; 1995; vol. 51, No. 1.

Verma, Inder M., et al.; Gene therapy—promises, problems and prospects; *Nature*; pp. 239–242; Sep. 18, 1997; vol. 389.

Wang, T.S., et al; A Simple Method of Preparation for [$^{123}$I]–(S)–(–)–IBZM; *Applied Radiation and Isotopes*; pp. 389–372; 1998; vol. 49, No. 4.

Beisser, Patrick S., et al.; The R33 G Protein–Coupled Receptor Gene of Rat Cytomegalovirus Plays an Essential Role in the Pathogenesis of Viral Infection; *Journal of Virology*; Mar. 1998; pp. 2352–2363; vol. 72, No. 3.

Beisser, Partick S., et al.; Delection of the R78 G Protein–Coupled Receptor Gene from Rat Cytomegalovirus Results in an Attenuated, Syncytium–Inducing Mutant Strain; *Journal of Virology*; Sep. 1999; pp. 7218–7230; vol. 73, No. 9.

Beisser, P.R., et al.; Viral Chemokine Receptors and Chemokines in Human Cytomegalovirus Trafficking and Interaction with the Immune System; *Current Topics in Microbiology and Immunology*; 2002; pp. 203–234; vol. 269; Springer; Berlin, DE; XP008009472.

Billstrom, Marcella A. et al.; Intracellular Signaling by the Chemokine Receptor US28 during Human Cytomegalovirus Infection; *Journal of Virology*, Jul. 1998; pp. 5535–5544; vol. 72, No. 7.

Bodaghi, Bahram, et al.; Chemokine Sequestration by Viral Chemoreceptors as a Novel Viral Escape Strategy: Withdrawal of Chemokines from the Environment of Cytomegalovirus–Infected Cells; *J. Exp. Med.*; Sep. 7, 1998; pp. 855–866; vol. 188, No. 5.

Borst, M.E., et al.; Development of a cytomegalovirus vector for somatic gene therapy; *Bone Marrow Transplantation*; 2000; pp. S80–S82; Supp. 2.

Cha, Tai–An, et al.; Human Cytomegalovirus Clinical Isolates Carry at Least 19 Genes Not Found in Laboratory Strains; *Journal of Virology*; Jan. 1996; pp. 78–83; vol. 70, No. 1.

Chee, M.S., et al.; Analysis of the Protein–Coding Content of the Sequence of Human Cytomegalovirus Strain AD169; *Current Topics in Microbiology and Immunology*; 1990; pp. 126–169; vol. 154.

Chee, M.S., et al.; Human cytomegalovirus encodes three G protein–coupled receptor homologues; *Nature*; Apr. 19, 1990; pp. 774–777; vol. 344.

Craigen, J.L., et al.; Human cytomegalovirus infection up–regulates interleukin–8 gene expression and stimulates neutrophil transendothelial migration; *Immunology*; 1997; pp. 138–145; vol. 92.

Davis–Poynter, Nicholas J., et al.; Master of deception: A review of herpesvirus immune evasion strategies; *Immunololgy and Cell Biology*; 1996; pp. 513–522; vol. 74.

Davis–Poynter, Nicholas J., et al.; Identification and Characterization of G Protein–Coupled Receptor Homology Encoded by Murine Cytomegalovirus; *Journal of Virology*; Feb. 1997; pp. 1521–1529; vol. 71, No. 2.

Farrell, H.E., et al.; Inhibition of natural killer cells by a cytomegalovirus MHC class I homologue in vivo; *Nature*; Apr. 3, 1997; pp. 510–514; vol. 386.

Fleming, Peter, et al.; The Murine Cytomegalovirus Chemokine Homolog, m131/129, Is a Determinant of Viral Pathogenicity; *Journal of Virology*; Aug. 1999; pp. 6800–6809; vol. 73, No. 8.

Gao, Ji–Liang; et al.; Human Cytomegalovirus Open Reading Frame US28 Encodes a Functional β Chemokine Receptor; *The Journal of Biological Chemistry*; Nov. 18, 1994; pp. 28539–28542; vol. 269, No. 46.

GenBank Accession No.: L20501; May, 2, 1996.
GenBank Accession No.: AF073831; Jun. 23, 2000.
GenBank Accession No.: AF073832; Jun. 23, 2000.
GenBank Accession No.: AF073833; Jun. 23, 2000.
GenBank Accession No.: AF073834; Jun. 23, 2000.
GenBank Accession No.: AF073835; Jun. 23, 2000.
GenBank Accession No.: X17403; Feb. 10, 1999.
GenBank Accession No.: X53293; Dec. 1, 1992.

Gilbert, Mark J., et al.; Cytomegalovirus selectively blocks antigen processing and presentation of its immediate–early gene product; *Nature*; Oct. 24, 1996; pp. 720–722; vol. 383.

Gompels, U.A.; et al.; The DNA Sequence of Human Herpesvirus–6: Structure, Coding Content, and Genome Evolution; *Virology*; 1995; pp. 29–51; vol. 209.

Grundy, Jane E., et al.; Cytomegalovirus–Infected Endothelial Cells Recruit Neutrophils by the Secretion of C–X–C Chemokines and Transmit Virus by Direct Neutrophil–Endothelial Cell Contact and during Neutrophil Transendothelial Migration; *The Journal of Infectious Diseases*; 1998; pp. 1465–1474; vol. 177.

Harrison, Jeffrey K., et al.; Role for neuronally derived fractalkine in mediating interactions between neurons and CX3CR1–expressing microglia; *Proc. Natl. Acad. Sci. USA*; Sep. 1998; pp. 10896–10901; vol. 95.

Hirsch, Alec J., et al.; Human Cytomegalovirus Inhibits Transcription of the CC Chemokine MCP-1 Gene; *Journal of Virology*; Jan. 1999; pp. 404–410; vol. 73, No. 1.

Humar A., et al.; Elevated Serum Cytokines Are Associated with Cytomegalovirus Infection and Disease in Bone Marrow Transplant Recipients; *The Journal of Infectious Diseases*; 1999; pp. 484–488; vol. 179.

Isegawa, Yuji, et al.; Human Herpesvirus 6 Open Reading Frame U12 Encodes a Functional β–Chemokine Receptor; *Journal of Virology*; Jul. 1998; pp. 6104–6112; vol. 72, No. 7.

Kledal, Thomas N.; et al.; A Broad–Spectrum Chemokine Antagonist Encoded by Kaposi's Sarcoma–Associated Herpesvirus; *Science*; Sep. 12, 1997; pp. 1656–1659; vol. 277.

Kledal, Thomas N.; et al.; Selective recognition of the membrane–bound $CX_3C$ chemokine, fractalkine, by the human cytomegalovirus–encoded broad–spectrum receptor US28; *FEBS Letters*; 1998; pp. 209–214; vol. 441.

Kleijnen, Maurits F., et al.; A mouse cytomegalovirus glycoprotein, gp34, forms a complex with folded class I MHC molecules in the ER which is not retained but is transported to the cell surface; *EMBO Journal*; 1997, pp. 685–694; vol. 16, No. 4.

Kotenko, Sergei, et al.; Human cytomegalovirus harbors it own unique IL–10 homolog (cmvIL–10); Feb. 15, 2000, pp. 1695–1700, vol. 97, No. 4.

Kuhn, Donald, E., et al.; The Cytomegalovirus US28 Protein Binds Multiple CC Chemokines with High Affinity; *Biochemical and Biophysical Research Communications*, Jun. 6, 1995; pp. 325–330; vol. 211, No. 1.

Lockridge, Kristen M.; et al.; Primate Cytomegaloviruses Encode and Express an IL–10–like Protein; *Virology*; 2000; pp. 272–280; vol. 268.

Mahalingam, Surendran, et al.; Chemokines and chemokine receptors in infectious diseases; *Immunology and Cell Biology*; 1999; pp. 469–475; vol. 77.

Margulies, Barry J., et al.; Identification of the Human Cytomegalovirus G. Protein–Coupled Receptor Homologue Encoded by UL33 in Infected Cells and Enveloped Virus Particles; *Virology*; 1996; pp. 111–125; vol. 225.

Martin, W. John; Chemokine Receptor–Related Genetic Sequences in an African Green Monkey Simian Cytomegalovirus–Derived Stealth Virus; *Experimental and Molecular Pathology*; 2000; pp. 10–16.

Michelson, S., Interaction of Human Cytomegalovirus with Monocytes/Macrophages: A Love–Hate Relationship; *Path. Biol.*; 1997; pp. 146–158; vol. 45, No. 2.

Michaelson, Susan; Cytomegalovirus (CMV) and sequestration of chemokines; *Eur. Cytokine Netw.*; Jun. 1999; pp. 286–287; vol. 10, No. 2.

Michelson, Susan, et al.; Modulation of RANTES Production by Human Cytomegalovirus Infection of Fibroblasts; *Journal of Virology*; Sep. 1997; pp. 6495–6500; vol. 71, No. 9.

Monti, Gianpaola, et al.; Intrapulmonary Production of RANTES During Rejection and CMV Pneumonitis After Lung Transplantation; *Transplantation*; Jun. 27, 1996; pp. 1757–1762; vol. 61, No. 12.

Murayama, Tsugiya, et al.; Potential Involvement of IL–8 in the pathogenesis of human cytomegalovirus infection; *Journal of Leukocyte Biology*; Jul. 1998; pp. 62–67; vol. 64.

Neote, Kuldeep, et al. Molecular Cloning, Functional Expression, and Signaling Characteristics of a C–C Chemokine Receptor; *Cell*; Feb. 12, 1993; pp. 415–525; vol. 72.

Nishiyori, Atsushi, et al.; Localization of fractalkine and $CX_3CR1$ mRNAs in rat brain: does fractalkine play a role in signaling from neuron to microglia?; *FEBS Letters*; 1998; pp. 167–172; vol. 429.

Nordøy,Ingvild, et al.; Immunologic Parameters as Predictive Factors of Cytomegalovirus Disease in Renal Allograft Recipients; *The Journal of Infectious Diseases*; 1999; pp. 195–198; vol. 180.

Pass, Robert F., et al.; A Subunit Cytomegalovirus Vaccine Based on Recombinant Envelope Glycoprotein B. and a New Adjuvant; *The Journal of Infectious Diseases*; 1999; pp. 970–975; vol. 180.

Penfold, Mark E.T.; et al.; Cytomegalovirus encodes a potent α chemokine; *Proc. Natl. Acad. Sci. USA*; Aug. 1999; pp. 9839–9844; vol. 96.

Pleskoff, Olivier, et al; The Cytomegalovirus–Encoded Chemokine Receptor US28 Can Enhance Cell–Cell Fusion Mediated by Different Viral Proteins; *Journal of Virology*; Aug. 1998; pp. 6389–6397; vol. 72, No. 8.

Quinnan Jr., M.D., Gerald V., et al.; Comparative Virulence and Immunogenicity of the Towne Strain and a Nonattenuated Strain of Cytomegalovirus; *Annals of Internal Medicine*; 1984; pp. 478–483; vol. 101.

Rawlinson, William D., et al.; Analysis of the Complete DNA Sequence of Murine Cytomegalovirus: *Journal of Virology*; Dec. 1996; pp. 8833–8849; vol. 70, No. 10.

Reusch, UWE, et al.; A cytomegalovirus glycoprotein re–routes MHC class I complexes to lysosomes for degradation; *EMBO Journal*; 1999; pp. 1081–1091; vol. 18, No. 4.

Reyburn, Hugh T., et al.; The Class I MHC homologue of Human Cytomegalovirus inhibits attach by natural killer cells; *Nature*; Apr. 3, 1997; pp. 514–517; vol. 386.

Rollins, Barrett J.; Chemokines; *Blood*; Aug. 1, 1997; pp. 909–928; vol. 90, No. 3.

Saederup, Noah, et al.; Cytomegalovirus–encoded β chemokine promotes monocyte–associated viremia in the host; *Proc. Natl. Acad. Sci. USA*; Sep. 1999; pp. 10881–10886; vol. 96.

Sallusto, Federica, et al.; Chemokines and chemokine receptors in T–cell priming and Th1/Th2–mediated responses; *Immunology Today*; Dec. 1998; pp. 568–574; vol. 19, No. 12.

Seow, Heng–Fong; Pathogen interactions with cytokines and host defence: an overview; *Veterinary Immunology and Immunopathology*; 1998; pp. 139–148; vol. 63.

Shellam, G.R.; The Potential of Murine Cytomegalovirus as a Viral Vector for Immunocontraception; *Reprod. Fertil. Dev.*; 1994; pp. 401–409; vol. 6.

Streblow, Daniel N., et al.; The Human Cytomegalovirus Chemokine Receptor US28 Mediates Vascular Smooth Muscle Cell Migration; *Cell*; Nov. 24, 1999; pp. 511–520; vol. 99.

Swiss–Prot Accession No. P16849; Aug. 1, 1990.

Thäle, Regine, et al.; Identification and Expression of an Murine Cytomegalovirus Early Gene Coding for an Fc Receptor; *Journal of Virology*; Dec. 1994; pp. 7757–7765; vol. 68, No. 12.

Tomasec, Peter, et al.; Surface Expression of HLA–E, an Inhibitor of Natural Killer Cells, Enhanced by Human Cytomegalovirus gpUL40; *Science*; Feb. 11, 2000; pp. 1031–1033; vol. 287.

Vieira, Jeffrey, et al.; Functional Analysis of the Human Cytomegalovirus US28 Gene by Insertion Mutagenesis with the Green Fluorescent Protein Gene: *Journal of Virology*; Oct. 1998; pp. 8158–8165; vol. 72, No. 10.

Ward, Stephen G., et al.; Chemokines and T Lymphocytes: More that an Attraction; *Immunity*; Jul. 1998; pp. 1–11; vol. 9.

Ziegler, Heike, et al.; A mouse Cytomegalovirus Glycoprotein Retains MHC Class I Compleses in the ERGIC/cis–Golgi Compartments; *Immunity*, Jan. 1997; pp. 57–66; vol. 6.

* cited by examiner

| | | | |
|---|---|---|---|
| VHL/E | 1 | ATGACACCGACGACGACGACCGCGGAACTCACG | 33 |
| VHL/E | 34 | ACGGAGTTTGACTACGACGATGAAGCGACTCCC | 66 |
| VHL/E | 67 | TGTGTCCTCACCGACGTGCTTAATCAGTCGAAG | 99 |
| VHL/E | 100 | CCAGTCACGTTGTTTCTGTACGGCGTTGTCTTT | 132 |
| VHL/E | 133 | CTCTTCGGTTCCATCGGCAACTTCTTGGTGATC | 165 |
| VHL/E | 166 | TTCACCATCACCTGGCGACGTCGGATTCAATGT | 198 |
| VHL/E | 199 | TCCGGCGATGTTTACTTTATCAACCTCGCGGCC | 231 |
| VHL/E | 232 | GCCGATTTGCTTTTCGTTTGTACACTACCTCTG | 264 |
| VHL/E | 265 | TGGATGCAATACCTCCTAGATCACAACTCCCTA | 297 |
| VHL/E | 298 | GCCAGCGTGCCGTGTACGTTACTCACTGCCTGT | 330 |
| VHL/E | 331 | TTCTACGTGGCTATGTTTGCCAGTTTGTGTTTT | 363 |
| VHL/E | 364 | ATCACGGAGATTGCACTCGATCGCTACTACGCT | 396 |
| VHL/E | 397 | ATTGTTTACATGAGATATCGGCCTGTAAAACAG | 429 |
| VHL/E | 430 | GCCTGCCTTTTCAGTATTTTTTGGTGGATCTTT | 462 |
| VHL/E | 463 | GCCGTGATCATCGCCATTCCACACTTTATGGTG | 495 |
| VHL/E | 496 | GTGACCAAAAAAGACAATCAATGTATGACCGAC | 528 |
| VHL/E | 529 | TACGACTACTTAGAGGTCAGTTACCCGATCATC | 561 |
| VHL/E | 562 | CTCAACGTAGAACTCATGCTCGGTGCTTTCGTG | 594 |
| VHL/E | 595 | ATCCCGCTCAGTGTCATCAGCTACTGCTACTAC | 627 |
| VHL/E | 628 | CGCATTTCCAGAATCGTTGCGGTGTCTCAGTCG | 660 |
| VHL/E | 661 | CGCCACAAAGGCCGCATTGTACGGGTACTTATA | 693 |
| VHL/E | 694 | GCGGTCGTGCTTGTCTTTATCATCTTTTGGCTG | 726 |
| VHL/E | 727 | CCGTACCACCTGACGCTGTTTGTGGACACGTTG | 759 |
| VHL/E | 760 | AAACTGCTCAAATGGATCTCCAGCAGCTGCGAG | 792 |
| VHL/E | 793 | TTCGAAAAATCACTCAAGCGCGCGCTCATCTTG | 825 |
| VHL/E | 826 | ACCGAGTCACTCGCCTTTTGTCACTGTTGTCTC | 858 |
| VHL/E | 859 | AATCCGCTGCTGTACGTCTTCGTGGGCACCAAG | 891 |
| VHL/E | 892 | TTTCGGCAAGAACTGCACTGTCTGCTGGCCGAG | 924 |
| VHL/E | 925 | TTTCGCCAGCGACTGTTTTCCCGCGATGTATCC | 957 |
| VHL/E | 958 | TGGTACCACAGCATGAGCTTTTCGCGTCGGAGC | 990 |
| VHL/E | 991 | TCGCCGAGCCGAAGAGAGACGTCTTCCGACACG | 1023 |
| VHL/E | 1024 | CTGTCCGACGAGGCGTGTCGCGTCTCACAAATT | 1056 |
| VHL/E | 1057 | ATACCGTAA | 1065 |

FIG. 1A

| | | | |
|---|---|---|---|
| VHL/E | 1 | MTPTTTTAELTTEFDYDDEATPCVLTDVLNQSK | 33 |
| VHL/E | 34 | PVTLFLYGVVFLFGSIGNFLVIFTITWRRRIQC | 66 |
| VHL/E | 67 | SGDVYFINLAAADLLFVCTLPLWMQYLLDHNSL | 99 |
| VHL/E | 100 | ASVPCTLLTACFYVAMFASLCFITEIALDRYYA | 132 |
| VHL/E | 133 | IVYMRYRPVKQACLFSIFWWIFAVIIAIPHFMV | 165 |
| VHL/E | 166 | VTKKDNQCMTDYDYLEVSYPIILNVELMLGAFV | 198 |
| VHL/E | 199 | IPLSVISYCYYRISRIVAVSQSRHKGRIVRVLI | 231 |
| VHL/E | 232 | AVVLVFIIFWLPYHLTLFVDTLKLLKWISSSCE | 264 |
| VHL/E | 265 | FEKSLKRALILTESLAFCHCCLNPLLYVFVGTK | 297 |
| VHL/E | 298 | FRQELHCLLAEFRQRLFSRDVSWYHSMSFSRRS | 330 |
| VHL/E | 331 | SPSRRETSSDTLSDEACRVSQIIP | 354 |

FIG. 1B

| | | |
|---|---|---|
| human US28 | 1 | MTPTT- - - - - - - - - - - - - - - - - - - - - - - - - - - - 5 |
| rhesus US28.1 | 1 | M- - - - - - - - - - - - - - - - - - - - - - - - - - - - -M- 1 |
| rhesus US28.2 | 1 | MTNA- - - - - - - - - - - - - - - - - - - - - - - - - - - - 4 |
| rhesus US28.3 | 1 | MTNT- - - - - - - - - - - - - - - - - - - - - - - - - - - - 4 |
| rhesus US28.4 | 1 | M- - - - - - - - - - - - - - - - - - - - - - - - - - - - - - 0 |
| rhesus US28.5 | 1 | MTTTTMSATTNSSTTPQASSTTMTTKTSTPGN 32 |

| | | |
|---|---|---|
| human US28 | 6 | - - - -TTAELTT- - - - - - - - - - - - - - - - - - - - - - 12 |
| rhesus US28.1 | 2 | - - - - - - - - - - - - - - - - - - - - - - - - - - - - - - 1 |
| rhesus US28.2 | 5 | - - - - - - - - - - - - - - - - - - - - - - - - - - - - - - 4 |
| rhesus US28.3 | 5 | - - - - - - - - - - - - - - - - - - - - - - - - - - - - - - 4 |
| rhesus US28.4 | 1 | - - - - - - - - - - - - - - - - - - - - - - - - - - - - - - 0 |
| rhesus US28.5 | 83 | TTTGTTSTLTTISTTSNATSITSNLSTTGNQT 64 |

| | | |
|---|---|---|
| human US28 | 13 | - - - - - - - - - - - - - - - - - - - - - - - - - - - - - - 12 |
| rhesus US28.1 | 2 | - - - - - - - - - - - - - - - - - - - - - - - - - - -NNT 4 |
| rhesus US28.2 | 5 | - - - - - - - - - - - - - - - - - - - - - - - - - - - -GH- 6 |
| rhesus US28.3 | 5 | - - - - - - - - - - - - - - - - - - - - - - - - - - - -NNT 7 |
| rhesus US28.4 | 1 | - - - - - - - - - - - -NSSQHNISVFLSIGA- - - - - 15 |
| rhesus US28.5 | 65 | ATTNATTFSSTLTTSTNISSTFSTVSTVASNA 96 |

| | | |
|---|---|---|
| human US28 | 13 | - - - - - - - - - - - - - - - - - - - - - - - - - - - - - - 12 |
| rhesus US28.1 | 5 | SCN- - - - - - - - - - - - - - - - - - - - - - - - - - -F 8 |
| rhesus US28.2 | 7 | -CH- - - - - - - - - - - - - - - - - - - - - - - - - - - -I 9 |
| rhesus US28.3 | 8 | TCH- - - - - - - - - - - - - - - - - - - - - - - - - - - -L 11 |
| rhesus US28.4 | 16 | - - - - - - - - - - - - - - - - - - - - - - - - -GPVITG- 21 |
| rhesus US28.5 | 97 | TCNSTITTNITTAFTTAANTTASSLTSIVTSL 128 |

| | | |
|---|---|---|
| human US28 | 13 | - - - - - - -EFDYDEDATPCMFTDVLNQSKPVTL 37 |
| rhesus US28.1 | 9 | NVTLNASA- - - - - - - - - - - - - - - -PSRYIAI 23 |
| rhesus US28.2 | 10 | NESLASYG- - - - - - - - - - - - - - - -IAPAATI 24 |
| rhesus US28.3 | 12 | NGTFETFK- - - - - - - - - - - - - - - - -ITRPVAI 26 |
| rhesus US28.4 | 22 | - - - - - - - - - - - - - - - - - - - - - - - - - - - - - - 21 |
| rhesus US28.5 | 129 | ATTIETTSFDYDESAEACNLTDIVHTTRSVTV 160 |

FIG. 2A

| | | |
|---|---|---|
| human US28 38 | `FLYGVVFLFGSIGNF-LVIFTITWRRRIQCSG` | 68 |
| rhesus US28.1 24 | `AMYSIVICIGLVGNLLLCIVLVK-KRKLRYSS` | 54 |
| rhesus US28.2 25 | `TLYSIAGICGVTGNLLILLVLFT-RRIHWFAN` | 55 |
| rhesus US28.3 27 | `SAYTVLVVIGLLGNIVLLSVLVV-KRKLKFPN` | 57 |
| rhesus US28.4 22 | `--YTCVFLFGILGHFYLYWKNHQRRHRTNSFS` | 51 |
| rhesus US28.5 61 | `TFYTIIFILGLLGNF-LVLMTIIWNRRISFMV` | 191 |
| human US28 69 | `DVYFINLAAADLLFVCTLPLWMQYLLDHNSLA` | 100 |
| rhesus US28.1 55 | `DVYFFHASMADLVSTVMLPLWLHYVLNFAQLS` | 86 |
| rhesus US28.2 56 | `DIYYLNMIFTDFLVFITLPAWVYLLNYTQLS` | 87 |
| rhesus US28.3 58 | `DIYFFNASLADVFAVCMLPAWVNYALDSTQLS` | 89 |
| rhesus US28.4 52 | `DVLFRHLMITEEVFTLTIPVWAYHLTTHGNLP` | 83 |
| rhesus US28.5 192 | `EIYFVNLAISDLMFVCTLPFWIMYLLEHDVMS` | 223 |
| human US28 101 | `SVPCTLLTACFYVAMFASLCFITEIALDRYYA` | 132 |
| rhesus US28.1 87 | `RGACISFSVTFYVPLFVQAWLLISIAMER-YS` | 117 |
| rhesus US28.2 88 | `HYACIALSFVFYVSIFIQADFMVAVAIER-YR` | 118 |
| rhesus US28.3 90 | `KFSCITFTFGFYVSLFIQAWMLILVTLER-YG` | 120 |
| rhesus US28.4 84 | `GSWCRSLTFVFYLTVFARAFFYLLLIWDR-YS` | 114 |
| rhesus US28.5 24 | `HASCVAMTAIFYCALFASTVFLLLIVLDRCYA` | 255 |
| human US28 133 | `IVYMRYRPVKQ------ACLFSIFWWIFAVI` | 157 |
| rhesus US28.1 118 | `NLVWMAPISVK---TAFKHCIGT---WIVSAF` | 143 |
| rhesus US28.2 119 | `SLVKNKPLSVK---KASVSCACI---WIIVII` | 144 |
| rhesus US28.3 121 | `SLVWIAPITRN---KAIANCVLF---WLVSIF` | 146 |
| rhesus US28.4 115 | `VIICRHPLPVNLNYSQVIG---LSVW--LVAV` | 141 |
| rhesus US28.5 256 | `ILLGTEKANRRLLRNAVSGCMLM---WGLCFI` | 284 |
| human US28 158 | `IAIPHFMVVTK-KDNQC-MTDYDY-LEVSYPI` | 186 |
| rhesus US28.1 144 | `VASPYYAYRNSHDEHECILGNYTWHINEPLHT` | 175 |
| rhesus US28.2 145 | `VSSPYYMFRSQHETNSCILGNYTWHMNSPFRT` | 176 |
| rhesus US28.3 147 | `LAAPYYSFRNESNEHQCIMRNYTWSVGETWHI` | 178 |
| rhesus US28.4 142 | `LSASPFSIFNG-SVKQC-LGNMG-SIPSESSA` | 170 |
| rhesus US28.5 285 | `LALPHFIFMKK-GTNVC-VAEYEPGLNNFYVI` | 314 |

FIG. 2B

```
human US28    187  I L N V E L M L G A F V I P L S V I S Y C Y Y R I S R I V A V S  218
rhesus US28.1 176  C M D V I I V W T F L A P V L V T I I A S V K M - R R T T W G  206
rhesus US28.2 177  T M D A S I N I W S F V V P A V T T L L I A R R I Y V - C T S G  207
rhesus US28.3 179  A L D F L I T L I T F I M P V T I V L A L S F K M A R W S T F G  210
rhesus US28.4 171  V L N L E V H L C S F W L P L I M S A N C Y Y Q A K R R A S P D  202
rhesus US28.5 245  F I N T E V N L C T L V L P A A A I I Y W Y L K L T K A L K T H  346 human US28    219  Q S - R H K G R I V R V L I A V V L V F I I F W L P Y H L T L F  249
rhesus US28.1 207  N T - R L N E K N S D I L I V L V V M I V F F W G P F N I V L V  237
rhesus US28.2 208  N K - K M N A R A S G L L E A M V I S M L F F G G L F N L N I F  238
rhesus US28.3 211  Y R - N L T S R T S L I L I L I L T V A A G F W G P F H L F M F  241
rhesus US28.4 203  Q - - L H E L Y R C S L L I T I I T T Y A I V W F P F H L A L L  232
rhesus US28.5 347  E R L R H R L T S L N I V L A V V I V F A L F W L P Y N L M L M  378 human US28    250  V D T L K L - L K W I S S S C E F E R S L K R A L I L T E S L A  280
rhesus US28.1 238  I D N I L Q R Y Y D T - T N C D V E K I K H I M A M I S E A I V  268
rhesus US28.2 239  R D - I V S D T S E D N K D C T Y L K Q E H F I R M V G V A L V  269
rhesus US28.3 242  I E N V A G Q I Y H I Q K D C W Y L Q L R H L C S L M T E T L V  273
rhesus US28.4 233  I D A L I S - I S H V E P S S A L H W A - - S I V V T C K S F T  261
rhesus US28.5 379  M Y S L V H - M Q - I P W E C S S E K I L R R S L I I T E S I A  408 human US28    281  F C H C C L N P L L Y V F V G T K F R Q E L H C L L A E F R Q R  312
rhesus US28.1 269  Y F R G I T A P I I Y V G I S G R F R E E I Y S L F R R Q P Y N  300
rhesus US28.2 270  Y G R A I F N P F M Y M C V S T R L R Q E I K C L F M R I P Y E  301
rhesus US28.3 274  F L R S V F N P Y I Y M I I S Y K F R Q Q V R S L L K R T Q Y D  305
rhesus US28.4 262  F V Y A G I S P L V Y F T C C P T V R R E L L M S L R P F F T -  292
rhesus US28.5 409  L S H C C I N P I I Y L L F G P R C R S E F C H L L R C C F T R  440 human US28    313  L F S R D V S W - - Y H S M S F S R R S S P S R R E T S S D T L  342
rhesus US28.1 301  D L D P D A N - - - - - Q F M I E L T S Q G R S R N R N A R Q S  327
rhesus US28.2 302  T L D A E H A - - - - - K L M V N L K N R N A N V P D P K - - -  325
rhesus US28.3 306  A L D T T Q L - - - - - A E T M Q L K A K G V P V S D P A - - -  329
rhesus US28.4 293  - - - - - - - W I S S K T R R G Y A P I K T Q P L N I P D E P I  317
rhesus US28.5 441  L - C P H R S W S S I R A E T V S I S L S H S Q V S A S S E D D  471 human US28    343  S D E V C R V S Q I I P                                          354
rhesus US28.1 328  E S N V P Q P E E C F W                                          339
rhesus US28.2 326  - - - - P R E Y E S V L                                          333
rhesus US28.3 330  - - - - P H D C E C F L                                          337
rhesus US28.4 318  D N K S P H L L N - - E                                          327
rhesus US28.5 472  D N D V H D E L Q F L I                                          483
```

FIG. 2C

| | | | |
|---|---|---|---|
| human UL78 | 1 | MSPSVEETTSVTESIMFAIVSFKHMGPFEGY | 31 |
| rhesus UL78 | 1 | - - - - - - - - - - - - - - - - - - - - - - - - - - - - - - - | 0 |
| human UL78 | 32 | SMSADRAASDLLIGMFGSVSLVNLLTLIGCL | 62 |
| rhesus UL78 | 1 | -MITERVLAGILAGMTAAGSLVILLAVV--M | 28 |
| human UL78 | 63 | WVLRVTRP--PVSVMIFTWNLVLSQFFSILA | 91 |
| rhesus UL78 | 29 | WLNMLDRAGMPMAVGHYTGNLVLTQVICIFS | 59 |
| human UL78 | 92 | TMLSKGIMLRGALNLSLCRLVLFVDDVGLYS | 122 |
| rhesus UL78 | 60 | -MLASKIVGMTSAANMGFCGIVVFLEDTGLY | 89 |
| human UL78 | 123 | TALFFLFLILDRLSAISYGRDLWHHE-TREN | 152 |
| rhesus UL78 | 90 | VTSLLFMFMILDRMAAFLNGRLFWRQQTTKQ | 120 |
| human UL78 | 153 | AGVALYAVAFAWVLSIVAAVPTAATGSLDYR | 183 |
| rhesus UL78 | 121 | NLSTSVYIILFCWVLGMAAAVPSAAVAAPNS | 151 |
| human UL78 | 184 | WLGCQIPIQYAAVDLTIKMWFLLGAPMIAVL | 214 |
| rhesus UL78 | 152 | RWERCEIPVSYAAIDMIVKLWFVLLAPVVLI | 182 |
| human UL78 | 215 | ANVVELAYSDRRDHVWSYVGRVCTFYVTCLM | 245 |
| rhesus UL78 | 183 | MAVIIQSSYHRDRERIWYARRVFMFYTACF | 213 |
| human UL78 | 246 | LFVPYYCFRV------LRGV-LQPASAAGTG | 269 |
| rhesus UL78 | 214 | VMMVPYYFVRVMLSDFALVDIKTKTANSDGC | 244 |
| human UL78 | 270 | FGIMDYVELATRTLLTMRLGILPLFIIAFFS | 300 |
| rhesus UL78 | 245 | DSTFLDYLNMFTHVIYSFKLVVFALFIVLFC | 275 |
| human UL78 | 301 | REPTKDLDDSFDYLVERCQQSCHGHFVRRLV | 331 |
| rhesus UL78 | 276 | SINPMETLEECLERADAERQSRSEASQGERR | 306 |
| human UL78 | 332 | QALKRAMYSVELAVCYFSTSVRDVAEAVKKS | 362 |
| rhesus UL78 | 307 | LPINTCCIKLIELIKQYVSTLSKATRDNSGE | 337 |
| human UL78 | 363 | SSRCYADATSAAVVVTTTSEKATLVEHAEG | 393 |
| rhesus UL78 | 338 | RANLPENAEDIGTTGSDQLPTEVTVTPNSSA | 368 |
| human UL78 | 394 | MASEMCPGTTIDVSAESSSVLCTDGENTVAS | 424 |
| rhesus UL78 | 369 | VFSTGGTVSPV | 379 |
| human UL78 | 425 | DATVTAL | 431 |

FIG. 3

| | | | |
|---|---|---|---|
| H UL33 | 1 | M- - - - - - - - - - - - - - - - - - - - - - - - - - - - - - - | 1 |
| HUL33splice | 1 | M D T I I H N S I - - - - - - - - - - - - - - - - - - - - - - | 9 |
| RhUL33 | 1 | M- - - - - - - - - - - - - - - - - - - - - - - - - - - - - - - | 1 |
| RhUL33splice | 1 | M A V T L R G G S P I N F K L M I V S H R N R K F H E I R L F Q | 32 |

| | | | |
|---|---|---|---|
| H UL33 | 2 | - - - - - - - - - - - - - - - - - - - - - - - - - - - - | 1 |
| HUL33splice | 10 | R N N T P P - - - - - - - - - - - - - - - - - H I N D T C N M | 23 |
| RhUL33 | 2 | - - - - - - - - - - - - - - - - - - - - - - - - - - - - | 1 |
| RhUL33splice | 33 | R S A I R P G G L W K P F F T T E R E T N S I L H I N T T C N V | 64 |

| | | | |
|---|---|---|---|
| H UL33 | 2 | T G P L F A I R T T E A V L N T F I I F V G G P L N A I V L I T | 33 |
| HUL33splice | 24 | T G P L F A I R T T E A V L N T F I I F V G G P L N A I V L I T | 55 |
| RhUL33 | 2 | - - - - - - - - - - - - - - - - - - - - - - - - - - - - - - - | 1 |
| RhUL33splice | 65 | T D S L Y A A K L G E A L V N S A L A L F G T P L N A I V L V T | 96 |

| | | | |
|---|---|---|---|
| H UL33 | 34 | Q L L T N R V L G Y S T P T I Y M T N L Y S T N F L T L T V L P | 65 |
| HUL33splice | 56 | Q L L T N R V L G Y S T P T I Y M T N L Y S T N F L T L T V L P | 87 |
| RhUL33 | 2 | - - - - - - - - - - - - - - - - T N L Y S A N F L T L I V L P | 16 |
| RhUL33splice | 97 | Q L L A N R V H G Y S T P I I Y M T N L Y S A N F L T L I V L P | 128 |

| | | | |
|---|---|---|---|
| H UL33 | 66 | P I V L S N Q W L L P A G V A S C K F L S V I Y Y S S C T V G F | 97 |
| HUL33splice | 88 | P I V L S N Q W L L P A G V A S C K F L S V I Y Y S S C T V G F | 119 |
| RhUL33 | 17 | P I V L S N Q H L L P A S A V T C K F L S L L Y Y S S C S V G F | 48 |
| RhUL33splice | 129 | P I V L S N Q H L L P A S A V T C K F L S L L Y Y S S C S V G F | 160 |

| | | | |
|---|---|---|---|
| H UL33 | 98 | A T V A L I A A D R Y R V L H K R T Y A R Q S Y R S T Y M I L L | 129 |
| HUL33splice | 120 | A T V A L I A A D R Y R V L H K R T Y A R Q S Y R S T Y M I L L | 151 |
| RhUL33 | 49 | A T V A L I A A D R Y R V I H R R T Q A R Q S Y R N T Y M I V G | 80 |
| RhUL33splice | 161 | A T V A L I A A D R Y R V I H R R T Q A R Q S Y R N T Y M I V G | 192 |

| | | | |
|---|---|---|---|
| H UL33 | 130 | L T W L A G L I F S V P A A V Y T T V V M H H D A N D T N N T N | 161 |
| HUL33splice | 152 | L T W L A G L I F S V P A A V Y T T V V M H H D A N D T N N T N | 183 |
| RhUL33 | 81 | L T W L I G L I C A T P G G V Y T T I V A H R D G E - - S D A Q | 110 |
| RhUL33splice | 193 | L T W L I G L I C A T P G G V Y T T I V A H R D G E - - S D A Q | 222 |

FIG. 4A

| | | | |
|---|---|---|---|
| H UL33 | 162 | GHATCVLYFVAEEVHTVLLSWKVLLTMVWGAA | 193 |
| HUL33splice | 184 | GHATCVLYFVAEEVHTVLLSWKVLLTMVWGAA | 215 |
| RhUL33 | 111 | RHNTCIMHFAYDEVY-VLMVWKLLIVLVWGIV | 141 |
| RhUL33splice | 223 | RHNTCIMHFAYDEVY-VLMVWKLLIVLVWGIV | 253 |
| H UL33 | 194 | PVIMMTWFYAFFYSTVQRTSLKQRSRTLTFVS | 225 |
| HUL33splice | 216 | PVIMMTWFYAFFYSTVQRTSLKQRSRTLTFVS | 247 |
| RhUL33 | 142 | PVVMMSWFYAFFYNTVQRTAKKQQ-RTLKFVK | 172 |
| RhUL33splice | 254 | PVVMMSWFYAFFYNTVQRTAKKQQ-RTLKFVK | 284 |
| H UL33 | 226 | VLLISFVALQTPYVSLMIFNSYATTAWPMQCE | 257 |
| HUL33splice | 248 | VLLISFVALQTPYVSLMIFNSYATTAWPMQCE | 279 |
| RhUL33 | 173 | VLLLSFIIIQTPYVSIMIFNTYATVGWPMECA | 204 |
| RhUL33splice | 285 | VLLLSFIIIQTPYVSIMIFNTYATVGWPMECA | 316 |
| H UL33 | 258 | HLTLRRTIGTLARVVPHLHCLINPILYALLGH | 289 |
| HUL33splice | 280 | HLTLRRTIGTLARVVPHLHCLINPILYALLGH | 311 |
| RhUL33 | 205 | DLTRRRVINTFSRLVPNLHCMVNPILYALMGN | 236 |
| RhUL33splice | 317 | DLTRRRVINTFSRLVPNLHCMVNPILYALMGN | 348 |
| H UL33 | 290 | DFLQRMRQCFRGQLLDRRAFLRSQNNQRATAE | 321 |
| HUL33splice | 312 | DFLQRMRQCFRGQLLDRRAFLRSQNNQRATAE | 343 |
| RhUL33 | 237 | DFVSKVGQCFRGELTNRRTFLRSKQQARNSDD | 268 |
| RhUL33splice | 349 | DFVSKVGQCFRGELTNRRTFLRSKQQARNSDD | 380 |
| H UL33 | 322 | TNLAAGNNSQSVATSLDTNSKNYNQHAKRSVS | 353 |
| HUL33splice | 344 | TNLAAGNNSQSVATSLDTNSKNYNQHAKRSVS | 375 |
| RhUL33 | 269 | VPTIVSQQP-ATPTIVNKPEK--NPHVKRGVS | 297 |
| RhUL33splice | 381 | VPTIVSQQP-ATPTIVNKPEK--NPHVKRGVS | 409 |
| H UL33 | 354 | FNFPSGTWKGGQKTASNDTSTKIPHRLSQSHH | 385 |
| HUL33splice | 376 | FNFPSGTWKGGQKTASNDTSTKIPHRLSQSHH | 407 |
| RhUL33 | 298 | FSVSASSELAAAKKAKDKA-----KRLSMSHQ | 324 |
| RhUL33splice | 410 | FSVSASSELAAAKKAKDKA-----KRLSMSHQ | 436 |
| H UL33 | 386 | NLSGV | 390 |
| HUL33splice | 408 | NLSGV | 412 |
| RhUL33 | 325 | NLRLT | 329 |
| RhUL33splice | 437 | NLRLT | 441 |

FIG. 4B

Sucrose Virions/CX3C binding

- ■ HDF Toledo Virions
- ◆ HDF Toledo delta28 Virions
- ● RhDF Rh68.1 Virion

X-axis: CX3C conc. (nM)
Y-axis: Counts, CX3C $^{125}$I

FIG. 7

CMV VACCINES

CROSS-REFERENCE TO RELATED APPLICATIONS

This application claims the benefit of U.S. Provisional Application No. 60/229,365, filed Aug. 30, 2000, which is incorporated herein by reference in its entirety for all purposes.

Related subject matter is described in co-owned U.S. application Ser. No. 09/944,163, filed Aug. 30, 2001, which claims the benefit of U.S. Provisional Application No. 60/228,974, filed Aug. 30, 2000; and in U.S. Provisional Patent Application No. 60/3 16,386, filed Aug. 30, 2001, and in U.S. application Ser. No. 09/944,05 1, filed Aug. 30, 2001, which claims the benefit of U.S. Provisional Patent Application No. 60/229,191 filed Aug. 30, 2000, the disclosures of each of the foregoing applications being incorporated herein by reference in their entirety for all purposes.

BACKGROUND

Human cytomegalovirus (HCMV) is an important human pathogen and a major opportunist which emerges to cause disease in immuno-compromised individuals such as AIDS patients, neonates, and individuals who have been given immunosuppressive drugs as part of a transplantation regimen. In these individuals, the consequences of HCMV in acute or re-emerging infections can be dire, including retinitis, encephalitis, and pneumocystis, among other pathologies. Furthermore, in immuno-competent hosts, HCMV establishes a persistent lifelong infection through which it has been linked to a variety of inflammatory conditions including coronary artery occlusion following heart transplant and arthrectomy and restenosis following angioplasty. Additionally, following infection or reinfection of an immune-competent HCMV sero-negative woman during pregnancy, transmission of virus to the fetus may result in congenital infection of the child with severe physical and/or mental abnormalities resulting.

The genome (230 kb) of HCMV shares certain structural similarities with herpes simplex virus. In particular, HCMV includes a long and short unique region (UL and US, respectively), each of which is flanked by inverted repetitions. The entire HCMV genome has been sequenced (Chee, M. S., et al. (1990) *Curr. Top. Microbiol. Immunol.* 154:125–169) and appears to contain over 200 open reading frames.

One of these open reading frames is referred to as US28, which encodes a protein (also, "US28") that acts as a functional receptor for certain human and viral chemokines (see, e.g., Gao & Murphy, 1994, *J Biol Chem.* 269:28539–42). Upon infection of a cell by CMV, US28 is expressed on the surface of the infected cell and becomes capable of responding to chemokines in the environment. Three other open reading frames called US27, UL33 and UL78 encode for proteins having homology to US28 as shown in Table 1 below.

TABLE 1

Exemplary Viral Chemokine Elements and Immune-inhibitory Genes

| CMV Chemokine Elements or Immune-inhibitory Genes | GenBank Accession No. | Reference |
| --- | --- | --- |
| US27 | X17403 | Chee et al, 1990, Nature, 344:774 |
| US28 | L20501, AF073831-35 | Neote et al, 1993, Cell, 72:415–25 |
| UL33 | X53293 | Chee et al, 1990, Nature, 344:774 |
| UL78 | X17403 | Chee et al, 1990, Nature, 344:774 |

Chemokine receptors such as US28 generally are G protein coupled receptors. Structurally these receptors have seven transmembrane segments that loop in and out of the cell membrane, as well as an intracellular tail that is coupled to a G protein signal transducing molecular complex.

The chemokines themselves constitute a subgroup of a larger class of signaling proteins and have the ability, among other things, to promote cellular migration (Zlotnik et al. (1999) *Crit. Rev. Immunol.* 19:1–47). The chemokines generally are divided into four groups based upon the arrangement of certain cysteine residues within the protein that can form disulfide bonds. One class of chemokines are the beta chemokines which are characterized by having two adjacent cysteines; this structure is referred to in shorthand form simply as CC. The beta chemokines are involved in attraction of monocytes and leukocytes. The alpha chemokines in contrast have a single amino acid separating the two cysteine residues, and thus their structure is designated as CXC. These chemokines are primarily involved in attracting polymorphonuclear cells. The fractalkines constitute a third class of chemokines and tend to be cell bound molecules. The two cysteines in this class are separated by three amino acid residues, a structure designated as CX3C. This class of chemokines are expressed at high levels in the brain; some evidence indicates that the fractalkines are involved in neuron-glial cell interactions (see, e.g., Harrison, et al. (1998) *Proc. Natl. Acad. Sci. U.S.A.* 95:10896–10901; and Nishiyori, A. et al. (1998) *FEBS Lett.* 429:167–172). The structure of the final class of chemokines is simply referred to as C, because these chemokines contain only a single cysteine involved in a disulfide bond. The chemokine receptors have varying specificity for the different classes of chemokines. Some chemokine receptors can bind chemokines from different classes.

The US28 receptor of HCMV is characterized in part by its very strong affinity for fractalkine. It is unclear, however, whether this interaction is involved in the dissemination of the virus from the primary site of infection to other secondary sites. In fact, there is very little known concerning the mechanism by which HCMV is disseminated. Insight into this issue has been hampered primarily by the lack of assay systems, particularly in vivo assay systems, which are good models of viral dissemination in humans. Similarly, the lack of appropriate assay systems has hindered identification of inhibitors effective in reducing the spread of CMV infection.

BRIEF DESCRIPTION OF THE FIGURES

FIG. 1A shows the polynucleotide sequence of the VHL/E US28 coding sequence (SEQ ID NO:3) and FIG. 1B shows the amino acid sequence for the corresponding VHL/E US28 polypeptide (SEQ ID NO:4). The extracellular domain is underlined.

FIGS. 2A–2C present a sequence comparison of the amino acid sequences for human US28 (AD169) (upper sequence; SEQ ID NO:48), rhesus US28.1 (second sequence; SEQ ID NO:6), rhesus US28.2 (third sequence; SEQ ID NO:8), rhesus US28.3 (fourth sequence; SEQ ID NO:10), rhesus US28.4 (fifth sequence; SEQ ID NO:12) and rhesus US28.5 (bottom sequence; SEQ ID NO:14). Regions of sequence similarity are indicated in the boxed regions as determined using the sequence comparison program, SeqVu, from the Garvan Institute, Sydney, Australia. Shaded regions correspond to regions of similar hydrophilicity or hydrophobicity as determined by the SeqVu program.

FIG. 3 is a sequence comparison of the amino acid sequences for human UL78 [strain AD169 (Genebank Accession # X17403, see, e.g., Chee et al., 1990, *Curr. Top. Microbiol. Immunol.* 154:125–169] (upper sequence; SEQ ID NO:16) and rhesus UL78 (lower sequence; SEQ ID NO:18). Regions of sequence similarity are indicated in the boxed regions as determined using the comparision program SeqVu, from the Garvan Institute, Sydney, Australia, with shaded regions corresponding to regions of similar hydrophilicity or hydrophobicity as determined by the same program.

FIGS. 4A and 4B show a sequence comparison of the amino acid sequences for human UL33 [Genebank Accession # X17403; see, e.g., Chee et al., 1990, *Curr. Top. Microbiol. Immunol.* 154:125–169] (upper sequence; SEQ ID NO:20), human UL33 spliced (second sequence; SEQ ID NO:22), rhesus UL33 (third sequence; SEQ ID NO:24) and rhesus UL33 spliced (lower sequence; SEQ ID NO:26). Regions of sequence similarity are indicated in the boxed regions as determined using the comparision program SeqVu, from the Garvan Institute, Sydney, Australia; regions of similar hydrophilicity or hydrophobicity as determined by the same program are shaded.

FIG. 7 is a binding plot showing fractalkine binding to human and rhCMV virions.

SUMMARY

Figure 5:
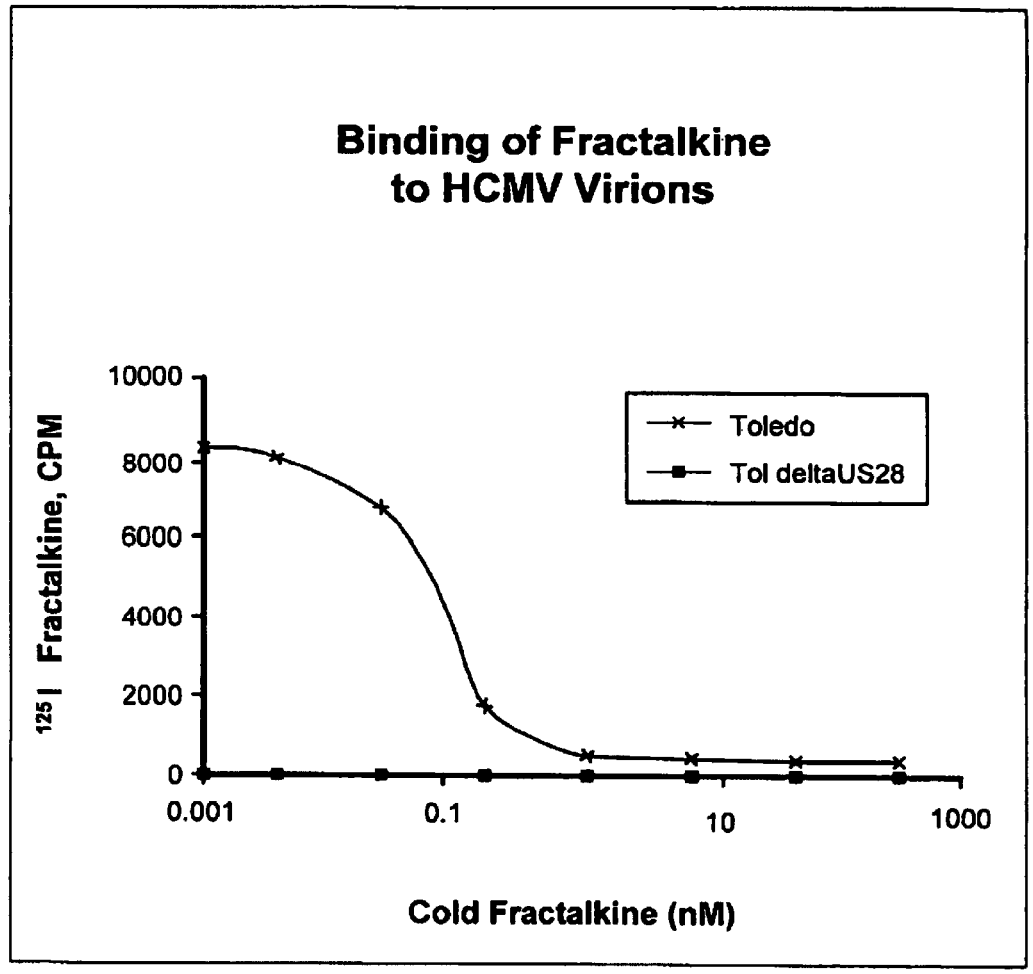
FIG. 5 is a binding plot showing fractalkine binding to human CMV virions.

Provided herein are compositions and prophylactic and therapeutic methods for reducing CMV dissemination in animals, particularly by interfering with the activity, function or expression of US28 or a US28 homolog. Screening methods to identify agents effective in such methods are also disclosed. These screening methods can include both in vitro and in vivo approaches.

The current inventors have unexpectedly found that strains of CMV that infect rhesus monkeys (rhCMV) include multiple open reading frames that encode US28 homologs. A group of five US28 homologs with direct homology to US28 are referred to herein as rhUS28.1, rhUS28.2, rhUS28.3, rhUS28.4 and rhUS28.5. Certain other US28 homologs have homology to the human US28 homologs UL33 and UL78, and thus are referred to as rhUL33 and rhUL78. Still other US28 homologs are splice variants of the foregoing reading frames. One such splice variant is a splice variant of rhUL33 and is referred to as rhUL33 spliced. Collectively, this group of eight exemplary US28 homologs are referred to as rhUS28 homologs.

Thus, isolated and recombinant nucleic acids that encode an entire US28 homolog or a variant or fragment which retains US28 activity are provided herein. More specifically, certain such nucleic acids include isolated, purified or recombinant nucleic acids that encode a protein that is a US28 homolog, wherein the protein has an amino acid sequence at least 75% identical to an amino acid sequence selected from the group consisting of SEQ ID NOS:6, 8, 10, 12, 14, 18, 24 and 26 over a region at least 40 amino acids in length and binds a chemokine. Amino acid sequence identity can be compared, for example, using the BLASTP algorithm with a wordlength (W) of 3 and the BLOSUM62 scoring matrix. Certain nucleic acids encode a protein that has an amino acid sequence selected from the group of SEQ ID NOS:6, 8, 10, 12, 14, 18, 24 and 26. Specific examples of nucleic acids encoding rhUS28 homologs are the nucleic acids with a sequence as set forth in SEQ ID NOS:5, 7, 9, 11, 13, 17, 23 and 25. Other nucleic acids include the foregoing nucleic acids that are operably linked to a promoter.

Also provided are vectors that contain the nucleic acids described herein and cells harboring such vectors.

Isolated proteins or recombinantly produced proteins encoded by rhUS28 homologs, or fragments or variants that retain a US28 activity (e.g., chemokine binding), are also disclosed herein. Certain such proteins include isolated or recombinant proteins comprising an amino acid sequence at least 75% identical to an amino acid sequence as set forth in SEQ ID NOS:6, 8, 10, 12, 14, 18, 24 or 26 over a region at least 40 amino acids in length, wherein the protein binds a chemokine. One example of a program that can be used to compare amino acid sequence identity is the BLASTP algorithm with a wordlength (W) of 3 using the BLOSUM62 scoring matrix. Certain of the proteins provided herein are encoded by a nucleic acid segment that hybridizes under stringent conditions to a nucleic acid having a sequence selected from the group consisting of SEQ ID NOS:5, 7, 9, 11, 13, 17, 23 and 25. Fragments of the full length protein are also provided which retain an activity of US28 (e.g., chemokine binding, such as ability to bind fractalkine). Certain such fragments are isolated proteins comprising at least 12 amino acids from one of the sequences set forth in SEQ ID NOS:6, 8, 10, 12, 14, 18, 24 or 26.

A variety of screening methods for identifying agents that reduce CMV dissemination in various human and non-human animals are also disclosed herein. Certain of these screening methods involve determining whether the agent inhibits the expression or activity of US28 or a US28 homolog, or a fragment or a variant of US28 or the US28 homolog. In some of these methods the US28 homolog is selected from the group consisting of human UL33, human UL33 spliced, human UL78, rhUS28.1, rhUS28.2, rhUS28.3, rhUS28.4, rhUS28.5, rhUL33, rhUL33 spliced and rhUL78.

The screening methods can be conducted in cell-free, cell-based and in vivo formats. Certain in vitro methods involve contacting a chemokine and US28, the US28 homolog, the fragment or the variant, in the presence of a test agent and determining whether the agent inhibits binding between the chemokine and US28, the US28 homolog, the fragment or the variant. Such methods are typically conducted with a CX3C chemokine such as fractalkine or a CC chemokine such as MIP-1α, MIP-1β, MCP-1, eotaxin, vMIP-2 and RANTES. The agent being tested can be of a variety of different types including antibodies that specifically bind to US28, a US28 homolog or variants or fragments of US28 or the US28 homolog or a small molecule.

Cell based screening assays typically involve contacting a cell expressing US28, a US28 homolog, or a fragment or variant of US28 or the US28 homolog, with a chemokine in the presence of a test agent and determining whether the agent inhibits binding between the chemokine and US28, the US28 homolog, the fragment or the variant. The cells in such assays can be infected with CMV or transfected with one of the nucleic acids provided herein which encodes for US28 or a US28 homolog or at least a fragment thereof (e.g., a nucleic acid that encodes at least 10 contiguous amino acids as set forth in SEQ ID NOS:2, 4, 6, 8, 10, 12, 14, 16, 18, 20, 22, 24 or 26).

The finding that rhCMV encodes US28 homologs means that in vivo assays can be conducted using rhesus monkeys. Previously, a good mammal model system for CMV dissemination was unavailable because CMV strains that infect certain other mammals such as rats and mice do not encode US28 homologs. Certain in vivo assays involve administering the agent to a non-human animal infected with CMV and determining whether the agent inhibits the dissemination of CMV from a primary site of infection in the non-human animal. The assays generally are conducted with a rhesus monkey infected with rhCMV.

In addition to the screening methods, a variety of prophylactic and therapeutic treatment methods are provided. These methods can be utilized to treat both human or non-human animals (e.g., rhesus monkeys) infected with CMV or at risk of infection by CMV. In general, the treatment methods typically involve administering to the animal an agent that interferes with the expression or activity of a target nucleic acid encoding US 28 or a US28 homolog. Certain treatment methods involves administering an agent that causes a reduction in expression of the target nucleic acid in cells of the animal. Such reduction can be achieved by administering an antisense nucleic acid that specifically hybridizes to the target nucleic acid or a ribozyme that specifically recognizes the target nucleic acid.

In other treatment methods, the activity of US28 or the US28 homolog is inhibited by administering an agent that inhibits the binding of a ligand to US28 or the US28 homolog. Suitable agents for achieving this include, for example, an antibody that specifically binds to US28 or the US28 homolog or various small molecules.

Pharmaceutical compositions for treating CMV infections either therapeutically or prophylactically are also included. The active ingredients in such compositions can be identified, for example, through the various screening methods described herein. Other compositions are vaccines.

Certain vaccines include an immunogenic CMV polypeptide which is encoded by at least a region of a CMV genome in which the polynucleotide segment encoding US28 or a US28 homolog has been inactivated; and a pharmaceutically acceptable carrier. With some such vaccines, the immunogenic CMV polypeptide is an HCMV polypeptide encoded by at least a region of an HCMV genome in which the polynucleotide segment encoding US28, human UL33 and/or UL78 has been inactivated.

In other vaccines, the immunogenic CMV polypeptide is a rhCMV polypeptide encoded by at least a region of a rhCMV genome in which a polynucleotide segment encoding rhUS28.1, rhUS28.2, rhUS28.3, rhUS28.4, rhUS28.5, rhUL33, or rhUL78 has been inactivated.

DETAILED DESCRIPTION

I. Definitions

As used in this specification and the appended claims, the singular forms "a," "an" and "the" include plural references unless the content clearly dictates otherwise.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

Various biochemical and molecular biology methods are well known in the art. For example, methods of isolation and purification of nucleic acids are described in detail in WO 97/10365, WO 97/27317, Chapter 3 of Laboratory Techniques in Biochemistry and Molecular Biology: Hybridization With Nucleic Acid Probes, Part I. Theory and Nucleic Acid Preparation, (P. Tijssen, ed.) Elsevier, N.Y. (1993); Chapter 3 of Laboratory Techniques in Biochemistry and Molecular Biology: Hybridization With Nucleic Acid Probes, Part 1. Theory and Nucleic Acid Preparation, (P. Tijssen, ed.) Elsevier, N.Y. (1993); and Sambrook et al., Molecular Cloning: A Laboratory Manual, Cold Spring Harbor Press, N.Y., (1989); and Current Protocols in Molecular Biology, (Ausubel, F. M. et al., eds.) John Wiley & Sons, Inc., New York (1987–1999), including supplements such as supplement 46 (April 1999).

As used herein, the following terms have the meanings ascribed to them unless specified otherwise:

As used herein, the term "cytomegalovirus (CMV)" has the normal meaning in the art and refers to one of a family of double stranded DNA viruses of the betaherpes group with positional and genomic similarity to human herpes virus 5 (cytomegalovirus) including, without limitation, human CMV AD169 (ATCC # VR 538), human CMV Towne (ATCC # VR 977), human CMV Davis (ATCC # VR 807), human CMV Toledo (Quinnan et al, 1984, *Ann Intern Med* 101: 478–83), monkey CMV Rh68.1 (ATCC # VR 677), monkey CMV CSG (ATCC # VR 706), rat CMV Priscott (ATCC # VR 991), mouse CMV Smith (ATCC # VR 1399) and others, such as various other mammals, for example. "ATCC" is the American Type Culture Collection, 10801 University Boulevard, Manassas, Va. 20110-2209, USA. The 230-kb dsDNA genome of human and murine CMV were sequenced (see, e.g., Chee et al., 1990, *Curr. Top. Microbiol. Immunol.* 154:125–169; also see Rawlinson, 1996, *J Virol.* 70:8833–49, both incorporated herein in their entirety).

Various open reading frames from human CMV (HCMV) are referred to herein using the nomenclature of Chee et al [e.g., US28, US33, US78 (human US28, human US33, human US78, respectively)]. In general, reference to such reading frames from HCMV also refer to the sequences of sequence and positional homologs of such reading frames found in different HCMV strains, including sequences in any naturally occuring HCMV strain, and mutations to such strains. In some instances the term can also refer to various splice variants not yet characterized in the literature. With respect to the protein, the protein encoded by the HCMV reading frame refers to the protein having a native amino acid sequence, as well as variants and fragments regardless of origin or mode of preparation. Thus, for example, US28, US33 and US78 have the following meanings:

"US28" refers to open reading frame 28 in the unique short region of the genome of human strains of CMV and the protein encoded by this reading frame; while US28 can refer to either the coding region or the corresponding protein, is some instances the term US28 protein or US28 nucleic acid is used for the sake of increased clarity. FIGS. 1A and 1B show the nucleotide and amino acid sequences of US28 from one specific strain, namely CMV strain VHL/E (SEQ ID NOS:3 and 4), respectively; GenBank accession no. L20501)). US28 nucleotide and amino acid sequences from a second human CMV strain, the Toledo strain, are set forth in SEQ ID NOS:1 and 2, respectively. This sequence is the same as US28 from human CMV strain AU4.1 (GenBank accession no. AF073831). The term US28 includes other US28 molecules, e.g., derived from other clinical strains of human CMV, that differ slightly in sequence (see, e.g., GenBank accession nos. AF 073832–35; see also M. S. Chee, et al. (1990) *Curr. Top. Microbiol. Immunol.* 154:125–69).

With respect to the protein, the term US28 refers to a protein having a native US28 amino acid sequence, as well as variants and fragments regardless of origin or mode of preparation. A US28 protein having a native amino acid sequence has the same amino acid sequence as a US28 as obtained from nature (i.e., a naturally occurring US28). The amino acid sequence for US28 from the VHL/E strain shown in FIG. 1B (SEQ ID NO:4) is one specific example of a naturally occurring US28. US28 from the Toledo strain is another example of a protein having a native amino acid sequence (SEQ ID NO:2). Native US28 proteins can be isolated from nature or can be prepared using standard recombinant and/or synthetic methods. A native sequence US28 includes proteins following post-translational modifications such as glycosylation or phosphorylation of certain amino acid residues.

The term "UL33" or "human UL33" refers to open reading frame 33 of the unique long region of the genome of human strains of CMV and proteins encoded by this reading frame. The nucleotide and amino acid sequences for an exemplary UL33 are set forth in SEQ ID NOS:19 and 20, respectively. The term also includes various splice variants. For example, the term can include the splice variant having the nucleotide and amino acid sequences of SEQ ID NOS:21 and 22, respectively. Those of skill can identify other such splice variants using programs designed to identify splice variants such as the "Genefinder", "Genehunt" or "GRAIL" programs available from CMS Molecular Biology.

Similarly the term "UL78" refers to the open reading frame 78 of the unique region of the genome of human strains of CMV and proteins encoded by this reading frame. The nucleotide and amino acid sequences for one exemplary UL78 are set forth in SEQ ID NOS:15 and 16, respectively.

The term "US28 homolog" refers to a nucleic acid or protein that has sequence homology with US28 and at least one activity of US28, typically the ability to bind a chemokine, especially fractalkine. The US28 homolog can be from CMV native to various animals, including various mammals (e.g., human and non-human primates, specifically monkeys, chimpanzee, gorilla, baboon and humans). Thus, US28 homologs can include, but are not limited to, human US27, human UL33, and human UL78. Additional homologs from rhesus monkey (macaca mulatta) CMV can include rhUS28.1, rhUS28.2, rhUS28.3, rhUS28.4, rhUS28.5, rhUL33 and rhUL78.

The terms "nucleic acid" "polynucleotide" and "oligonucleotide" are used interchangable herein and refer to a deoxyribonucleotide or ribonucleotide polymer in either single- or double-stranded form, and unless otherwise limited, encompasses known analogues of natural nucleotides that hybridize to nucleic acids in a manner similar to naturally-occurring nucleotides. Unless otherwise indicated, a particular nucleic acid sequence includes the complementary sequence thereof. A "subsequence" or "segment" refers to a sequence of nucleotides that comprise a part of a longer sequence of nucleotides.

A "primer" is a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14–25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

A "native sequence" refers to the sequence of a naturally occurring nucleic acid or a protein, and includes allelic variants (and proteins encoded thereby) that may occur in nature.

The term "variant" when used in connection with a protein (e.g., US28 or US28 homolog) means proteins that are functional equivalents to a native sequence protein in that the protein has a similar sequence to the native sequence protein and retains, to some extent, one or more of the activities of the native protein. With US28 and the US28 homologs, an activity of the native protein can include, but is not limited to, the ability to bind to chemokines (e.g., fractalkine), immunological cross reactivity with antibodies that specifically bind to a native sequence US28 or US28 homolog (i.e., the fragment competes with the full-length US28); and immunogenicity (e.g., the protein retains an epitope that stimulates B- or T-cell responses against the protein). Preferred functional equivalents retain all of the activities, of the native protein, although the activity of such equivalent proteins can be stronger or weaker when compared on a quantitative basis. Typically, functional equivalents have activities that are within 1% to 10,000% of the activity of a native sequence protein, while other functional equivalents have activities that are 10% to 1000%, or 50% to 500% of that of a native sequence protein.

Variants also include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a protein having a native sequence (see, e.g., Creighton (1984) *Proteins*, W.H. Freeman and Company). In the case of substitutions, the amino acid replacing another amino acid usually has similar structural and/or chemical properties. Insertions and deletions are typically in the range of 1 to 5 amino acids, although depending upon the location of the insertion, more amino acids can be inserted or removed. Variants also include modified forms of a native sequence protein. Modified forms of proteins generally refer to proteins in which one or more amino acids of a native sequence US28 have been altered to a non-naturally occurring amino acid residue. Such modifications can occur during or after translation and include, but are not limited to, phosphorylation, glycosylation, cross-linking, acylation and proteolytic cleavage.

Variants can be prepared using methods known in the art such as site-directed mutagenesis (Carter, et al. (1986) Nucl. Acids Res. 13:4331; Zoller et al. (1987) Nucl. Acids Res. 10:6487), cassette mutagenesis (Wells et al. (1985) Gene 34:315), restriction selection mutagenesis (Wells, et al. (1986) Philos. Trans. R. Soc. London SerA 317:415), and PCR mutagenesis (Sambrook, et al. (1989) Molecular Cloning, Cold Spring Harbor Laboratory Press).

A "fragment" when used in reference to a protein refers to a subsequence of the native protein that retains one or more activities of the native sequence protein. As indicated supra, with respect to US28 and its homologs, such activities include, for example, the ability to bind to chemokines, the ability to bind to an antibody that specifically binds to the full-length US28 or US28 homolog; and immunogenicity.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

A "heterologous sequence" or a "heterologous nucleic acid," as used herein, is one that originates from a source foreign to the particular host cell, or, if from the same source, is modified from its original form. Thus, a heterologous gene in a prokaryotic host cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, that has control elements that are capable of affecting expression of a structural gene that is operably linked to the control elements in hosts compatible with such sequences. Expression cassettes include at least promoters and, optionally, transcription termination signals. Typically, the recombinant expression cassette includes at least a nucleic acid to be transcribed (e.g., a nucleic acid encoding US28 or a US28 homolog) and a promoter. Additional factors necessary or helpful in effecting expression can also be used as described herein. For example, transcription termination signals, enhancers, and other nucleic acid sequences that influence gene expression, can also be included in an expression cassette.

The term "disabled" or "inactivated" as used herein in the context of a gene sequence (e.g., in a CMV genome), refers to a gene that is mutated, deleted or partially deleted in a coding or regulatory (e.g., promoter) sequence, such that the gene product (e.g., protein) that is encoded by the gene is not expressed or is not expressed in biologically active form.

The term "stringent conditions" refers to conditions under which a probe or primer will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. In other instances, stringent conditions are chosen to be about 20° C. or 25° C. below the melting temperature of the sequence and a probe with exact or nearly exact complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel (1987) Methods in Enzymology, vol. 152: Guide to Molecular Cloning Techniques, San Diego: Academic Press, Inc. and Sambrook et al. (1989) Molecular Cloning: A Laboratory Manual, 2nd ed., vols. 1–3, Cold Spring Harbor Laboratory), both incorporated herein by reference. As indicated by standard references, a simple estimate of the $T_m$ value can be calculated by the equation: $T_m=81.5+0.41(\% \text{ G+C})$, when a nucleic acid is in aqueous solution at 1 M NaCl (see e.g., Anderson and Young, "Quantitative Filter Hybridization," in *Nucleic Acid Hybridization* (1985)). Other references include more sophisticated computations which take structural as well as sequence characteristics into account for the calculation of $T_m$. The melting temperature of a hybrid (and thus the conditions for stringent hybridization) is affected by various factors such as the length and nature (DNA, RNA, base composition) of the probe or primer and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook, supra, and Ausubel, supra. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes or primers (e.g., 10 to 50 nucleotides) and at least about 60° C. for long probes or primers (e.g., greater than 50 nucleotides). Stringent conditions can also be achieved with the addition of destabilizing agents such as formamide.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical," in the context of two nucleic acids or polypeptides, refers to two or more sequences or subsequences that have at least 75%, preferably at least 80% or 85%, more preferably at least 90%, 95% or higher nucleotide or amino acid residue identity, when compared and aligned for maximum correspondence, as measured using a sequence comparison algorithm such as those described below for example, or by visual inspection. Preferably, the substantial identity exists over a region of the sequences that is at least about 40–60 nucleotides or amino acids in length, in other instances over a region at least 60–80 nucleotides or amino acids in length, in still other instances at least 90–100 nucleotides or amino acids in length, and in yet other instances the sequences are substantially identical over the full length of the sequences being compared, such as the coding region of a nucleotide for example.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection [see generally, Current Protocols in Molecular Biology, (Ausubel, F. M. et al., eds.) John Wiley & Sons, Inc., New York (1987–1999, including supplements such as supplement 46 (April 1999)]. Use of these programs to conduct sequence comparisons are typically conducted using the default parameters specific for each program.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information. This algorithm involves, first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to" or "specifically hybridizing to", refers to the binding, duplexing, or hybridizing of a molecule only to a particular nucleotide sequence under stringent conditions when that sequence is present in a complex mixture (e.g., total cellular) DNA or RNA.

A further indication that two nucleic acid sequences or polypeptides are substantially identical is that the polypeptide encoded by the first nucleic acid is immunologically cross reactive with the polypeptide encoded by the second nucleic acid, as described below. The phrases "specifically binds to a protein" or "specifically immunoreactive with," when referring to an antibody refers to a binding reaction which is determinative of the presence of the protein in the presence of a heterogeneous population of proteins and other biologics. Thus, under designated immunoassay conditions, a specified antibody binds preferentially to a particular protein and does not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well-known in the art. See, e.g., Creighton (1984) *Proteins*, W.H. Freeman and Company. In addition, individual substitutions, deletions or additions which alter, add or delete a single amino acid or a small percentage of amino acids in an encoded sequence are also "conservatively modified variations."

The term "naturally-occurring" as applied to an object refers to the fact that an object can be found in nature. For example, a polypeptide or polynucleotide sequence that is present in an organism that can be isolated from a source in nature and which has not been intentionally modified by humans in the laboratory is naturally-occurring.

The term "antibody" as used herein includes antibodies obtained from both polyclonal and monoclonal preparations, as well as the following: (i) hybrid (chimeric) antibody molecules (see, for example, Winter et al. (1991) *Nature* 349:293–299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659–2662; and Ehrlich et al. (1980) Biochem 19:4091–4096); (iv) single-chain Fv molecules (sFv) (see, for example, Huston et al. (1988) Proc. Natl. Acad. Sci. USA 85:5879–5883); (v) dimeric and trimeric antibody fragment constructs; (vi) humanized antibody molecules (see, for example, Riechmann et al. (1988) Nature 332:323–327; Verhoeyan et al. (1988) Science 239:1534–1536; and U.K. Patent Publication No. GB 2,276, 169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579–1584; Cumber et al. (1992) J. Immunology 149B:120–126); and, (vii) any functional fragments obtained from such molecules, wherein such fragments retain specific-binding properties of the parent antibody molecule.

The phrases "specifically binds" when referring to a protein, "specifically immunologically cross reactive with," or simply "specifically immunoreactive with" when referring to an antibody, refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule or ligand (e.g., an antibody) that specifically binds to a protein has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, in still other instances $10^8$ $M^{-1}$ to $10^9$ $M^{-1}$, and in yet other instances, about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity.

The term "immunogen" has the normal meaning in the art and refers to a molecule that can elicit an adaptive immune response upon injection into a person or animal, typically a peptide, polypeptide, glyoprotein, lipopolysaccharide or glycosaminoglycan. Thus, the term "immunogenic" refers to the ability of a molecule to elicit an adaptive immune response. An "immunogenic polypeptide" is a polypeptide that is an immunogen.

As used herein, an "immune response" has the ordinary meaning in the art and, unless otherwise specified, refers to an adaptive immune response to a specific antigen. In one aspect, an immune response involves the concerted action of lymphocytes, antigen presenting cells, phagocytic cells, and various soluble macromolecules in defending the body against infection or other exposure to non-self molecules. The immune response can be detected and quantified (e.g., following immunization) by measuring cellular or humoral responses according to numerous assays known in the art (see, e.g., Coligan et al., 1991 (suppl. 1999), CURRENT PROTOCOLS IN IMMUNOLOGY, John Wiley & Sons (hereinafter, sometimes "Coligan")). For example, to detect a cellular immune response, T cell effector effects against cells expressing the antigen are detected using standard assays, e.g., target-cell killing, macrophage activation, B-cell activation or lymphokine production. Humoral responses are measured by detecting the appearance of, or increase in titer of, antigen-specific antibodies; using routine methods such as ELISA. The progress of the antibody response can be determined by measuring class switching (i.e., the switch from an early IgM response to a later IgG response.

The terms "isolated," or "purified" means an object species (e.g., a US28 protein or nucleic acid) has been purified from at least one other species present in a sample obtained from a natural source. In many instances, the terms mean that the object species is the predominant macromolecular species present (i.e., on a molar basis it is more abundant than any other individual species in the composition), and preferably the object species comprises at least about 50 percent (on a molar basis) of all macromolecular species present. Such compositions are said to be "substantially pure." Generally, an isolated, purified or substantially pure US28 protein or nucleic acid will comprise more than 80 to 90 percent of all macromolecular species present in a composition. Most preferably, the object species is purified to essential homogeneity (i.e., contaminant species cannot be detected in the composition by conventional detection methods) wherein the composition consists essentially of a single macromolecular species.

The term "detectably labeled" means that an agent (e.g., a probe) has been conjugated with a label that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "epitope" generally refers to that portion of an antigen that interacts with an antibody. More specifically, the term epitope includes any protein determinant capable of specific binding to an immunoglobulin or T-cell receptor. Specific binding exists when the dissociation constant for antibody binding to an antigen is $\leq 1$ µM, preferably $\leq 100$ nM and most preferably $\leq 1$ nM. Epitopic determinants usually consist of chemically active surface groupings of molecules such as amino acids and typically have specific three-dimensional structural characteristics, as well as specific charge characteristics.

The term "patient" includes human and veterinary subjects.

II. General

Compositions and methods for treating or preventing viral dissemination from cytomegalovirus (CMV) infection are described herein. As indicated supra, as used herein the term "CMV" includes various strains of the virus that infect different animals, including various mammals such as humans and monkeys for example. Strains of CMV that infect humans are referred to as human CMV or simply HCMV. As described in the Background section, the HCMV genome contains an open reading frame designated US28, which encodes a receptor that binds certain human and viral chemokines.

The current inventors have unexpectedly found that the CMV strain that infects monkeys, specifically rhesus monkeys (i.e., rhCMV), includes several US28 homologs. This finding was unexpected for several reasons. First, the genome of CMV strains that infect various other mammals such as mice and rats lack a region encoding for a US28 homolog. Given this absence, one could not have predicted with any degree of certainty that the CMV strain that infects other animals such as monkeys would contain an open reading frame for a US28 homolog. Secondly, in HCMV there appears to be a limited number of proteins related to US28 (e.g., US27, UL33, and UL78). In contrast, rhCMV contains at least five US28 homologs, which the inventors refer to as rhUS28.1, rhUS28.2, rhUS28.3, rhUS28.4, rhUS28.5. Furthermore, the genome of rhCMV contains homologs of UL33 (i.e., rhUL33) and UL78 (i.e., rhUL78). In addition to the unexpectedly large number of US28 homologs in the rhCMV genome, it was also unexpected that as a group these various homologs would have relatively low homology (see Table 2A). Homolgy of other US28 homologs are shown in Table 2B. There is 29 percent identity between CMV (AD169) UL78 and the rhesus CMV (Rh68.1) UL78 homolog.

TABLE 2A

Percent identity of human CMV (Toledo) US28 and rhesus CMV (Rh68.1) US28 homologs.

| RhUS28.1 | RhUS28.2 | RhUS28.3 | RhUS28.4 | RhUS28.5 | |
|---|---|---|---|---|---|
| 21 | 19 | 20 | 21 | 34 | Toledo |
|  | 36 | 37 | 16 | 18 | RhUS28.1 |
|  |  | 33 | 15 | 16 | RhUS28.2 |
|  |  |  | 15 | 20 | RhUS28.3 |
|  |  |  |  | 18 | RhUS28.4 |

TABLE 2B

Percen: identity of human CMV (AD169) UL33 and rhesus CMV (Rh68.1) UL33 homologs, and exemplary splice variants.

| Human UL33 splice | RhUL33 | RhUL33 splice | |
|---|---|---|---|
| 100 | 53.5 | 52.3 | Human UL33 |
|  | 53.5 | 51.2 | Human UL33 splice |
|  |  | 100 | RhUL33 |

The US28 homologs (both the genes and corresponding proteins) disclosed herein can be utilized in the development of a variety of in vitro and in vivo assays to study CMV pathology and mechanisms of viral dissemination. The absence of a non-human in vivo model system has meant that investigations of CMV have been limited only to in vitro systems. Thus, the finding that rhCMV encodes US28 homologs is an important advance because it means that studies regarding modes of viral infection and dissemination can be performed using an in vivo model system which heretofore was not possible. The assays provided herein can be utilized to identify new agents that can inhibit the dissemination of viruses such as CMV. Such agents can subsequently be formulated as a pharmaceutical composition and used in the prophylactic and/or therapeutic treatment of CMV infections. The in vivo system also means that one can rationally design and test CMV vaccines by inactivation or removal of segments of the viral genome thought to be involved in viral dissemination followed by a determination of the effect of such inactivation or removal on viral dissemination. Thus, vaccines against CMV and methods for making such vaccines are also disclosed.

Further studies described herein have also demonstrated that HCMV virions (viral particles) express US28 on their surface and that rhCMV virions likewise express one or more US28 homologs on their surface. This finding has important implications regarding viral dissemination given that US28 and US28 homologs bind certain chemokines. In particular, the virus could be transported to, or become anchored at, different locations in the body by attachment to chemokines. Thus, for example, CMV in the blood could become attached to a cell expressing a chemokine such as fractalkine.

III. US28 Homologs—Nucleic Acids

The present inventors have identified a number of segments (open reading frames) of the rhCMV genome that encode US28 homologs; these homologs are referred to herein as rhUS28.1, rhUS28.2, rhUS28.3, rhUS28.4 and rhUS28.5. Other US28 homologs contained in the rhCMV genome are related to human UL33 and UL78 and thus are referred to as rhUL33 and rhUL78, respectively. Certain other homologs are splice variants of the foregoing. For example, various nucleic acids are splice variants of rhUL33. One such variant is referred to herein as rhUL33 spliced. Collectively, these eight nucleic acid sequences are referred to herein for the sake of simplicity as "rhesus US28 homologs." Thus, isolated and/or recombinant nucleic acids that encode the entire length of one of the rhesus US28 homologs or a fragment or variant retaining US28 activity are provided herein. Table 3 below lists the various rhesus CMV homologs and the corresponding nucleotide and protein sequences.

TABLE 3

Sequence Identifiers for rhCMV Homologs

| rhCMV Homolog | Nucleotide Sequence | Amino Acid Sequence |
| --- | --- | --- |
| rhUS28.1 | SEQ ID NO:5 | SEQ ID NO:6 |
| rhUS28.2 | SEQ ID NO:7 | SEQ ID NO:8 |
| rhUS28.3 | SEQ ID NO:9 | SEQ ID NO:10 |
| rhUS2S.4 | SEQ ID NO:11 | SEQ ID NO:12 |
| rhUS28.5 | SEQ ID NO:13 | SEQ ID NO:14 |
| rhUL78 | SEQ ID NO:17 | SEQ ID NO:18 |
| rhUL33 | SEQ ID NO:23 | SEQ ID NO:24 |
| rhUL33 spliced | SEQ ID NO:25 | SEQ ID NO:26 |

As described in greater detail below in Example 2, these sequences were identified by sequencing the entire rhCMV genome and then analyzing the resulting sequence for segments having homology to human US28 using the BLAST X program, as well as the BioNavigator bio-informatic program set (see Example 2 for additional details) The BioNavigator service is provided by Entigen of Sunnyvale, Calif.

Although the degree of identity between certain of the homologs is not particularly high, there are several factors that indicate that the US28 homologs encode proteins having US28 activity. First, as shown in FIGS. 2A–2C and FIGS. 4A and 4B, rhUS25 homologs show a relatively high level of similarity with US28 or one of the corresponding human homologs of US28 (e.g., UL33 or UL78). In particular, there is significant similarity in hydrophobicity/hydrophilicity alignments. The various rhUS28 homologs have hydrophobic and hydrophilic regions consistent with the class of 7 member G proteins of which US28 is a member. Additionally, the rhUS28 homologs have positional homology with US28.

The rhesus US28 homologs can include naturally occurring, synthetic, and intentionally manipulated polynucleotide sequences (e.g., site directed mutagenesis or use of alternate promoters for RNA transcription). The polynucleotide sequence for the rhesus US28 homologs includes antisense sequences, as well as sequences that are degenerate as a result of the degeneracy of the genetic code.

Hence, the nucleic acids encoding the various rhesus US28 homologs includes each of the nucleotide sequences as set forth in Table 3 and nucleic acid sequences complementary to those sequences. Also included are subsequences of the above-described nucleic acid sequences. Such subsequences include, for example, those that are at least 12, 13, 14, 15, 16, 17, 18, 19, 20, 21, 22, 23, 24, or 25 nucleotides in length and which specifically hybridize to a nucleic acid that encodes one of the rhesus US28 homologs. Other fragments are longer, such as at least 30, 35, 40, 45, 50, 55, 60, or 65 nucleotides in length.

Thus, also provided herein are isolated or recombinant nucleic acid molecules comprising a nucleotide sequence selected from the group consisting of (a) a deoxyribonucleotide sequence complementary to one of the rhesus US28 homologs; (b) a ribonucleotide sequence complementary to one of the rhesus US28 homologs; (c) a nucleotide sequence complementary to the deoxyribonucleotide sequence of (a) or to the ribonucleotide sequence of (b); (d) a nucleotide sequence of at least 25 consecutive nucleotides capable of hybridizing to one of the rhesus US28 homologs; and (e) a nucleotide sequence capable of hybridizing to a nucleotide sequence of (d), wherein the nucleotide sequences for the rhesus US28 homologs are as indicated in Table 3.

Nucleic acid molecules that include a nucleotide sequence that encodes a polypeptide having an amino acid sequence that is substantially identical to the amino acid sequence of one of the rhesus US28 homologs are also provided (see Table 3). For example, the invention includes a nucleotide sequence that encodes a polypeptide having an amino sequence that is at least 75% identical to the amino acid sequence for one of the rhesus US28 homologs over a region of at least 40 amino acids in length. In other instances, the polypeptide encoded by the rhesus US28 homolog is at least 80, 82, 84, 86, 88 or 90% identical to the amino acid sequence of one of the rhesus US28 homologs; in still other instances, the polypeptide is at least 90% (e.g., 92 or 94%) or at least 95% (e.g., 96 or 98%) identical to the amino acid sequence of one of the rhesus US28 homologs over a region of at least 40 amino acids. In some instances, the region of percent identity extends over a region of 50, 55, 60, 65, 70, 75, 80, 85, 90, 95 or 100 amino acids, and can extend over the full length of the amino acid sequence as shown in SEQ ID NOS:6, 8, 10, 12, 14, 18, 24 and 26. Sequence comparisons of the protein encoded by the nucleic acids of the invention can be performed visually or with a comparison algorithm. One such algorithm is the BLASTP algorithm using a wordlength (W) of 3 and the BLOSUM62 scoring matrix.

The polynucleotide sequences are typically substantially identical to one of the rhesus US28 homologs having a sequence as listed in Table 3 (i.e., SEQ ID NOS:5, 7, 9, 11, 13, 17, 23 and 25). For example, certain nucleic acids are at least 75% identical to the nucleic acid one of the rhesus US28 homologs over a region of at least 50 nucleotides in length. Other nucleic acids are at least 80, 82, 84, 86, 88 or 90% identical to the nucleic acid sequence of one of the rhesus US28 homologs of Table 3. Certain nucleic acids are at least 90% (e.g., 92 or 94%) or at least 95% (e.g., 96 or 98%) identical to the nucleic acid sequences of one of the rhesus US28 homologs listed in Table 3 over a region of at least 50 amino acids. In some instances, the region of percent identity extends over a longer region than 50 nucleotides, such as 75, 100, 125, 150, 175, 200, 225 or 250 nucleotides, or over the full length of the encoding region.

As noted supra, the rhUS28 homologs can include splice variants of the various open reading frames. A spliced variant form can be predicted by use of splice acceptor/donor site prediction programs commonly available to those skilled in the art, such as the "Genefinder", "Genehunt" or "GRAIL" programs available at the CMS Molecular Biology resource found at www.unl.edu. With such programs various spliced variants of a core sequence car be elucidated, and splicing at the N terminus of chemokine receptors such as the rhUL28 homologs is not uncommon.

One example of such a splice variant is a splice variant of rhUL33, which is referred to herein as rhUL33 spliced (SEQ ID NO:25). This particular splice variant can be described with reference to the nucleotide sequence set forth in SEQ ID NO:27 which is a segment that extends roughly 1000 nucleotides upstream of the rhUL33 reading frame and roughly a couple hundred nucleotides downstream. Assigning the first nucleotide of this sequence as nucleotide 1, with this particular splice variant, translation is initiated at nucleotide 603 through nucleotide 752, exon 1. An intron spanning nucleotide 753 to 830 is removed and exon 1 is joined to exon 2, nucleotide 831 to 2006. In contrast the unspliced gene runs through nucletotide 1017 to 2006 in this sequence.

To identify nucleic acids encoding one of the rhesus US28 homologs, one can employ a nucleotide sequence comparison algorithm such as are known to those of skill in the art. For example, one can use the BLASTN algorithm. Suitable parameters for use in BLASTN are wordlength (W) of 11, M=5 and N=−4. Specific examples of nucleic acids which are provided herein include the nucleotide sequences as set forth in SEQ ID NOS:5, 7, 9, 11, 13, 17, 23 and 25.

Alternatively, one can identify a rhesus US28 homolog nucleic acid by hybridizing, under stringent conditions, the nucleic acid of interest to one of the rhesus US28 homologs as set forth in one of the following sequences, SEQ ID NOS: 5, 7, 9, 11, 13, 17, 23 and 25. Also provided are nucleic acids that encode a protein that is immunologically cross reactive with one of the rhesus US28 homologs or some fragment or variant thereof.

In one embodiment, a rhesus US28 homolog is isolated by routine cloning methods. The nucleotide sequence of a gene or cDNA encoding one of the rhesus US28 homologs, is used to design probes that specifically hybridize to a rhesus US28 homolog cDNA in a cDNA library, a rhesus US28 homolog gene in a genomic DNA sample, or to a rhesus US28 homolog mRNA in a total RNA sample (e.g., in a Southern or Northern blot). Once the target nucleic acid is identified, it can be isolated according to standard methods known to those of skill in the art.

Rhesus US28 homologs can also be cloned using well-known amplification techniques. Examples of protocols sufficient to direct persons of skill through in vitro amplification methods, include: (i) the polymerase chain reaction (PCR), (ii) the ligase chain reaction (LCR), (iii) Qβ-replicase amplification, and (iv) other RNA polymerase mediated techniques, are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem*. 35: 1826; Landegren et al. (1988) *Science* 241: 1077–1080; Van Brunt (1990) *Biotechnology* 8: 291–294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426, 039.

Suitable primers for use in the amplification of the rhesus US28 homologs include, for example, those shown in Table 4 below:

TABLE 4

Primer sequences for amplifying rhUS28 homologs.

| rhUS28 Homolog | Primer Sequence (Upper Strand) | SEQ ID NO: | Primer Sequence (Lower Strand) | SEQ ID NO: |
|---|---|---|---|---|
| rhUS28.1 | TATGAATAACACATCTTGCAACTTC | 28 | CACACAGACCACATGTAC | 29 |
| rhUS28.2 | ATTCAACATGACCAACGCCGG | 30 | GCATTTCCGTGGATTCG | 31 |
| rhUS28.3 | CATGACCAACACTAAC | 32 | GAGTCTTTTGTGAGCC | 33 |
| rhUS28.4 | TATGAATTCGAGCCAGCAC | 34 | GTACGCGACTAAGACAGAG | 35 |
| rhUS28.5 | AAAGATGACTACCACCAC | 36 | ATAACCTAGCACCTCCCC | 37 |
| rhUL78 | CTGAAACCATGATTACGG | 38 | CACGCAGCACAAGAGCAC | 39 |
| rhUL33 | CATGACCAATCTTTACTC | 40 | GTGTCGCCACTCCTACCC | 41 |
| rhUL33 spliced | AAGTTAGTGATGGCAGTC | 42 | GTATGTAAACCCGTGGAG | 43 |

The foregoing nucleic acids can be obtained by any suitable method known in the art, including, for example, 1) hybridization of genomic or cDNA libraries with probes to detect homologous nucleotide sequences; 2) antibody screening of expression libraries to detect cloned DNA fragments with shared structural features; 3) various amplification procedures such as polymerase chain reaction (PCR) using primers capable of annealing to the nucleic acid of interest; and 4) direct chemical synthesis.

As an alternative to cloning one of the rhesus US28 homologs, a suitable nucleic acid can be chemically synthesized. Direct chemical synthesis methods include, for example, the phosphotriester method of Narang et al. (1979) *Meth. Enzymol*. 68: 90–99; the phosphodiester method of Brown et al. (1979) *Meth. Enzymol*. 68: 109–151; the diethylphosphoramidite method of Beaucage et al. (1981) *Tetra. Lett*., 22: 1859–1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences can be obtained by the ligation of shorter sequences. Alternatively, subsequences can be cloned and the appropriate subsequences cleaved using appropriate restriction enzymes. The fragments can then be ligated to produce the desired DNA sequence.

In certain methods that utilize rhesus US28 homologs, it may be desirable to modify the nucleotide sequence. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81–97, Roberts et al. (1987) *Nature* 328: 731–734.

IV. Rhesus US28 Homologs—Proteins

A. Protein Composition

Proteins encoded by the foregoing rhesus US28 homologs are also provided. More specifically, such proteins are include rhesus US28 homologs that are isolated from natural sources, and/or prepared according to recombinant methods, and/or prepared by chemical synthesis, and/or using a combination of recombinant methods and chemical synthesis. The various US28 homologs are exemplified by the amino acid of SEQ ID NOS:6, 8, 10, 12, 14, 18, 24 and 26. Further provided are fragments and variants of these exemplary sequences.

Also included are isolated proteins having an amino acid sequence at least about 75% identical to an amino acid sequence of one of the rhesus US28 homologs. Generally, such proteins are at least 80, 82, 84, 86, 88 or 90% identical; other proteins are at least 90, 91, 92, 93, 94 or 95% identical to the amino acid sequence of one of the rhesus US28 homologs. The region of similarity between one of the rhesus US28 homologs and a related protein typically extends over a region of at least 40 amino acids in length, in other instances over a longer region than 40 amino acids such as 50, 55, 60, 65, 70, 75, 80, 85, 90, 95 or 100 amino acids, and most preferably over the full length of the protein. One example of an algorithm that is useful for comparing a polypeptide to the amino acid sequence of US28 or a US28 homolog is the BLASTP algorithm; suitable parameters include a word length (W) of 3, and a BLOSUM62 scoring matrix.

Besides substantially full-length proteins, fragments of such proteins having biological activity are provided. Biological activity can include the ability to bind a chemokine, particularly a CX3C chemokine such as fractalkine, as well as other chemokines such as CC chemckines. Other examples of significant biological activity include antibody binding (e.g., the fragment competes with a full-length rhesus US28 homolog such as set forth in SEQ ID NOS:6, 8, 10, 12, 14, 18, 24 and 26) and immunogenicity (e.g., possession of epitopes that stimulate B- or T-cell responses against the fragment).

As alluded to supra, protein fragments are also provided herein. Such fragments typically include at least 5, 6, 7, 8, 9, or 10 contiguous amino acids; other fragments are somewhat longer and include at least 12, 13, 14, 15, 16, 17, 18, 19 or 20 contiguous amino acids. Certain fragments are still longer yet such as at least 25, 30, 40, 50, 60, 70, 80, 90 or 100 contiguous amino acids.

The proteins described herein also include particular regions or domains of the rhesus US28 homologs. The rhesus US28 homologs are typically encoded by nucleotide sequences that are substantially identical with the nucleotide sequences as set forth in SEQ ID NOS:5, 7, 9, 11, 13, 17, 23 and 25. The nucleotides encoding the rhesus US28 homologs will also typically hybridize to a polynucleotide sequence as set forth in SEQ ID NOS: 5, 7, 9, 11, 13, 17, 23 and 25.

Often the rhesus US28 proteins will share at least one antigenic determinant in common with at least one of the amino acid sequences set forth in SEQ ID NOS:6, 8, 10, 12, 14, 18, 24 and 26. The existence of such a common determinant is evidenced by cross-reactivity of the variant protein with an antibody prepared against rhesus US28 homolog. Cross-reactivity can be tested using polyclonal sera against the rhesus US28 homolog, but can also be tested using one or more monoclonal antibodies against a rhesus US28 homolog.

The proteins provided herein include modified protein backbones. Illustrative examples of such modifications include chemical derivatizations of proteins, such as acetylations and carboxylations. Modifications also include glycosylation modifications and processing variants of a typical polypeptide. Such processing steps specifically include enzymatic modifications, such as ubiquitinization and phosphorylation. See, e.g., Hershko & Ciechanover, *Ann. Rev. Biochem*. 51:335–364 (1982).

B. Production of US28 Homolog Protein

1. Recombinant Technologies

Proteins encoded by US28 and US28 homologs (e.g., SEQ ID NOS: 6, 8, 10, 12, 14, 18, 24 and 26) or fragments thereof can be prepared by recombinant means by expressing the proteins in host cells transfected with a vector in which the coding sequence for US28 or the US28 homolog is operably linked to an expression control sequence in an expression vector. Expression vectors are typically replicable in the host organisms either as episomes or as an integral part of the host chromosomal DNA. Commonly, expression vectors contain selection markers, e.g., tetracycline resistance or hygromycin resistance, to permit detection and/or selection of those cells transformed with the desired DNA sequences (see, e.g., U.S. Pat. No. 4,704,362).

Typically, the coding region for US28 or US28 homolog is placed under the control of a promoter that is functional in the desired host cell to produce relatively large quantities of the protein. An extremely wide variety of promoters are well-known, and can be used in the expression vectors provided herein, depending on the particular application. Ordinarily, the promoter selected depends upon the cell in which the promoter is to be active. Other expression control sequences such as ribosome binding sites, transcription termination sites and the like are also optionally included. Constructs that include one or more of such control sequences are termed "expression cassettes." Accordingly, provided herein are expression cassettes into which nucleic acids encoding US28 or US28 homologs are incorporated for high level expression of the corresponding protein in a desired host cell.

In certain instances, the expression cassettes are useful for expression of polypeptides in prokaryotic host cells. Commonly used prokaryotic control sequences (defined herein to include promoters for transcription initiation, optionally with an operator, along with ribosorne binding site sequences) include such commonly used promoters as the beta-lactamase (penicillinase) and lactose (lac) promoter systems (Change et al. (1977) *Nature* 198: 1056), the tryptophan (trp) promoter system (Goeddel et al. (1980) *Nucleic Acids Res*. 8: 4057), the tac promoter (DeBoer et al. (1983) *Proc. Natl. Acad. Sci. U.S.A.* 80:21–25); and the lambda-derived $P_L$ promoter and N-gene ribosome binding site (Shimatake et al. (1981) *Nature* 292: 128). In general, however, any available promoter that functions in prokaryotes can be used.

For expression of polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in Bacillus in addition to *E. coli*.

For expression of the polypeptides in yeast, convenient promoters include GAL1-10 (Johnson and Davies (1984) *Mol. Cell. Biol.* 4:1440–1448) ADH2 (Russell et al. (1983) *J. Biol. Chem.* 258:2674–2682), PHO5 (*EMBO J.* (1982) 6:675–680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209). Another suitable promoter for use in yeast is the ADH2/GAPDH hybrid promoter as described in Cousens et al., *Gene* 61:265–275 (1987). Other promoters suitable for use in eukaryotic host cells are well-known to those of skill in the art.

For expression of the polypeptides in mammalian cells, convenient promoters include CMV promoter (Miller, et al., *BioTechniques* 7:980), SV40 promoter (de la Luma, et al.,(1998) *Gene* 62:121), RSV promoter (Yates, et al, (1985) *Nature* 313:812), and MMTV promoter (Lee, et al.,(1981) *Nature* 294:228).

For expression of the polypeptides in insect cells, the convenient promoter is from the baculovirus *Autographa californica* nuclear polyhedrosis virus (NcMNPV) (Kitts, et al., (1993) *Nucleic Acids Research* 18:5667).

Either constitutive or regulated promoters can be used in the expression systems. Regulated promoters can be advantageous because the host cells can be grown to high densities before expression of the polypeptides is induced. High level expression of heterologous proteins slows cell growth in some situations. For *E. coli* and other bacterial host cells, inducible promoters include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074–8). These promoters and their use are discussed in Sambrook et al., *Molecular Cloning: A Laboratory Manual*, Cold Spring Harbor Press, N.Y., (1989). Inducible promoters for other organisms are also well-known to those of skill in the art. These include, for example, the arabinose promoter, the lacZ promoter, the metallothionein promoter, and the heat shock promoter, as well as many others.

Construction of suitable vectors containing one or more of the above listed components employs standard ligation. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. A wide variety of cloning and in vitro amplification methods suitable for the construction of recombinant nucleic acids is described, for example, in Berger and Kimmel, *Guide to Molecular Cloning Techniques, Methods in Enzymology*, Volume 152, Academic Press, Inc., San Diego, Calif. (Berger); and "Current Protocols in Molecular Biology," F. M. Ausubel et al., eds., *Current Protocols*, a joint venture between Greene Publishing Associates, Inc. and John Wiley & Sons, Inc., (1998 Supplement) (Ausubel).

There are a variety of suitable vectors suitable for use as starting materials for constructing the expression vectors containing the nucleic acids encoding US28 or US28 homolog. For cloning in bacteria, common vectors include pBR322-derived vectors such as PBLUESCRIPT™, pUC18/19, and λ-phage derived vectors. In yeast, suitable vectors include Yeast Integrating plasmids (e.g., YIp5) and Yeast Replicating plasmids (the YRp series plasmids) pYES series and pGPD-2 for example. Expression in mammalian cells can be achieved, for example, using a variety of commonly available plasmids, including pSV2, pBC12BI, and p91023, pCDNA series, pCMV1, pMAMneo, as well as lytic virus vectors (e.g., vaccinia virus, adenovirus), episomal virus vectors (e.g., bovine papillomavirus), and retroviral vectors (e.g., murine retroviruses). Expression in insect cells can be achieved using a variety of baculovirus vectors, including pFastBac1, pFastBacHT series, pBluesBac4.5, pBluesBacHis series, pMelBac series, and pVL1392/1393, for example.

The polypeptides encoded by the full-length genes or fragments thereof for US28 or US28 homolog can be expressed in a variety of host cells, including *E. coli*, other bacterial hosts, yeast, and various higher eukaryotic cells such as the COS, CHO, HeLa and myeloma cell lines;. The host cells can be mammalian cells, plant cells, insect cells or microorganisms, such as, for example, yeast cells, bacterial cells, or fungal cells. Examples of useful bacteria include, but are not limited to, *Escherichia, Enterobacter, Azotobacter, Erwinia, Klebsielia*.

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, *Protein Purification*, Springer-Verlag, N.Y. (1982), Deutscher, *Methods in Enzymology Vol.* 182: *Guide to Protein Purification*., Academic Press, Inc. N.Y. (1990)). Typically the polypeptides are purified to obtain substantially pure compositions of at least about 90 to 95% homogeneity; in other applications, the polypeptides are further purified to at least 98 to 99% or more homogeneity. To facilitate purification, the nucleic acids that encode the US28 or US28 polypeptide can be linked to a coding sequence for an epitope or "tag" for which an affinity binding reagent is available.

2. Non-Recombinant Methods

Alternatively, the polypeptides encoded by US28 or US28 homologs or fragments thereof can be synthesized by chemical methods or produced by in vitro translation systems using a pclynucleotide template to direct translation. Methods for chemical synthesis of polypeptides and in vitro translation are well-known in the art, and are described further by Berger & Kimmel, *Methods in Enzymology, Volume* 152, *Guide to Molecular Cloning Techniques*, Academic Press, Inc., San Diego, Calif., 1987 (incorporated by reference in its entirety).

V. Methods of Inhibiting CMV Dissemination

A. General

A variety of methods are provided herein for treating CMV infections by inhibiting the expression or function of US28 or US28 homolog; such treatments can reduce the extent or rapicity of CMV dissemination in an animal (e.g., a mammal, including, for example, a primate such as a human or a non-human primate such as an ape, monkey or chimpanzee). Several illustrative embodiments are described in the sections that follow. While the following examples are directed to methods of treating infections caused by HCMV and rhCMV, it should be understood that similar approaches could be taken in the treatment of other animals that are infected by CMV strains that contain a US28 homolog.

The methods typically utilize an agent that interferes with the function or expression of US28 or a US28 homolog such that viral dissemination during acute or re-emerging CMV infection and/or reactivation from latency is inhibited. As used herein, "dissemination" refers to a detectable increase in viral titer or amount at sites other than the site of primary infection (inoculation), e.g., by transmission of virus from sites of primary infection or reactivation to secondary sites (e.g., tissues or organs).

Virus dissemination typically involves transmission of virus from sites of primary infection (e.g. mucosal tissues such as oral or genital mucosal endothelia) or reactivation (e.g. blood leukocytes including myeloid progenitor cells in the bone marrow and peripheral blood monocytes) to secondary sites (e.g. tissues or organs including salivary glands, kidney, spleen, liver and lungs) where viral replication and amplification may occur. Dissemination is thought to be linked to the binding of US28 to various chemokines. For example, US28 has been shown to bind a variety of human, murine, and virus-encoded CC chemokines in a variety of assay formats (Kledal et al., 1997, *Science* 277:1656–9; Kuhn et al., 1995, *Biochem Biophys Res Commun.* 211:325–30). In addition, the CX3C chemokine, fractalkine, binds with a very high affinity ($K_f$~50 pM) to US28 (Kledal et al., 1998, *FEBS Lett.* 441:209–14).

Thus, without intending to be bound by a particular mechanism, dissemination may involve assisted movement of virus from primary sites (e.g. by random or directed migration of infected cells), release of virus into the bloodstream and random or directed attachment of this virus to cells at secondary sites, or other modes. For instance, fractalkine is expressed on certain endothelial cell surfaces (e.g., vascular endothelial cells) and on populations of dendritic cells (DC), and may thus define a portal through which CMV infected cells or virions go from the circulation to the tissue space, as well as find residence in the DC. Expression of fractalkine on limited cell types can result in the formation of a solid phase chemotactic gradient. Cells infected with CMV and thus expressing US28 may then move along this gradient to tissues important in pathogenesis, immunity and latency.

As discussed briefly above, the current inventors have also established that CMV virions (both human and rhesus strains of the virus) express US28 or US28 homolog. Consequently, the virus could be transported through a circulatory system in the body and become anchored at a secondary site via binding to a chemokine located at a cell surface.

B. Inhibition of US28 Protein Expression

One general approach of the treatment methods provided herein is to reduce CMV dissemination by interfering with the expression of the US28 gene product (i.e., RNA or protein). Various techniques can be utilized to achieve this goal, including administering antisense nucleic acids and ribozymes. These methods are discussed in turn in the following sections.

1. Antisense

In certain treatment methods, antisense polynucleotides that specifically hybridize to a segment of US28 coding sequence or the US28 homolog coding sequence are administered to inhibit expression of US28 or the US28 homolog in an animal infected with CMV, or the antisense polynucleotide is administered prophylactically to an animal susceptible to infection with CMV. Methods relating to antisense polynucleotides are well known, see e.g., Melton, D., Ed, 1988, ANTISENSE RNA AND DNA, Cold Spring Harbor Laboratory, Cold Spring Harbor, N.Y.; Dagle et al., 1991, *Nucleic Acids Research*, 19:1805; and Uhlmann et al., *Chem. Reviews*, 90:543–584 (1990).

Typically, the antisense polynucleotides used in the methods comprise an antisense sequence of typically at least about 10 contiguous nucleotides, in other instances at least 12 or 14 contiguous nucleotides, and in still other instances up to about 100 contiguous nucleotides that specifically hybridize to a sequence from a mRNA encoding US28 or a US28 homolog in the target organism. Thus, in the treatment of infections caused by human strains of CMV, appropriate polynucleotides sequences can be prepared based upon the nucleotide sequence for human US28 as set forth in SEQ ID NO:3 (FIG. 1A) and for human UL33 (SEQ ID NO:19), human UL33 spliced (SEQ ID NO:21) and human UL78 (SEQ ID NO:15). Likewise, in the treatment of infections caused by rhesus strains, appropriate polynucleotides can be prepared based upon the nucleotide sequences for the various rhesus US28 homologs as shown in SEQ ID NOS:5, 7, 9, 11, 13, 17, 23 and 25.

In general, the antisense polynucleotide should be long enough to form a stable duplex but short enough, depending on the mode of delivery, to be administered in vivo, if desired. The minimum length of a polynucleotide required for specific hybridization to a target sequence depends on several factors, such as G/C content, positioning of mismatched bases, (if any), degree of uniqueness of the sequence as compared to the population of target polynucleotides, and chemical nature of the polynucleotide (e.g., methylphosphonate backbone, peptide nucleic acid, phosphorothioate), among other factors.

In some instances, the antisense sequence is complementary to relatively accessible sequences of the US28 mRNA or the US28 homolog mRNA (e.g., relatively devoid of secondary structure). This can be determined by analyzing predicted RNA secondary structures using, for example, the MFOLD program (Genetics Computer Group, Madison, Wis.) and testing in vitro or in vivo as is known in the art. Another useful method for optimizing antisense compositions uses combinatorial arrays of oligonucleotides (see, e.g., Milner et al., 1997, *Nature Biotechnology* 15:537).

The antisense nucleic acids (DNA, RNA, modified, analogues, and the like) can be made using any suitable method for producing a nucleic acid, such as the chemical synthesis and recombinant methods. Specific methods for preparing such sequences are referenced supra in the section on rhesus US28 nucleic acids.

2. Ribozymes

Ribozymes are also useful for inhibiting US28 or US28 homolog activity in an animal. Useful ribozymes can comprise 5'- and 3'-terminal sequences complementary to the US28 mRNA or US28 homolog mRNA and can be engineered by one of skill on the basis of the US28 mRNA sequence (see, e.g., SEQ ID NO:3; see FIG. 1A) and US28 homolog sequences disclosed herein (SEQ ID NOS:5, 7, 9, 11, 13, 17, 23 and 25). Ribozymes that can be utilized in the treatment methods include those having characteristics of group I intron ribozymes (Cech, 1995, *Biotechnology* 13:323) and others of hammerhead ribozymes (Edgington, 1992, *Biotechnology* 10:256).

Ribozymes and antisense polynucleotides can be delivered directly as a drug in a suitable pharmaceutical formulation (see infra), or indirectly by means of introducing a nucleic acid into a cell, including liposomes, immunoliposomes, ballistics, direct uptake into cells, and the like as known in the art. Methods useful for delivery of polynucleotides for therapeutic purposes are described in U.S. Pat. No. 5,272,065. In one embodiment, vectors (e.g., DNA vectors) encoding ribozyme or antisense polynucleotides are administered by injection (e.g., either transiently or as part of a gene therapy regimen).

B. Inhibiting Binding Between a Ligand and a US28 or US28 Homolog

Instead of inhibiting the expression of US28 or a US28 homolog, some treatment methods reduce viral dissemination by interfering with the interaction of a US28 or US28 homolog and a ligand that is naturally bound by US28 or the US28 homolog. Certain methods interfere with the interaction between the receptor and a chemokine. The chemokine typically is from either the CC or CX3C classes of chemokines. Thus, in some methods an agent is administered that interferes with binding between the receptor and a CX3C chemokine such as fractalkine. Other methods are based upon use of agents that inhibit binding between receptor and CC type chemokines. Examples of CC chemokines include, but are not limited to , MIP-1α, MIP-1β, MCP-1, eotaxin, vMIP-2, or RANTES.

1. Antibodies

Antibodies are an example of one type of agent that can be used to inhibit binding between a chemokine and US28 or a US28 homolog. Such inhibition can be achieved, for example, through steric hindrance. Typically, the antibody specifically binds an epitope on the extracellular region of US28 (e.g., SEQ ID NO:4; see FIG. 1B) or one of the US28 homologs. Thus, certain treatments involve administering an antibody that specifically binds to human UL33 (SEQ ID NO:20), human UL33 spliced (SEQ ID NO:22) or human UL78 (SEQ ID NO:16). Other treatment methods involve administering an antibody that specifically binds to one of the rhesus US28 homologs (i.e., SEQ ID NOS:6, 8, 10, 12, 14, 18, 24 and 26).

The anti-US28 antibodies and anti-US28 homolog antibodies used in such treatment approaches can be produced using a variety of routine methods. See, e.g., Harlow, 1988, ANTIBODIES, A LABORATORY MANUAL, Cold Spring Harbor Publications, New York; Coligan, CURRENT PROTOCOLS IN IMMUNOLOGY, Wiley/Greene, NY (1991); Stites et al. (eds.) BASIC AND CLINICAL IMMUNOLOGY (7th ed.) Lange Medical Publications, Los Altos, Calif., and references cited therein; Goding, MONOCLONAL ANTIBODIES: PRINCIPLES AND PRACTICE (2d ed.) Academic Press, New York, N.Y. (1986); Kohler and Milstein, 1975, *Nature* 256:495–97. In certain treatments, monoclonal anti-US28 antibodies are used; whereas, in other instances polyclonal antibody compositions are utilized. Useful anti-US28 and anti-US28 homolog binding compositions can also be produced using phage display technology (see, e.g., Dower et al., WO 91/17271 and McCafferty et al., WO 92/01047).

Using the foregoing methods, antibodies can be generated against the full-length amino acid sequences set forth for US28 or US28 homolog or some fragment thereof that is immunogenic. The fragment generally is at least 5–10 amino acids in length but can be longer. The antibodies which are produced are assayed for specific binding to US28 or US28 homolog and for the ability to block receptor-ligand interactions.

2. Other Inhibitory Molecules

In addition to antibodies, a variety of compounds can be used to inhibit US28 or US28 homolog receptor-ligand interactions, including, without limitation, polypeptides, oligopeptides, polysaccharides, polynucleotides, lipids, small organic molecules (e.g., MW<800, more preferably 300–600), and the like. Small organic molecules can be of a variety of chemical types including, but not limited to, sterols, nucleic acids, derivatives of purine and pyrimidine bases, β-lactams, aromatic compounds, heterocyclic compounds, carbocyclic compounds, oligo-N-substituted glycines, polycarbamates, oligosaccharides, lipids and amino acids, and derivatives and combinations thereof. Such compounds can be a natural product, a synthetic compound, or a chemical compound, or a combination of two or more substances. Typically, compounds are identified by high-through put screening of large libraries of compounds (e.g., combinatorial libraries). Methods for creating and screening such libraries are established and are described, for example, by Dolle and Nelson, J. (1999) *Combinatorial Chemistry* 1:235–282; Needels, et al. *Proc. Natl. Acad. Sci. USA*, 90: 10700 (1993); Ni, et al *J. Med. Chem.*, 39: 1601 (1996); and in PCT publications WO 95/12608, WO 93/06121, WO 94/08051, WO 95/35503 and WO 95/30642, each of the foregoing references being incorporated herein by reference in its entirety for all purposes.

Exemplary small molecules exhibiting inhibitory activity are described in commonly owned U.S. application Ser. No. 09/944,163, filed Aug. 31, 2001, entitled "Modulators of US28," which claims the benefit of U.S. Provisional Application No. 60/228,974, filed Aug. 30, 2000; and in U.S. Provisional Patent Application Ser. No. 60/316,386, filed Aug. 30, 2001, entitled "Bicyclic Compounds as Inhibitors of Chemokine Binding to US28"; and in U.S. application Ser. No. 09/944,051, filed Aug. 30, 2001, entitled "Reagents and Methods for the Diagnosis of CMV Dissemination", which claims the benefit of Ser. No. 60/229,191 filed Aug. 30, 2000, the disclosures of each of the foregoing applications being incorporated herein by reference in their entirety for all purposes.

As used herein, the terms "compound" and "agent," are used interchangeably when used in the context of inhibition of a US28 or US28 homolog-chemokine interaction.

3. Vaccines

The vaccines are generally designed to include CMV or some portion of the virion in which US28 or US28 homolog has been disabled such that US28 or US28 protein is either not produced or is produced in inactive form. In some instances, this means that the segment of the genome encoding US28 or US28 homolog has been completely or substantially removed, either chemically, enzymatically or via recombination. Specific segments, or at least portions thereof, that can be removed for HCMV include those regions of the genome corresponding to US28 (SEQ ID NOS:1 and 3), UL33 (SEQ ID NO:19), UL33 spliced (SEQ ID NO:21) and UL78 (SEQ ID NO:15). For rhCMV, segments, or portions thereof, that can be removed include SEQ ID NOS:5, 7, 9, 11, 13, 17, 23 and 25.

In general the vaccines are administered as a composition that includes some type of pharmaceutically acceptable excipient (carrier). Additional details regarding methods for generating and administering the vaccines is provided in the section on vaccines infra.

VI. Assays for Agents that Inhibit Dissemination of CMV

A. General

A variety of assays are useful for identifying an agent capable of reducing CMV dissemination in a host animal, by determining whether the agent inhibits the binding of a ligand (e.g., a chemokine) to US28, US28 homolog, or a variant or fragment of US28 or the US28 homolog. Using assays such as described herein, agents which interfere with the binding between a chemokine and US28 or a US28 homolog can be identified. By interfering with such binding, the identified agents have utility as inhibitors of the dissemination of CMV. Agents identified by the assays inhibit the binding of a chemokine such as fractalkine to US28 with activity expressed as $IC_{50}$ (that amount of compound that reduces chemokine binding by 50%). Such agents typically have an $IC_{50}$ of approximately 50 μg/mL or less, in other instances 25 μg/mL or less, in still other instances 10 μg/mL or less, in yet other instances less than 1 μg/mL, and in other instances 50 ng/mL or less, 25 ng/mL or less, or 10 ng/mL or less. In addition to having strong binding characteristics, the agents should exhibit low levels of side effects.

The assays described herein fall into three general categories: non-cellular or in vitro assays, cell based assays and in vivo assays. Each of these is described in greater detail in the following sections.

B. Cell Based Assays

In general, cell-based assays involve contacting a cell that expresses US28, US28 homolog or fragment or variant thereof with a candidate agent and a chemokine in a competitive binding format. Typically, the candidate agent and/or chemokine is detectably labeled such that the amount of bound or free agent or chemokine can be determined. Usually, the label will be a fluorescence label, a phosphorescence label, a radiolabel, a colorimetric label, or the like. In certain screening assays the labeled chemokine is a radiolabeled fractalkine (e.g., $^{125}$I-fractalkine). Radiolabeled chemokines are available commercially (e.g., Amersham, New England Nuclear) or can be prepared using routine techniques.

1. Cells

Cells expressing US28 or US28 homolog can be prepared in primarily two ways. One option is to transfect cells with a nucleic acid that encodes US28 or the US28 homolog (e.g., SEQ ID NOS: 1, 3, 5, 7, 9, 11, 13, 15, 17, 19, 21, 23 and 25). A number of different cell lines can be utilized in the assays of this type. For example, in certain assays the cell line is a mouse cell line (e.g., NSO cells from R&D Systems, Minneapolis, Minn., USA). In other instances, the cell line is a human cell line, (e.g. human embryonic kidney 293 cells ("HEK293") (available from the American Tissue Culture Collection). Other mammalian cells that can be utilized include, but are not limited to CHO, HeLa, HepG2, BaF-3, Schneider, COS, CV-1, HuTu80, and NTERA cell lines.

In general, such cell lines are transfected with an expression cassette including a promoter (e.g., CMV promoter) operably linked to US28 cDNA or US28 homolog cDNA using conventional methods, so as stably or transiently to express the US28 or US28 homology gene product in the transfected cell. Thus, an expression cassette used to transfect cells to express US28 includes a promoter and a nucleic acid sequence from SEQ ID NO:1 or 3 or subsequence thereof which encodes a protein retaining US28 activity. For cells transfected to express a US28 homolog, the expression cassette includes a promoter and a nucleic acid as set forth in SEQ ID NOS:5, 7, 9, 11, 13, 15, 17, 19, 21, 23 or 25), or a subsequence thereof which encodes a protein retaining an activity of the US28 homolog.

Instead of transfecting cells to obtain expression of US 28 or US28 homologs, cells can instead be infected with CMV. In assays systems of this type, the cell line is a primary cell line, e.g., rhesus monkey dermal fibroblast (available from the University of California at Davis Primate Center), primary human lung or foreskin fibroblasts (Clonetics, San Diego, Calif.), human diploid lung fibroblasts (MRC-5 and WI-38), HUVECs, or the like. Cells can be infected with whole virus (CMV) and utilized in the assay following viral expression of the US28 or US28 homolog gene product (e.g., typically about 48–72 hours post infection). Cells typically are infected by contacting with an innoculum containing between 0.01 and 5 infectious particles per cell in minimal volume for a period of 1 hour at 37° C. with gentle rocking. Innoculum is removed and replaced with fresh medium (DMEM+10% FBS).

2. Chemokine

Some assays are conducted with CX3C chemokines such as fractalkine; such assays can be utilized to identify tight binding inhibitors given the high affinity between fractalkine and the US28 receptor. Other assays are performed with chemokines from the CC class including, but not limited to, MIP-1α, MIP-1β, MCP-1, MCP-3, eotaxin, vMIP-2, or RANTES.

3. Methodology

Typically, cells are initially cultured in a suitable buffer (e.g., IMDM-5% FBS, DMEM-10% FCS, HUVEC complete medium, and the like) then centrifuged and resuspended in assay buffer (e.g., HEPES with NaCl, $CaCl_2$, $MgCl_2$, and BSA) to a concentration of from about $5\times10^5$ to about $5\times10^7$, preferably from about $2\times10^5$ to about $8\times10^5$ cells/ml. Aliquots of the cells are then contacted with the candidate agent and labeled chemokine.

After contacting the cells with one or more candidate agents in the presence of labeled chemokine, the assay mixture is typically incubated for a period of time of from about 1 to about (hours at a temperature of from about 1 to about 10° C. Preferably the mixture is incubated for a period of from about 2 to about 4 hours at a temperature of about 4° C. One of skill in the art will understand that a variety of assay conditions can be employed, depending on the cell line used, the concentrations of the compounds and chemokine and the concentration of the cells themselves, for example.

Following incubation, the assay wells can be harvested under vacuum using filter plates, pre-soaked with PEI solution (for those embodiments carried out on 96-, 384-, 1536-well or larger plates). Scintillation fluid (for radiolabel assays) is added, the plates are sealed and the wells are counted. Alternatively, other quantitative methods are employed when, for example, other types of detectably labeled chemokines or agents are used (e.g., fluorescent labels).

Other formats involve contacting a chemokine that is immobilized to a support with a labeled cell that expresses US28 or US28 homolog or a fragment or variant of US28 or the US28 homolog. The support can be made of essentially any material that is compatible with the conditions and components utilized to perform the assays. Exemplary materials include, but are not limited to, glass slides, microtiter wells, membranes and the like.

Another assay that can be used to identify agents that specifically inhibit the binding of chemokine (e.g., fractalkine) to US28 or US28 homolog is a cytoplasmic calcium mobilization assay. In certain methods, assays are performed by: (i) loading US28 or US28 homolog-expressing 293 cells with INDO-1 dye (45 min. at room temperature IN THE DARK), and (ii) washing with PBS, and resuspending into Ca2+ 'flux' buffer (HBSS with 1% fetal bovine serum). For each test, $1 \times 10^6$ cells are incubated at 37° C. in the cuvette of a PTI spectrometer, excited at 350 nm, and the ratio of 410/490 nm emission plotted over time (typically 2–3 minutes), with compounds added at 5 seconds, followed by chemokine (e.g., fractalkine) at 60 seconds. A rise in intracellular Ca2+ indicates that the US28 receptor has bound to the ligand, engaged a G-protein linked cascade which resulted in the mobilization of Ca2+ in the cytoplasm of the US28-bearing cells. Compounds that inhibit ligand (e.g., a chemokine such as fractalkine) binding are tested in this assay for the effects on Ca2+ in this system.

C. Cell-Free Assays

Alternatively, cell-free systems can be employed utilizing a full-length US28 or US28 homolog, or a fragment or a variant of US28 or US28 homolog (e.g., $NH_2$-terminal peptide, extracellular loops and the like). Such proteins can be used alone (or in combinations of fragments of US28 or US28 homologs) to assay binding levels of a chemokine in the presence of a candidate agent.

Cell-free assays can be conducted in a variety of formats. For example, in certain cell-free assays, expressed or synthesized receptor proteins of US28 are embedded in artificial membrane systems to assay for chemokine binding in the presence of a candidate agent (see for example, systems described in Kitaguchi, et al., 1999, *Biochem. Biophys. Res. Commun.* 261:784–89 and Myung, et al., 1999, *Anal. Biochem.* 270:303–13).

Other formats involve contacting a chemokine that is immobilized to a support with a labeled US28 protein or US28 homolog or fragment or variant thereof in the presence of test agent and then detecting the formation of complex containing the label. Another format is one in which US28 or US28 homolog, or fragment or variant is attached to the support and the immobilized receptor, fragment or variant is contacted with a labeled chemokine in the presence of test agent, with subsequent detection of label bound by the immobilized receptor.

D. In Vivo Assays

The discovery by the current inventors that the genome of rhCMV contains reading frames that encode proteins with homology to human US28 is important because it provides a model system for studying the dissemination of human CMV and provides a means by which agents that are effective in arresting or reducing the dissemination of CMV in vivo can be identified. As explained earlier, the finding that rhCMV contained such reading frames was unexpected because the genome of several different CMV strains was found not to contain reading frames encoding proteins with homology to human US28 (e.g., rats and mice). Furthermore, it was not to be expected that the genome of rhCMV would be found to contain multiple different reading frames.

That the genome of rhCMV in fact does encode one or more US28 homologs has been confirmed at two levels. First, as described in greater detail in Example 3, rhesus cells infected with rhCMV express a protein that has binding affinity for the chemokine fractalkine (see also FIG. 6). Secondly, the current inventors have shown that rhCMV virions, like human CMV virions, express at least one protein with fractalkine binding activity (i.e., a US28 homolog). Details of the experiments conducted to demonstrate this are provided in Example 4 and summarized in FIG. 7.

A list of the sequence identifiers for the nucleotide sequences of the open reading frames encoding the rhesus US 28 homologs and the corresponding amino acid sequences are summarized in Table 3 supra. The actual nucleotide and amino acid sequences of the rhesus US28 homologs are shown in SEQ ID NOS:5, 7, 9, 11, 13, 17, 23 and 25 (nucleotide sequences) and SEQ ID NOS:6, 8, 10, 12, 14, 18, 24 and 26 (amino acid sequences).

The in vivo screening assays generally involve administering a test agent to a non-human animal such as a monkey (e.g., a rhesus monkey) infected with CMV and then determining whether the test agent inhibits the function or activity of the US28 homolog or fragment or variant thereof. In general this involves a determination of whether the test agent causes a detectable reduction in the dissemination of CMV in the non-human animal. More specifically, certain assay methods involve introduction of CMV into the animal and then a determination of the degree to which the virus spreads from a primary site to one or more secondary sites.

If the animals being utilized are not already infected, CMV can be introduced by oral inoculation, intravenous injection and other methods known to those of skill in the art. The test agent that is administered can be of any of the types discussed supra including, but not limited to, antibodies, vaccines, antisense nucleic acids, ribozymes and small molecules. The test agent can be administered to the animal in a number of different ways. Exemplary modes of administration include, but are not limited to, parenteral injection either intravenously, subcutaneously or intramuscularly (single or multiple doses), orally, and by the use of an osmotic pump (e.g., the Alzet Osmotic Pump, DURECT Corporation, Cupertino, Calif.). Other approaches are described in the section on pharmaceutical compositions.

Determination of the extent to which the CMV virus is disseminated or spreads from the site of primary infection can be accomplished in a number of different ways. One method is to collect sterile blood, saliva and/or urine samples prior to infection of the animal and then again periodically thereafter. Viral titer can then determined according to established protocols (see, e.g., Spaete and Mocarski, 1985, *J Virol* 56:135–43). In a second approach, blood samples obtained before and after infection are assayed for viral DNA by nested PCR using primers that are specific for CMV (kits containing such primers are available from, for example, Qiagen, Calif.). A third alternative involves direct detection of CMV in various tissues by performing a necroscopy on the infected animals approximately 15 to 30 days after administration of virus. Tissue and blood samples are taken and DNA purified from these samples, typically using commercially available kits (e.g., those from Qiagen, Calif.). The resulting purified DNA then serves as a template for nested PCR as just described.

Histological analyses can also be conducted by staining tissue samples with antibody that specifically binds to CMV (e.g., rhCMV). Inhibition of CMV dissemination is demonstrated by a difference of viral titer or kinetics (as described supra) as assessed by levels of viral antigens in specific tissues or organs of experimental animals compared to control animals. Another alternative is to determine the levels of reactive leukocytes in the peripheral blood of the infected animal (e.g., by FACS analysis of blood samples). Inhibition of CMV dissemination is demonstrated by fewer activated T cells or memory T cells in peripheral blood of experimental animals compared to control animals. Suitable assays for conducting such an analysis is described by Lockridge et al. (1999) *J Virol*. 73:9576–83.

Further details regarding the performance of in vivo assays including a more detailed description of the foregoing approaches for detecting reduction in CMV dissemination are provided in Example 5.

VII. Vaccines

A. Background

Immune-modulation by CMV genes plays a crucial role in pathogenesis, persistence and immunity. The ability of US28 and US28 homologs to bind chemokines such as fractalkine indicates a role for these proteins in the alteration of migration/activation of immune cells that are near CMV infected cells and in trafficking of infected cells via some type of US28 mediated migration. Thus, modification of viral coding regions which control the magnitude of immune responses and influence viral dissemination in the host are key targets to achieve the correct balance between attenuation and immune-stimulation. Alterations at these loci can be used to produce an acceptable vaccine profile.

Thus, the general approach for vaccine development is to produce rhCMV in which one or more of these immuno-modulatory loci are altered. In this way attenuated forms of the virus can be produced which are non-pathogenic but which are still able to induce a recipient's immune system, preferably by generating cell mediated immunity such as the induction of $CD8^+$ cells. CMV altered at such loci is then evaluated by introducing the altered CMV into a rhesus monkey (*macaca mulatta*) and determining the resulting phenotype. More specifically, vaccines are generally designed to include CMV or some portion of the virion in which US28 or US28 homolog has been removed such that US28 or US28 protein is either not produced or is produced in inactive form. In some instances, this means that the segment of the genome encoding US28 or US28 homolog has been completely or substantially removed, either chemically, enzymatically or via recombination. Specific segments, or at least portions thereof, that can be removed include those regions of the genome encoding for US28 (SEQ ID NOS:1 and 3) or US28 homolog (SEQ ID NOS:5, 7, 9, 11, 13, 15, 17, 19, 21, 23 or 25).

Candidate vaccines showing good efficacy in the rhesus model system can then serve as candidates in humans. Alternatively, similar vaccines can be prepared from human CMV.

B. Exemplary Method for Making Non-Pathogenic Forms of CMV

One approach for generating rhCMV that is altered at the regions encoding the rhesus US28 homologs involves the following strategy:

1. A cloning vector carrying an insertion containing a sequence that is homologous to one of the rhesus US28 homologs is constructed. The vector includes the desired modifications to the segment(s) encoding the US 28 homolog(s) under evaluation and a selective marker (e.g., green fluorescent protein (GFP) and/or puromycin).

2. Wild type CMV DNA and the recombinant vector from step (1) are co-transfected into rhesus dermal fibroblasts (DF) using calcium phosphate transfection protocols. The rhesus DF are propagated in DMEM and 10% FBS.

3. Cellular recombination of the wild type DNA with the homologous regions in the vector results in a small number of cells infected with a recombinant genome.

4. Cells containing recombinant virus are isolated by selection of the marker (e.g., by FACS detection of GFP or puromycin selection).

5. Plaques containing infected cells are then purified and the recombinant virus subsequently amplified in rh DF.

Recombinant viruses may also be constructed utilizing cosmid technology (see, e.g., Kemble G, Duke G, Winter R, Spaete R., (1996) J. Virol. 70:2044–8) or by bacterial artificial chromosome technology (see, e.g., Borst EM, et al. (1999) J. Virol. 73:8320–9). Other methods are discussed in commonly owned U.S. Provisional Application No. 60/265, 925, which is incorporated herein by reference in its entirety for all purposes.

C. Evaluation of Candidate Vaccines

The resulting amplified viral recombinants are initially analyzed in vitro to confirm the nature of the recombinant. Rhesus CMV DNA is prepared by SDS/proteinase K digestion of supernatant virions, followed by phenol/chloroform extraction and ethanol precipitation.

Restriction fragment analysis and Southern blot comparison of the viral recombinants to parental DNA as well as sequencing is used to confirm the altered genotype (i.e., that some or all of region encoding the US28 homolog has been removed). Growth characteristics of the recombinants are compared to the parental strain at both high (5 pfu/cell) and low (0.01 pfu/cell) MOI (multiplicity of infection). Rhesus DF are separately inoculated with parental and recombinant virus, harvested at various time points (0–4 days high MOI and 0–10 days low MOI) and total cellular viral load of these samples determined by serial dilution and plaque assay in rhesus DF.

The phenotype of the US28 recombinant can be assessed using chemokine binding assays. In such assays, recombinant and parental virus infected rhesus DF, as well as density gradient purified virions (see Examples infra), are incubated with $^{125}I$ labeled fractalkine and increasing concentrations of cold competitor in a competition binding experiment. Cells or virions are then immobilized on a support (e.g., glass filters), and unbound label is washed away, such that bound label can then be quantified by scintillation counting. $IC_{50}$ values for the US28/fractalkine interaction is determined from this competitive binding analysis (see Examples 1, 3 and 4 for additional details). Abrogation of fractalkine binding to recombinant US28 virions containing a deletion one of the coding regions for a US28 homolog and infected cells is evidence that the loci corresponding to the US28 homolog being investigated has in fact been modified.

CMV virions confirmed to have the desired modification can then be formulated as a vaccine and administered to a rhesus monkey. The effectiveness of the vaccine in inducing an immune response and inhibiting CMV dissemination can be assessed, for example, using any of the various dissemination assays described in the in viva assay section supra.

D. Formulation and Administration

Candidate forms of the virus identified by the screening procedures described supra are typically combined with a pharmaceutically acceptable excipient (carrier) for administration to a patient.

A variety of different excipients or carriers can be utilized in the vaccines including, for example, adjuvants and compounds that stimulate T-cells, such as Freund's adjuvant, Ribi adjuvant (Ribi, et al., *Clin. Immunol. Newsletter*, 6:33–36, 1985) and BCG. Other excipients include Montanide ISA5 1 and Alum adjuvants (previously approved for use in primates and himans, respectively). Other suitable adjuvants include aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), and N-acetylmuramyl-Lalanyl-D-isoglutaminyl-L-alanine-2-(1'-2'-dipalmitoyl-sn-glycero-3-hydroxy-phosphcryloxy)-ethylamine (CGP 19835A, referred to as MTP-PE). The effectiveness of an adjuvant can be determined by measuring the amount of cross-reactive antibodies directed against the immunogenic antigen. In certain instances, cyclophosphamide, an inhibitor of suppressor T-cell response, is included with the vaccine.

The vaccines described herein can be used to induce a therapeutic or protective immune response in a patient and in methods for treating diseases such as those described infra. Such methods include administering to a patient a therapeutically effective amount of a vaccine of the invention. A therapeutically effective amount of the vaccine is an amount sufficient to elicit a therapeutic or protective immune response, such as inducing the formation of antibodies and/or other cellular immune responses (e.g., the induction of helper T cells, cytotoxic killer T-cells, anomalous killer cells (AK cells) and/or antibody-dependent cytotoxic cells).

Doses, methods of administrating, and suitable pharmaceutical carriers can be determined readily by the skilled artisan. For example, appropriate doses can be extrapolated from dose-response studies in animals, including non-human primates. An appropriate immunization schedule can be determined by a skilled artisan but generally depends upon the susceptibility of the host or patient to immunization with the vaccine and is typically continued until sufficient antibody is detectable in whole serum.

The vaccines can be administered in a variety of different ways including, for example, by oral, intranasal, intraperitoneal, intravenous, intramuscular, subcutaneous, subdermal and transdermal methods. It has been found in some instances that although similar immunologic responses are generated by either intraperitoneal or subcutaneous administration that the latter form of administration is capable of inducing higher T-cell responses.

VIII. Additional Pharmaceutical Compositions

A. Active Component

In addition to the vaccines just described, other inhibitory agents described herein or identified using the screening assays disclosed herein can be formulated as part of a pharmaceutical composition for use in preventing CMV dissemination in a host. As described supra, such agents can include, for example, antisense nucleic acids, ribozymes, antibodies and small molecules. Typically, the compositions contain from about 0.1% to about 99% by weight of active compound, and in other instances from about 10% to about 60% by weight depending on which method of administration is employed.

Certain agents that are identified can serve as lead compounds for the synthesis of analog compounds that exhibit even higher activity (e.g., increased inhibition of CMV dissemination). Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al. (1989) *Computer-Assisted Modeling of Receptor-Ligand Interactions* (Alan Liss, New York).

Once analogs have been prepared, they can be screened using the methods disclosed supra to identify those analogs that exhibit an increased ability to inhibit dissemination of CMV. Such compounds can then be subjected to further analysis to identify those compounds that appear to have the greatest potential as pharmaceutical agents. Alternatively, analogs shown to have activity through the screening methods can serve as lead compounds in the preparation of still further analogs, which can be screened by the methods disclosed herein. The cycle of screening, synthesizing analogs and rescreening can be repeated multiple times to further optimize the activity of the analog.

Further guidance on the synthesis of analog compounds and lead optimization is provided by, for example: Iwata, Y., et al. (2001) *J. Med. Chem*. 44:1718–1728; Prokai, L., et al. (2001) *J. Med. Chem*. 44:1623–1626; Roussel, P. et al., (1999) *Tetrahedron* 55:6219–6230; Bunin, B. A., et al. (1999) *Ann. Rep. Med. Chem*. 34:267–286; Venkatesh, S., et al. (2000) *J. Pharm. Sci*. 89:145–154; and Bajpai, M. and Adkinson, K. K. (2000) *Curr. Opin. Drug Discovery and Dev*. 3:63–71.

B. Compositions

In general the pharmaceutical compositions include an active ingredient such as just described in combination with a pharmaceutically acceptable carrier as part of a formulation or medicament for the treatment of various conditions related to CMV infection, although certain active ingredients can be administered without formulation with a carrier.

Some compositions can also include other antiviral agents that are either therapeutic or prophylactic agents, and different from the foregoing active ingredients. The compositions can also include and be used in combination with agents that treat or induce conditions often associated with the viral infections that are sensitive to the present compounds, such as anti-HIV agents or immunosuppressive agents. In many instances, administration in conjunction with the subject compositions enhances the efficacy of such agents. Exemplary antiviral agents include ganciclovir, foscarnet and cidofovir. Exemplary anti-HIV agents include indinavir, ritonavir, AZT, lamivudine and saquinavir. Exemplary immunosuppressive agents include cyclosporin and FK-506. The compositions can also be used as antiviral prophylactic treatment in combination with immunosuppressive protocols such as bone-marrow destruction (either by radiation or chemotherapy).

The compositions can also include various agents to enhance delivery and stability of the active ingredients. Thus, for example, the compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant, for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. Polypeptides can also be complexed with molecules that enhance their in vivo attributes. Such molecules include, for example, carbohydrates, polyamines, amino acids, other peptides, ions (e.g., sodium, potassium, calcium, magnesium, manganese), and lipids.

The proportion of each carrier, diluent or adjuvant is determined by the solubility and chemical nature of the compound and the route of administration according to standard pharmaceutical practice. In order to obtain consistency of administration, however, it is preferred that a composition of the invention is in the form of a unit dose. For example, the unit dose presentation forms for oral administration may be tablets and capsules and may contain conventional excipients such as binding agents (e.g., acacia, gelatin, sorbitol, or polyvinylpyrrolidone), fillers (e.g., lactose, sugar, maize-starch, calcium phosphate, sorbitol or glycine), tableting lubricants (e.g., magnesium stearate), disintegrants (e.g., starch, polyvinylpyrrolidone, sodium starch glycoallate or microcrystalline cellulose), or pharmaceutically acceptable wetting agents (e.g., sodium lauryl sulfate).

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527–1533 (1990).

C. Dosage

The pharmaceutical compositions can be administered as part of a prophylactic and/or therapeutic treatments. A "therapeutically effective" amount refers to an amount that is sufficient to remedy a disease state or symptoms, particularly symptoms associated with CMV infection, or otherwise prevent, hinder, retard, or reverse the progression of disease or any other undesirable symptoms in any way whatsoever. A "prophylactically effective" amount refers to an amount administered to an individual susceptible to or otherwise at risk of a particular condition associated with CMV or CMV infection to prevent, retard or lessen the progression of the disease or the undesirable symptoms associated with the disease.

A CMV dissemination-inhibiting amount is that amount of active compound required to slow the progression of viral dissemination or reduce the amount of viral dissemination from that which would otherwise occur without administration of the compound, e.g., as determined according to the assays described herein. Or, it is an amount of active compound required to slow the progression or reduce the intensity of symptoms resulting from CMV infection or elimination thereof.

Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. More specifically, the effective doses as determined in cell culture and/or animal studies can be extrapolated to determine doses in other species, such as humans for example. The dosage of the active ingredient typically lines within a range of circulating concentrations that include the ED50 with little or no toxicity. The dosage can vary within this range depending upon the dosage form employed and the route of administration utilized. What constitutes an effective dose also depends upon the nature of the disease, the general state of an individual's health and the specific properties (e.g., IC50) of the agent. In general terms, however, the amount of active ingredient will generally be approximately about 0.05 mg/kg to about 20 mg/kg, more preferably in the range of about 0.05 mg/kg to about 2 mg/kg, most preferably in the range of about 0.05 mg/kg to about 0.2 mg per kg of body weight per day. 0.01 to 250 mg/kg/day, often about 0.5 to 30 mg/kg/day, more often about 1 to 20 mg/kg/day, and most often about 1–10 mg/kg/day to less.

D. Administration

The compositions and the inhibitory agents disclosed herein as well as pharmaceutically acceptable salts thereof can be administered in any effective way such as via oral, parenteral or topical routes.

The compounds may be injected parenterally; this being intramuscularly, intravenously, or subcutaneously. For parenteral administration, the compound may be used in the form of sterile solutions containing other solutes, for example, sufficient saline or glucose to make the solution isotonic.

The compounds can be administered orally in the form of tablets, capsules, or granules containing suitable excipients such as starch, lactose, white sugar and the like, in the form of solutions, or sublingually. The amount of active ingredient administered orally will depend on bioavailability of the specific compound. The solid oral compositions may be prepared by conventional methods of blending, filling, tableting, or the like. Oral liquid preparations can be in the form of emulsions, syrups, or elixirs, or can be presented as a dry product for reconstitution with water or other suitable vehicle before use. Such liquid preparations may or may not contain conventional additives.

The compositions can also be administered in the form of suppositories for rectal administration of the drug. For topical use, creams, ointments, jellies, solutions or suspensions, etc., containing the active ingredients are employed. As used herein, topical application is also meant to include the use of mouth washes and gargles.

In some instances, the active ingredient can be provided in the form of a pro-drug, that can be metabolically or chemically converted to the active ingredient by the recipient host. A wide variety of pro-drug derivatives are known in the art such as those that rely on hydrolytic cleavage or oxidative activation of the prodrug.

Therapeutic and prophylactic methods of involve treating patients in a pharmaceutically acceptable manner with those compounds or compositions. Such compositions may be in the form of tablets, capsules, caplets, powders, granules, lozenges, suppositories, reconstitutable powders, or liquid preparations, such as oral or sterile parenteral solutions or suspensions. The pharmaceutical compositions described herein can also be administered via an intraocular implant for treating retinitis as a result of CMV infection. In particular, active ingredients can be embedded in a polymer based implant which is released into the eye over an extended period of time.

Physicians can determine the dosage of the present therapeutic agents which will be most suitable. As described supra, dosages may vary with the mode of administration and the particular compound chosen. In addition, the dosage may vary with the particular patient under treatment. The dosage of the compound used in the treatment will vary, depending on viral load, the weight of the patient, the relative efficacy of the compound and the judgment of the treating physician. Such therapy may extend for several weeks or months, in an intermittent or uninterrupted manner.

IX. Exemplary Utilities

As indicated in the Background section, CMV is an opportunistic pathogen that infects primarily fetuses in utero and immunocompromised adults. In the case of neonates that become infected in utero, the infection can cause mental retardation, deafness and various neurological sequelae. Thus, the pharmaceutical compositions and vaccines described herein can be utilized as a prophylactic to prevent primary infection of women during pregnancy, thereby preventing transmission of the virus during gestation and birth.

Acute or re-emerging infections of CMV can result in retinitis, encephalitis and pneumocystis. Administration of the pharmaceutical compositions and vaccines provided herein can be used prophylactically or therapeutically to treat such diseases.

The pharmaceutical compositions and vaccines disclosed herein can also be utilized to treat a number of diseases to which immunocompromised individuals are susceptible. Examples of such diseases include artery occlusion following heart transplants, and arthrectomy and restenosis following angioplasty. There is some evidence to suggest that the arterial call nay be a site of latent CMV and that CMV induces atherosclerotic lesions. It also appears that CMV can play a role in chronic rejection syndrome and graft versus host disease. Thus, the compositions provided can be used to treat these diseases as well. Of course, other systemic sequelae associated with CMV can be treated as well using the compositions provided herein.

The following examples are provided to illustrate certain aspects of the methods and compositions provided herein and are not to be construed to limit the scope of these methods and compositions.

EXAMPLE 1

Demonstration of Expression of US28 by CMV Virions

I. Background

To gain insight into the mechanism by which CMV is disseminated, this set of experiments was conducted to determine whether human CMV viral particles express US28. If so, the virus may be transported from the site of primary infection by being transported (e.g., in the circulatory system of the infected host) from the primary site of infection to another site where the viral particle becomes attached via the US28 receptor to a chemokine (e.g., fractalkine) expressed at the cell surface.

II. Experimental

Human dermal fibroblasts were infected with HCMV strain Toledo or HCMV TolΔUS28 (Streblow et al., 1999, Cell 99:511–20) at an MOI of 0.01 and maintained at 37° C. and 5% $CO_2$ in Dulbecco's minimal essential medium with 10% fetal calf serum and fed as necessary. At day 15 post infection supernatant was collected and clarified by two rounds of centrifugation at 400 g. Virions from the clarified supernatant were pelleted at 10,000 g, resuspended in TN (50 mM TRIS-Cl pH 7.5, 100 mM NaCl), and purified over two consecutive 20–70% sucrose gradients by standard techniques (Britt W J., 1984, Virology 135: 369–78). Virions were resuspended in 500 ul of assay buffer (20 mM HEPES, 140 mM NaCl, 1 mM $CaCl_2$, 5 mM $MgCl_2$, and with 0.2% bovine serum albumin) and 0.09 mL added to each well of assay plates containing serial dilutions of fractalkine (concentrations between 0–250 nM) in triplicate.

Then 0.09 mL of $^{125}$I-fractalkine diluted in assay buffer (final concentration ~2–10 fM, with ~30,000 cpm per well) was added, the plates sealed and incubated for approximately 3 hours at 4° C. on a shaker platform. The assay plates were harvested using Packard filter plates, pre-soaked in PEI solution, on the vacuum harvest apparatus. Scintillation fluid (35 μL) was added to all wells, the plates were sealed and counted in a Top Count scintillation counter. Control wells containing either diluent only (for total counts) or excess fractalkine (1 μg/mL, for non-specific binding) were used to calculate the percent of total inhibition for each set of compounds.

In wild type virions (Toledo), labeled fractalkine bound strongly to the virions and was competed off by unlabeled fractalkine with an $IC_{50}$ of about $4 \times 10^{-11}$. However virions from a virus identical except for deletion of US28 from the genome (TolΔUS28) had virtually no binding to the labeled fractalkine (see FIG. 5).

III. Results/Conclusion

These results demonstrate that US28 is a virion molecule capable of interacting with fractalkine.

EXAMPLE 2

Identification of Rhesus US28 Homologs

I. Background

Given the role that US28 appears to play in CMV dissemination, an in vivo system for conducting further studies on the receptor would be useful. However, the CMV strain infecting rats as well as the CMV that infects mice were found to lack a US28 homolog. This investigation was conducted to determine whether the genome of rhCMV contains regions having homology with the coding region for human US28.

II. Experimental

Rhesus dermal fibroblasts (RhDF) were infected at an MOI of 3 with rhesus CMV strain 68.1 (see ATCC # VR-677). At 96 hours post infection supernatants were collected. Supernatants were cleared by two spins at 1,500 rpm for 5 minutes in a bench top centrifuge. Virions were pelleted from the supernatant for 30 minutes at 10,000 rpm in a Beckman JA-21 or J-14 centrifuge or similar centrifuge and resuspended in 0.5 ml TN buffer (0.05 M Tris/HCl, pH 7.4, 0.1M NaCl) then layered onto a 5 ml sucrose density gradient (20% to 70% w/v sucrose in TN) in a SW 50 centrifuge tube. Gradients were spun 90 minutes at 24,000 rpm in Beckman SW50 at 10° C. The virion band was collected by piercing the tube with a needle just below band and recovered in minimal volume, then diluted 4 fold in TN buffer and spun 30 minutes at 20,000 rpm in a Beckman SW50 centrifuge at 10° C. to pellet virions.

The isolated virions were resuspended in TE buffer (Tris HCl 10 mM, 0.5 mM EDTA) and proteinase K added to a final concentration of 0.2 ug/ml, SDS to a final concentration of 1% and RnaseA to a final concentration of 10 ug/ml. The resulting mixture was incubated for 2 hours at 65° C. The mixture was then subjected to one phenol extraction, one phenol/chloroform extraction and one chloroform extraction according to standard techniques (see, e.g. Sambrook et al., 2001, MOLECULAR CLONING, A LABORATORY MANUAL, 3D ED., Cold Spring Harbor, N.Y.; and Ausubel et al. (eds). CURRENT PROTOCOLS IN MOLECULAR BIOLOGY, Green/Wiley, N.Y. (1994–1998 and periodic supplements through year 2000).

Viral DNA is precipitated with ethanol in accordance with established techniques and then resuspend in sterile TE. The resulting suspension was provided to Genome Therapeutics, MA for sequencing. The DNA was used to create a shot gun library using hydroshearing and producing inserts of about 3,000 bp in length. Individual clones were sequenced using ABI Prism BigDye terminator chemistry. The 220 kb genome was covered to an average accuracy of 6× sequence. Individual reads were assembled into contiguous fragments. Homologs of human CMV genes were elucidated using the BLAST X program. Sequence was further analyzed using the BioNavigator™ bio-informatic program set (Entigen Corp, CA).

III. Results/Conclusion

Analysis of the rhCMV genome indicated the presence of a number of open reading frames having homology with the human CMV US28 open reading frame. As indicated supra, the present inventors refer to these regions of homology as rhUS28.1 (SEQ ID NO:5), rhUS28.2 (SEQ ID NO:7), rhUS28.3 (SEQ ID NO:9), rhUS28.4 (SEQ ID NO:11), and rhUS28.5 (SEQ ID NO:13). Other regions having homology to human UL33 and human UL 78 were also identified and named rhUL33 (SEQ ID NO:23), rhUL33 spliced (SEQ ID NO:25) and rhUL78 (SEQ ID NO:15).

EXAMPLE 3

Expression of rhCMV US28 Homolog on Surface of CMV Infected Cells

I. Background

Having shown in Example 2 that rhesus CMV genome contained regions with homology to human US28, this study was conducted to determine whether rhesus cells infected with rhCMV express a receptor having chemokine binding activity similar to that with human cells infected with human CMV.

II. Experimental

Radioligand binding assays were carried our in the following manner. The target cells typically used in these assays were Rhesus dermal fibroblasts which had been infected with Rhesus; CMV for 3–7 days. Lots of cells verified for fractalkine binding were frozen until ready for use. For the assay, cells were thawed, washed, and resuspended in assay buffer (20 mM HEPES pH 7.1, 140 mM NaCl, 1 mM $CaCl_2$, 5 mM $MgCl_2$, and 0.2% bovine serum albumin) to a concentration of from $4\times10^5$ to $5\times10^6$ cells/ml.

Serial dilutions of unlabeled fractalkine were prepared as a 10× solution in 20% DMSO, and 0.02 ml was placed in assay plates. Next 0.09 ml of cells was added to the assay plates containing the unlabeled fractalkine. Lastly, 0.09 ml of $^{125}$I-fractalkine diluted in assay buffer (final concentration ~50 pM, with 20,000–50,000 cpm per well) was added, the plates sealed and incubated for 2–4 hours at 4° C. on a shaker platform. Assay plates were harvested using Packard GF/B filter plates (pre-soaked in 0.3% polyethyleneimmine (PEI) solution) on a Packard vacuum cell harvester. Scintillation fluid was added to all wells, the plates were sealed and then counted in a Top Count scintillation counter. Control wells containing either diluent only (for total counts) or excess unlabeled fractalkine (1 µg/ml, for non-specific binding) were used to calculate the percent of total inhibition. $IC_{50}$ values are those concentrations required to reduce the binding of labeled fractalkine to the receptor by 50%, and were determined by nonlinear regression curve-fitting of the dose-response assays.

III. Results/Conclusion

Figure 6:
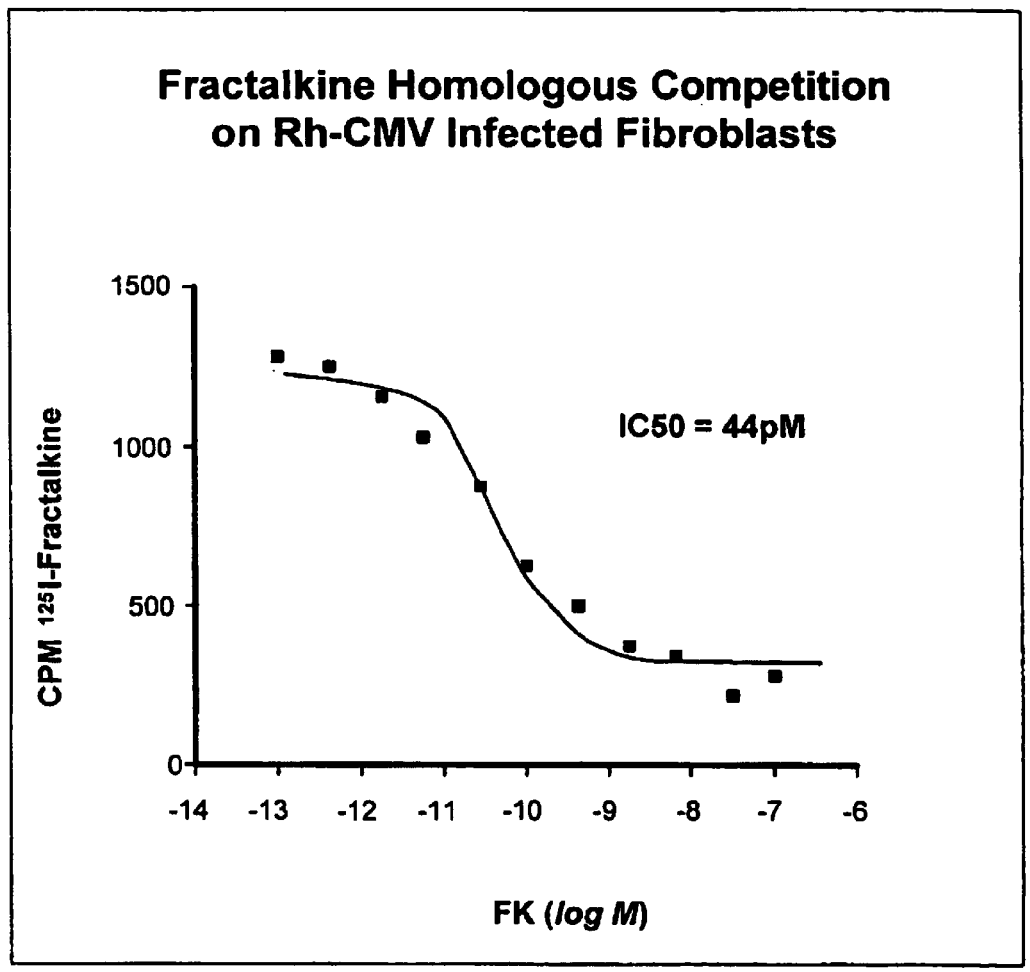
FIG. 6 is a binding plot showing fractalkine binding to rhesus dermal fibroblast cell infected with rhCMV.

FIG. 6 shows a binding plot showing that rhesus cells infected with rhCMV express a receptor protein that has binding characteristics related to those of human US28, namely the ability to bind fractalkine with high affinity ($IC_{50}$=44 picomolar). This result is consistent with the conclusion reached in sequence studies described in Example 2 that rhCMV contains an open reading frame with homology to human US28.

EXAMPLE 4

Demonstration of Expression of Rhesus US28 Homologs by rhCMV Virions

I. Background

This investigation was undertaken to determine whether rhCMV virions express a surface receptor having US28 binding characteristics similar to that of human CMV virions. As with the human virions, such expression would have important implications for the way the virus is disseminated.

II. Experimental

Human dermal fibroblast (HDF) were infected at an MOI of 3 with human CMV strain Toledo or a Toledo strain in which the US28 gene had been replaced with a green fluorescent protein/gpt resistance cassette (Toledo deltaUS28) (see, e.g., Vieira, J. et al. (1998) *J. Virol.* 72:S158–65). Alternatively, rhesus dermal fibroblasts (RhDF) were infected at an MOI of 3 with rhesus CMV strain 68.1 (see ATCC # VR-677). At 96 hours post infection supernatants were collected.

Supernatants were cleared by two spins at 1,500 rpm for 5 minutes in a bench top centrifuge. Virions were pelleted from the supernatant for 30 minutes at 10,000 rpm in a Beckman JA-21 or J-14 centrifuge or other similar centrifuge and resuspended in 0.5 ml TN buffer (0.05 M Tris/HCl, pH 7.4, 0.1M NaCl) then layered onto a 5 ml sucrose density gradient (20% to 70% w/v sucrose in TN) in a SW 50 centrifuge tube. Gradients were spun 90 minutes at 24,000 rpm in a Beckman SW50 centrifuge at 10° C. The virion band was collected by piercing the tube with a needle just below the band and recovered in minimal volume, then diluted 4 fold in TN buffer and spun 30 minutes at 20,000 rpm in a Beckman SW50 centrifuge at 10° C. to pellet virions. TN/sucrose was removed and virions from the HDF cells and the RhDF cells separately resuspended in PBS.

Aliquots of the virions from the two cell types were then separately contacted with $^{125}$I-labeled fractalkine (available from, for example, Amersham and New England Nuclear) and varying concentrations of unlabeled fractalkine. These assay mixtures were then incubated for 3 hours at 4° C.

Following incubation, the assay wells were harvested under vacuum using filter plates, pre-soaked with PEI solution. Scintillation fluid was added, the plates sealed and the radioactivity in the various wells counted.

III. Results/Conclusion

A binding plot showing the extent of binding of the various viral particles to radiolabeled fractalkine is shown in FIG. 7. The results show that HCMV virions lacking US28 do not bind fractalkine. Wild type HCMV virions expressing US28, however, do bind fractalkine tightly as expected in view of the results presented in Example 1. The chart also shows that virions purified from RHDF cells also bind to fractalkine. Thus, these results demonstrate that rhCMV virions, like human CMV virions, express a protein able to bind fractalkine. This result supports the finding from the sequence comparison analysis that rhCMV contains coding regions with homolog to US28.

EXAMPLE 5

Inhibition of CMV Dissemination by Administration of an Inhibitor of a US28-Receptor Interaction I. Background Collectively, the results from the foregoing examples demonstrate that rhesus monkeys infected with rhCMV can serve as an excellent in vivo model system for studies on CMV dissemination. This example describes methods for conducting in vivo studies utilizing rhesus monkeys as such a model system.

II. Experimental

In an exemplary assay, Rhesus CMV strain 68.1 (e.g., $10^{4-10^7}$ pfu, usually $10^6$ pfu, in excipient) is administered by oral inoculation (or intravenous injection) to CMV-negative animals. In "experimental" animals, an inhibitor or putative inhibitor of US28-fractalkine interaction (e.g., octoclotheptin) is also administered, while "control" animals do not receive the inhibitor. The inhibitor is administered at the same time as the virus or, alternatively, prior to or after administration of the virus (e.g., one day prior or up to 2 days post-inoculation). The inhibitor or putative inhibitor can be administered intravenously, subcutaneously or by other modes. Single or multiple injections can be administered. A slow release apparatus such as an Alzet pump (an osmotic pump) can also be utilized.

Viral infection and dissemination in experimental and control animals is determined by analyzing spread of the virus from the site of primary inoculation. Suitable assays for detecting CMV are described in Lockridge et al. (1999) *J. Virol*. 73:9576–83. Sterile blood, saliva and urine samples are collected at the time of virus administration and thereafter periodically (e.g., every day or every 3 days) and assayed for virus. According to one suitable assay, viral titer is measured in saliva, urine and blood samples, by co-cultivation of serial dilutions of sterile samples with a cell permissive for CMV replication (e.g., human dermal fibroblasts) for a period of about 2 weeks, and counting of viral plaques, using standard techniques (Spaete and Mocarski, 1985, *J Virol* 56:135–43). Inhibition of CMV dissemination is demonstrated by a 5-fold or greater (e.g., at least 10-fold) reduction in the overall titer of infectious virus in at least one, sometimes two or three of these fluids in experimental animals compared to control animals when assayed at timepoints after administration of the inhibitor (e.g., 3, 6, 9, 12, or 15 days or 1 month following administration). Inhibition of CMV dissemination can alternatively be shown by a delay in appearance of detectable virus in at least one, sometimes two or three of the these fluids in experimental animals compared to control animals.

In another suitable assay, blood is assayed for viral DNA by PCR using CMV specific primers. For example, in one embodiment, DNA is purified from plasma (e.g., using commercially available kits from Qiagen, Calif.), then used as template for nested PCR with primers able to amplify the rhCMV immediate early 2 gene (5' GCC AAT GCA TCC TCT GGA TGT ATT GTG A 3' (SEQ ID NO:44) and 5' TGC TTG GGG AAT CTC TGC AC 3' (SEQ ID NO:45) then 5' CCC TTC CTG ACT ACT AAT GTA C 3' (SEQ ID NO:46) and 5' TTG GGG AAT CTC TGC ACA AG 3'(SEQ ID NO:47) (see, e.g., Tarantal et al., 1998, *J Infect Dis* 177:446–50). Inhibition of CMV dissemination is demonstrated by a difference of viral titer or kinetics (as described supra) as assessed by levels of viral DNA in peripheral blood.

Assays for viral dissemination can also be carried out by direct detection of CMV in tissues including lung, spleen, thymus, salivary gland, bone marrow, pancreas, kidney, tonsil, liver, parotid gland, esophagus and others. Thus, in embodiment, animals are necropsied 15 to 30 days after administration of virus (e.g., day 30) and complete tissue and blood samples taken. DNA is purified from tissue (e.g. using commercially available kits from Qiagen, Calif.), then used as template for nested PCR as described supra. Dissemination can also be assayed by histology. Typically, tissue is fixed in paraformaldehyde and embedded in paraffin, or frozen in OCT for frozen sections (see, e.g., by Luna, L. G., THE MANUAL OF HISTOLOGIC STAINING METHODS OF THE ARMED FORCES INSTITUTE OF PATHOLOGY, McGraw-Hill, 3rd edition, 1968). Sections are stained using an antibody specific for CMV (e.g., rhCMV). Inhibition of CMV dissemination is demonstrated by a difference of viral titer or kinetics (as described supra) as assessed by levels of viral antigens in specific tissues or organs of experimental animals compared to control animals.

In another suitable assay, levels of reactive leukocytes are assayed, e.g., by FACS analysis of blood samples. Suitable assays are described in Lockridge et al., *J Virol*. 73:9576–83, supra. Briefly, activated T cells are identified by dual fluorescent staining for CD3 (T cell marker, Pharmingen, clone SP34) and CD69 (very early activation marker, Becton Dickinson, clone L78) while memory T cells are identified by dual fluorescent staining for CD3 (T cell marker, Pharmingen, clone SP34) and CD45RO (memory cell marker, Dako, clone UCHL1). Inhibition of CMV dissemination is demonstrated by fewer activated T cells or memory T cells in peripheral blood of experimental animals compared to control animals (e.g., at least about 30% or about 50% fewer, often at least 80% fewer when measured following administration (e.g., 3, 6, 9, 12, or 15 days or 1 month following administration of the agent).

It is understood that the examples and embodiments described herein are for illustrative purposes only and that various modifications or changes in light thereof will be suggested to persons skilled in the art and are to be included within the spirit and purview of this application and scope of the claims. All publications, patents, and patent applications cited herein are hereby incorporated by reference in their entirety for all purposes.

What is claimed is:

1. A composition comprising (a) a replication competent attenuated cytomegalovirus (CMV) that can generate an immune response in a mammal, and (b) a pharmaceutically acceptable carrier, wherein the CMV is attenuated through inhibition of expression or activity of US28 and/or a US28 homolog and wherein said carrier comprises an adjuvant.

2. The composition of claim 1, wherein the mammal is a human or rhesus monkey and the CMV is human cytomegalovirus (HCMV) or rhesus cytomegalovirus (rhCMV), respectively.

3. The composition of claim 2, wherein the mammal is a human and the CMV is HCMV.

4. The composition of claim 3, wherein at least a segment of the HCMV genome encoding US27, US28, UL33 and/or UL78 has been inactivated.

5. The composition of claim 4, wherein the segment comprises the entire US 27, US28, UL33 and/or UL78 encoding region and the encoding region has been deleted.

6. The composition of claim 4, wherein at least a segment of the HCMV genome encoding US27 has been inactivated.

7. The composition of claim 6, wherein the segment comprises the entire US27 encoding region and the encoding region has been deleted.

8. The composition of claim 4, wherein at least a segment of the HCMV genome encoding US28 has been inactivated.

9. The composition of claim 8, wherein the segment comprises the entire US28 encoding region and the encoding region has been deleted.

10. The composition of claim 4, wherein at least a segment of the HCMV genome encoding human UL33 has been inactivated.

11. The composition of claim 10, wherein the segment comprises the entire UL33 encoding region and the encoding region has been deleted.

12. The composition of claim 4, wherein at least a segment of the HCMV genome encoding human UL78 has been inactivated.

13. The composition of claim 12, wherein the segment comprises the entire UL78 encoding region and the encoding region has been deleted.

14. The composition of claim 2, wherein the mammal is a rhesus monkey and the CMV genome is rhCMV.

15. The composition of claim 14, wherein at least a segment of the rhCMV genome encoding rhUS28.1, rhUS28.2, rhUS28.3, rhUS28.4, rhUS28.5, rhUL33, and/or rhUL78 has been inactivated.

16. The composition of claim 15, wherein the segment comprises the entire rhUS28.1, rhUS28.2, rhUS28.3, rhUS28.4, rhUS28.5, rhUL33, and/or rhUL78 encoding region and the encoding region has been deleted.

17. The composition of claim 15, wherein at least a segment of the rhCMV genome encoding rhUS28.1 has been inactivated.

18. The composition of claim 17, wherein the segment comprises the entire rhUS28.1 encoding region and the encoding region has been deleted.

19. The composition of claim 15, wherein at least a segment of the rhCMV genome encoding rhUS28.2 has been inactivated.

20. The composition claim 19, wherein the segment comprises the entire rhUS28.2 encoding region and the encoding region has been deleted.

21. The composition of claim 15, wherein at least a segment of the rhCMV genome encoding rhUS28.3 has been inactivated.

22. The composition of claim 21, wherein the segment comprises the entire rhUS28.3 coding region and the encoding region has been deleted.

23. The composition of claim 15, wherein at least a segment of the rhCMV genome encoding rhUS28.4 has been inactivated.

24. The composition of claim 23, wherein the segment comprises the entire rhUS28.4 encoding region and the encoding region has been deleted.

25. The composition of claim 15, wherein at least a segment of the rhCMV genome encoding rhUS28.5 has been inactivated.

26. The composition of claim 25, wherein the segment comprises the entire rhUS28.5 encoding region and the encoding region has been deleted.

27. The composition of claim 15, wherein at least a segment of the rhCMV genome encoding rhUL33 has been inactivated.

28. The composition of claim 27, wherein the segment comprises the entire rhUL33 encoding region and the encoding region has been deleted.

29. The composition of claim 15, wherein at least a portion of the rhCMV genome encoding rhUL78 has been inactivated.

30. The composition of claim 29, wherein the segment comprises the rhUL78 encoding region and the encoding region has been deleted.

31. The composition of claim 1, wherein the composition is formulated for administration to a human.

32. The composition of claim 1, wherein the composition satisfies GMP standards.

33. A composition comprising (a) a replication competent attenuated human cytomegalovirus (HCMV) that can generate an immune response in a mammal, and (b) a pharmaceutically acceptable carrier, wherein the HCMV is attenuated through inhibition of expression or activity of UL78.

34. A composition comprising (a) a replication competent attenuated rhesus cytomegalovirus (rhCMV) that can generate an immune response in a mammal, and (b) a pharmaceutically acceptable carrier, wherein the rhCMV is attenuated through inhibition of expression or activity of US28 and/or a US28 homolog.

* * * * *

SEQUENCE LISTING

```
<160> NUMBER OF SEQ ID NOS: 48

<210> SEQ ID NO 1
<211> LENGTH: 1065
<212> TYPE: DNA
<213> ORGANISM: Human cytomegalovirus
<220> FEATURE:
<223> OTHER INFORMATION: human cytomegalovirus (HCMV) Toledo strain open
      reading frame US28 (AU4.1)
<221> NAME/KEY: CDS
<222> LOCATION: (1)..(1065)
<223> OTHER INFORMATION: HCMV Toledo US28

<400> SEQUENCE: 1
```

-continued

| | |
|---|---|
| atgacaccga cgacgacgac cgcggaactc acgacggagt ttgactacga tgaagccgcg | 60 |
| actccttgtg ttttcaccga cgtgcttaat cagtcaaagc cggttacgtt gtttctgtac | 120 |
| ggcgttgtct ttctgttcgg ttccatcggc aacttcttgg tgatcttcac catcacctgg | 180 |
| cgacgtcgga ttcaatgctc cggcgatgtt tactttatca acctcgcggc cgccgatttg | 240 |
| cttttcgttt gtacactacc tctgtggatg caatacctcc tagatcacaa ctccctagcc | 300 |
| agcgtgccgt gtacgttact cactgcctgt ttctacgtgg ctatgtttgc cagtttgtgt | 360 |
| tttatcacgg agattgcact cgatcgctac tacgctattg tttacatgag atatcggcct | 420 |
| gtaaaacagg cctgccttttt cagtattttt tggtggatct ttgccgtgat catcgccatt | 480 |
| ccacatttta tggtggtgac caaaaaagac aatcaatgta tgaccgacta cgactactta | 540 |
| gaggtcagct acccgatcat cctcaacgta gaactcatgc tcggtgcttt cgtgatcccg | 600 |
| ctcagtgtca tcagctactg ctactaccgc atttccagaa tcgttgcggt gtctcagtcg | 660 |
| cgccacaaag gtcgcattgt acgggtactt atagcggtcg tgcttgtctt tatcatcttt | 720 |
| tggctgccgt accacctaac gctgtttgtg gacacgttaa aactcctcaa atggatctcc | 780 |
| agcagctgcg agttcgaaag atcgctcaaa cgtgcgctca tcttgaccga gtcgctcgcc | 840 |
| ttttgtcact gttgtctcaa tccgctgctg tacgtcttcg tgggcaccaa gtttcggcaa | 900 |
| gaactgcact gtctgctggc cgagtttcgc cagcgactct ttcccgcga tgtatcctgg | 960 |
| taccacagca tgagcttttc gcgtcggagc tcgccgagcc gaagagagac atcttccgac | 1020 |
| acgctgtccg acgaggtgtg tcgcgtctca caaattatac cgtaa | 1065 |

<210> SEQ ID NO 2
<211> LENGTH: 354
<212> TYPE: PRT
<213> ORGANISM: Human cytomegalovirus
<220> FEATURE:
<223> OTHER INFORMATION: human cytomegalovirus (HCMV) Toledo strain
      open reading frame US28 (AU4.1)

<400> SEQUENCE: 2

Met Thr Pro Thr Thr Thr Thr Ala Glu Leu Thr Glu Phe Asp Tyr
 1               5                  10                  15

Asp Glu Ala Ala Thr Pro Cys Val Phe Thr Asp Val Leu Asn Gln Ser
                20                  25                  30

Lys Pro Val Thr Leu Phe Leu Tyr Gly Val Val Phe Leu Phe Gly Ser
            35                  40                  45

Ile Gly Asn Phe Leu Val Ile Phe Thr Ile Thr Trp Arg Arg Arg Ile
        50                  55                  60

Gln Cys Ser Gly Asp Val Tyr Phe Ile Asn Leu Ala Ala Ala Asp Leu
    65                  70                  75                  80

Leu Phe Val Cys Thr Leu Pro Leu Trp Met Gln Tyr Leu Leu Asp His
                85                  90                  95

Asn Ser Leu Ala Ser Val Pro Cys Thr Leu Leu Thr Ala Cys Phe Tyr
                100                 105                 110

Val Ala Met Phe Ala Ser Leu Cys Phe Ile Thr Glu Ile Ala Leu Asp
            115                 120                 125

Arg Tyr Tyr Ala Ile Val Tyr Met Arg Tyr Arg Pro Val Lys Gln Ala
        130                 135                 140

Cys Leu Phe Ser Ile Phe Trp Trp Ile Phe Ala Val Ile Ile Ala Ile
    145                 150                 155                 160

Pro His Phe Met Val Val Thr Lys Lys Asp Asn Gln Cys Met Thr Asp

```
                   165                 170                 175
Tyr Asp Tyr Leu Glu Val Ser Tyr Pro Ile Ile Leu Asn Val Glu Leu
                180                 185                 190
Met Leu Gly Ala Phe Val Ile Pro Leu Ser Val Ile Ser Tyr Cys Tyr
                195                 200                 205
Tyr Arg Ile Ser Arg Ile Val Ala Val Ser Gln Ser Arg His Lys Gly
                210                 215                 220
Arg Ile Val Arg Val Leu Ile Ala Val Val Leu Val Phe Ile Ile Phe
225                 230                 235                 240
Trp Leu Pro Tyr His Leu Thr Leu Phe Val Asp Thr Leu Lys Leu Leu
                245                 250                 255
Lys Trp Ile Ser Ser Ser Cys Glu Phe Glu Arg Ser Leu Lys Arg Ala
                260                 265                 270
Leu Ile Leu Thr Glu Ser Leu Ala Phe Cys His Cys Cys Leu Asn Pro
                275                 280                 285
Leu Leu Tyr Val Phe Val Gly Thr Lys Phe Arg Gln Glu Leu His Cys
                290                 295                 300
Leu Leu Ala Glu Phe Arg Gln Arg Leu Phe Ser Arg Asp Val Ser Trp
305                 310                 315                 320
Tyr His Ser Met Ser Phe Ser Arg Arg Ser Ser Pro Ser Arg Arg Glu
                325                 330                 335
Thr Ser Ser Asp Thr Leu Ser Asp Glu Val Cys Arg Val Ser Gln Ile
                340                 345                 350
Ile Pro
```

<210> SEQ ID NO 3
<211> LENGTH: 1065
<212> TYPE: DNA
<213> ORGANISM: Human cytomegalovirus
<220> FEATURE:
<223> OTHER INFORMATION: human cytomegalovirus (HCMV) VHL/E strain
      open reading frame US28
<221> NAME/KEY: CDS
<222> LOCATION: (1)..(1065)
<223> OTHER INFORMATION: HCMV VHL/E US28

<400> SEQUENCE: 3

```
atgacaccga cgacgacgac cgcggaactc acgacggagt tgactacga cgatgaagcg      60
actccctgtg tcctcaccga cgtgcttaat cagtcgaagc cagtcacgtt gtttctgtac    120
ggcgttgtct ttctcttcgg ttccatcggc aacttcttgg tgatcttcac catcacctgg    180
cgacgtcgga ttcaatgttc cggcgatgtt tactttatca acctcgcggc cgccgatttg    240
cttttcgttt gtacactacc tctgtggatg caatacctcc tagatcacaa ctccctagcc    300
agcgtgccgt gtacgttact cactgcctgt tctacgtgg ctatgtttgc cagtttgtgt    360
tttatcacgg agattgcact cgatcgctac tacgctattg tttacatgag atatcggcct    420
gtaaaacagg cctgcctttt cagtatttt tggtggatct ttgccgtgat catcgccatt    480
ccacacttta tggtggtgac caaaaaagac aatcaatgta tgaccgacta cgactactta    540
gaggtcagtt acccgatcat cctcaacgta gaactcatgc tcggtgcttt cgtgatcccg    600
ctcagtgtca tcagctactg ctactaccgc atttccagaa tcgttgcggt gtctcagtcg    660
cgccacaaag gccgcattgt acgggtactt atagcggtcg tgcttgtctt tatcatcttt    720
tggctgccgt accacctgac gctgtttgtg gacacgttga aactgctcaa atggatctcc    780
agcagctgcg agttcgaaaa atcactcaag cgcgcgctca tcttgaccga gtcactcgcc    840
```

```
ttttgtcact gttgtctcaa tccgctgctg tacgtcttcg tgggcaccaa gtttcggcaa      900
gaactgcact gtctgctggc cgagtttcgc cagcgactgt tttcccgcga tgtatcctgg      960
taccacagca tgagcttttc gcgtcggagc tcgccgagcc gaagagagac gtcttccgac     1020
acgctgtccg acgaggcgtg tcgcgtctca caaattatac cgtaa                     1065
```

<210> SEQ ID NO 4
<211> LENGTH: 354
<212> TYPE: PRT
<213> ORGANISM: Human cytomegalovirus
<220> FEATURE:
<223> OTHER INFORMATION: human cytomegalovirus (HCMV) VHL/E strain
      open reading frame US28

<400> SEQUENCE: 4

```
Met Thr Pro Thr Thr Thr Thr Ala Glu Leu Thr Thr Glu Phe Asp Tyr
  1               5                  10                  15

Asp Asp Glu Ala Thr Pro Cys Val Leu Thr Asp Val Leu Asn Gln Ser
             20                  25                  30

Lys Pro Val Thr Leu Phe Leu Tyr Gly Val Val Phe Leu Phe Gly Ser
         35                  40                  45

Ile Gly Asn Phe Leu Val Ile Phe Thr Ile Thr Trp Arg Arg Arg Ile
 50                  55                  60

Gln Cys Ser Gly Asp Val Tyr Phe Ile Asn Leu Ala Ala Ala Asp Leu
 65                  70                  75                  80

Leu Phe Val Cys Thr Leu Pro Leu Trp Met Gln Tyr Leu Leu Asp His
                 85                  90                  95

Asn Ser Leu Ala Ser Val Pro Cys Thr Leu Leu Thr Ala Cys Phe Tyr
            100                 105                 110

Val Ala Met Phe Ala Ser Leu Cys Phe Ile Thr Glu Ile Ala Leu Asp
        115                 120                 125

Arg Tyr Tyr Ala Ile Val Tyr Met Arg Tyr Arg Pro Val Lys Gln Ala
    130                 135                 140

Cys Leu Phe Ser Ile Phe Trp Trp Ile Phe Ala Val Ile Ile Ala Ile
145                 150                 155                 160

Pro His Phe Met Val Val Thr Lys Lys Asp Asn Gln Cys Met Thr Asp
                165                 170                 175

Tyr Asp Tyr Leu Glu Val Ser Tyr Pro Ile Ile Leu Asn Val Glu Leu
            180                 185                 190

Met Leu Gly Ala Phe Val Ile Pro Leu Ser Val Ile Ser Tyr Cys Tyr
        195                 200                 205

Tyr Arg Ile Ser Arg Ile Val Ala Val Ser Gln Ser Arg His Lys Gly
    210                 215                 220

Arg Ile Val Arg Val Leu Ile Ala Val Val Leu Val Phe Ile Ile Phe
225                 230                 235                 240

Trp Leu Pro Tyr His Leu Thr Leu Phe Val Asp Thr Leu Lys Leu Leu
                245                 250                 255

Lys Trp Ile Ser Ser Ser Cys Glu Phe Glu Lys Ser Leu Lys Arg Ala
            260                 265                 270

Leu Ile Leu Thr Glu Ser Leu Ala Phe Cys His Cys Cys Leu Asn Pro
        275                 280                 285

Leu Leu Tyr Val Phe Val Gly Thr Lys Phe Arg Gln Glu Leu His Cys
    290                 295                 300

Leu Leu Ala Glu Phe Arg Gln Arg Leu Phe Ser Arg Asp Val Ser Trp
305                 310                 315                 320
```

-continued

```
Tyr His Ser Met Ser Phe Ser Arg Arg Ser Ser Pro Ser Arg Arg Glu
            325                 330                 335

Thr Ser Ser Asp Thr Leu Ser Asp Glu Ala Cys Arg Val Ser Gln Ile
        340                 345                 350

Ile Pro
```

<210> SEQ ID NO 5
<211> LENGTH: 1020
<212> TYPE: DNA
<213> ORGANISM: Rhesus cytomegalovirus
<220> FEATURE:
<223> OTHER INFORMATION: rhesus monkey cytomegalovirus (rhCMV) US28 homolog rhUS28.1
<221> NAME/KEY: CDS
<222> LOCATION: (1)..(1020)
<223> OTHER INFORMATION: rhUS28.1

<400> SEQUENCE: 5

```
atgaataaca catcttgcaa cttcaacgtc actctcaacg catcggcacc aagccgatac     60
atagctattg ctatgtacag cattgttatc tgtatcgggt tggttggaaa cctgctgtta    120
tgcatcgtgt tagtcaagaa acgcaaactg cgatattcca gcgatgttta tttttttccac   180
gcctctatgg ccgacctcgt cagcactgtc atgctaccgc tctggctaca ttatgtcctc    240
aactttgccc aactctctcg aggagcctgt atcagctttt cggtgacttt ctatgttccc    300
cttttcgttc aggcctggtt actcatttcc atcgctatgg agcgatattc aacttagta    360
tggatggcac ccattagcgt taagacggcc tttaaacact gcataggaac ctggatcgta    420
tctgccttcg tggcatcacc ctactacgca tacagaaact cacacgacga cacgaatgc    480
attctaggaa actacacttg gcacattaac gaaccgctac acacgtgtat ggatgtggtg    540
atcatagtat ggaccttttt ggccccagta ctggtaacca ttatagcaag cgtcaaaatg    600
agacgaacga cctggggcaa tactaggtta acgaaaaga acagcgacat tcttatagta    660
ctagttgtca tgacagtgtt cttttgggga ccgtttaata tcgtgttggt tattgacaat    720
attttacaga gatactatga taccacgaat tgcgatgtag aaaagattaa acatatcatg    780
gctatgatct cagaagccat tgtttatttt cgcggtatta cagcacctat tatttatgta    840
gggattagtg gcagatttcg cgaagagatt tactctctgt ttagacgcca gccgtataac    900
gatttggacc ccgatgccaa tcaattcatg attgaactca ctagccaggg aagaagtaga    960
aatagaaatg ctagacaatc ggaaagcaat gtaccgcaac agaagaatg cttctggtaa   1020
```

<210> SEQ ID NO 6
<211> LENGTH: 339
<212> TYPE: PRT
<213> ORGANISM: Rhesus cytomegalovirus
<220> FEATURE:
<223> OTHER INFORMATION: rhesus monkey cytomegalovirus (rhCMV) US28 homolog rhUS28.1

<400> SEQUENCE: 6

```
Met Asn Asn Thr Ser Cys Asn Phe Asn Val Thr Leu Asn Ala Ser Ala
  1               5                  10                  15

Pro Ser Arg Tyr Ile Ala Ile Ala Met Tyr Ser Ile Val Ile Cys Ile
                20                  25                  30

Gly Leu Val Gly Asn Leu Leu Leu Cys Ile Val Leu Val Lys Lys Arg
            35                  40                  45

Lys Leu Arg Tyr Ser Ser Asp Val Tyr Phe Phe His Ala Ser Met Ala
        50                  55                  60
```

```
Asp Leu Val Ser Thr Val Met Leu Pro Leu Trp Leu His Tyr Val Leu
 65                  70                  75                  80

Asn Phe Ala Gln Leu Ser Arg Gly Ala Cys Ile Ser Phe Ser Val Thr
                 85                  90                  95

Phe Tyr Val Pro Leu Phe Val Gln Ala Trp Leu Leu Ile Ser Ile Ala
            100                 105                 110

Met Glu Arg Tyr Ser Asn Leu Val Trp Met Ala Pro Ile Ser Val Lys
        115                 120                 125

Thr Ala Phe Lys His Cys Ile Gly Thr Trp Ile Val Ser Ala Phe Val
130                 135                 140

Ala Ser Pro Tyr Tyr Ala Tyr Arg Asn Ser His Asp Glu His Glu Cys
145                 150                 155                 160

Ile Leu Gly Asn Tyr Thr Trp His Ile Asn Glu Pro Leu His Thr Cys
                165                 170                 175

Met Asp Val Val Ile Ile Val Trp Thr Phe Leu Ala Pro Val Leu Val
            180                 185                 190

Thr Ile Ile Ala Ser Val Lys Met Arg Arg Thr Thr Trp Gly Asn Thr
        195                 200                 205

Arg Leu Asn Glu Lys Asn Ser Asp Ile Leu Ile Val Leu Val Val Met
210                 215                 220

Thr Val Phe Phe Trp Gly Pro Phe Asn Ile Val Leu Val Ile Asp Asn
225                 230                 235                 240

Ile Leu Gln Arg Tyr Tyr Asp Thr Thr Asn Cys Asp Val Glu Lys Ile
                245                 250                 255

Lys His Ile Met Ala Met Ile Ser Glu Ala Ile Val Tyr Phe Arg Gly
            260                 265                 270

Ile Thr Ala Pro Ile Ile Tyr Val Gly Ile Ser Gly Arg Phe Arg Glu
        275                 280                 285

Glu Ile Tyr Ser Leu Phe Arg Arg Gln Pro Tyr Asn Asp Leu Asp Pro
290                 295                 300

Asp Ala Asn Gln Phe Met Ile Glu Leu Thr Ser Gln Gly Arg Ser Arg
305                 310                 315                 320

Asn Arg Asn Ala Arg Gln Ser Glu Ser Asn Val Pro Gln Pro Glu Glu
                325                 330                 335

Cys Phe Trp

<210> SEQ ID NO 7
<211> LENGTH: 1002
<212> TYPE: DNA
<213> ORGANISM: Rhesus cytomegalovirus
<220> FEATURE:
<223> OTHER INFORMATION: rhesus monkey cytomegalovirus (rhCMV) US28
      homolog rhUS28.2
<221> NAME/KEY: CDS
<222> LOCATION: (1)..(1002)
<223> OTHER INFORMATION: rhUS28.2

<400> SEQUENCE: 7
atgaccaacg ccggacactg tcacataaac gaaagtctcg cgtcgtatgg aatcgctccc      60
gcagctacca ttaccttata cagcattgcg ggaatctgcg gtgtcacggg aaatctgtta     120
atacttttgg ttttgttcac gagacgcata cactggttcg caaatgacat ctactatctc     180
aacatgatct ttacagactt tcttgttttc attacattac ccgcctgggt ttactacctg     240
ctgaattaca cacaactctc acactatgcc tgcattgctc tatcatttgt tttttacgtt     300 tccatttta ttcaagctga ctttatggta gcagtggcta tcgagcgtta tcgaagccta     360
```

```
gtgaaaaaca aacccottag cgtaaaaaaa gocagcgtca gotgogcgtg catotggatc    420 attgttatta tagtgtcttc accatactac atgtttagat cgcaacacga aacaaattct    480
tgcattctag gaaactacac ctggcatatg aacagtcctt ttcgcaccac aatggacgca    540
tccattaaca tttggtcttt tgtcgttccg gccgtgacga ccttgttaat agccagacga    600
atttatgtat gtacttcagg caacaaaaaa atgaacgcca gagccagtgg tttgttagag    660
gccatggtga ttagcatgtt attcttcgga ggacttttca acctgaacat ctttcgagac    720
atagtttcgg acacatcgga agacaataaa gactgcacat atcttaagca ggaaacttt     780 attcgcatgg tcggtgtggc cctcgtttac gggcgcgcta tattcaaccc tttatgtat    840 atgtgtgtga gtaccagatt gcgccaagaa ataaaatgtt tgtttatgcg aataccttat    900
gaaacactag atgcagaaca cgctaaactc atggttaatt taaaaacag aaatgctaat    960 gtacccgatc ctaaacctcg tgaatatgaa tctgtgttat ag                      1002
```

<210> SEQ ID NO 8
<211> LENGTH: 333
<212> TYPE: PRT
<213> ORGANISM: Rhesus cytomegalovirus
<220> FEATURE:
<223> OTHER INFORMATION: rhesus monkey cytomegalovirus (rhCMV) US28
    homolog rhUS28.2

<400> SEQUENCE: 8

Met Thr Asn Ala Gly His Cys His Ile Asn Glu Ser Leu Ala Ser Tyr
1               5                   10                  15

Gly Ile Ala Pro Ala Ala Thr Ile Thr Leu Tyr Ser Ile Ala Gly Ile
                20                  25                  30

Cys Gly Val Thr Gly Asn Leu Leu Ile Leu Leu Val Leu Phe Thr Arg
            35                  40                  45

Arg Ile His Trp Phe Ala Asn Asp Ile Tyr Tyr Leu Asn Met Ile Phe
        50                  55                  60

Thr Asp Phe Leu Val Phe Ile Thr Leu Pro Ala Trp Val Tyr Tyr Leu
65                  70                  75                  80

Leu Asn Tyr Thr Gln Leu Ser His Tyr Ala Cys Ile Ala Leu Ser Phe
                85                  90                  95

Val Phe Tyr Val Ser Ile Phe Ile Gln Ala Asp Phe Met Val Ala Val
                100                 105                 110

Ala Ile Glu Arg Tyr Arg Ser Leu Val Lys Asn Lys Pro Leu Ser Val
            115                 120                 125

Lys Lys Ala Ser Val Ser Cys Ala Cys Ile Trp Ile Ile Val Ile Ile
        130                 135                 140

Val Ser Ser Pro Tyr Tyr Met Phe Arg Ser Gln His Glu Thr Asn Ser
145                 150                 155                 160

Cys Ile Leu Gly Asn Tyr Thr Trp His Met Asn Ser Pro Phe Arg Thr
                165                 170                 175

Thr Met Asp Ala Ser Ile Asn Ile Trp Ser Phe Val Val Pro Ala Val
            180                 185                 190

Thr Thr Leu Leu Ile Ala Arg Arg Ile Tyr Val Cys Thr Ser Gly Asn
        195                 200                 205

Lys Lys Met Asn Ala Arg Ala Ser Gly Leu Leu Glu Ala Met Val Ile
    210                 215                 220

Ser Met Leu Phe Phe Gly Gly Leu Phe Asn Leu Asn Ile Phe Arg Asp
225                 230                 235                 240

Ile Val Ser Asp Thr Ser Glu Asp Asn Lys Asp Cys Thr Tyr Leu Lys

```
                245             250             255
Gln Glu His Phe Ile Arg Met Val Gly Val Ala Leu Val Tyr Gly Arg
        260             265             270
Ala Ile Phe Asn Pro Phe Met Tyr Met Cys Val Ser Thr Arg Leu Arg
        275             280             285
Gln Glu Ile Lys Cys Leu Phe Met Arg Ile Pro Tyr Glu Thr Leu Asp
        290             295             300
Ala Glu His Ala Lys Leu Met Val Asn Leu Lys Asn Arg Asn Ala Asn
305             310             315             320
Val Pro Asp Pro Lys Pro Arg Glu Tyr Glu Ser Val Leu
        325             330

<210> SEQ ID NO 9
<211> LENGTH: 1014
<212> TYPE: DNA
<213> ORGANISM: Rhesus cytomegalovirus
<220> FEATURE:
<223> OTHER INFORMATION: rhesus monkey cytomegalovirus (rhCMV) US28
      homolog rhUS28.3
<221> NAME/KEY: CDS
<222> LOCATION: (1)..(1014)
<223> OTHER INFORMATION: rhUS28.3

<400> SEQUENCE: 9
atgaccaaca ctaacaatac gacttgtcat ctcaacggaa ctttcgaaac ttttaaaatc      60
acccgtccag tagccatcag cgcctacact gtactcgtgg ttatcggact tttgggaaac    120
attgtgctgc tcagcgtgct cgtcgtgaaa cgcaagctca agtttccgaa tgacatttac    180
tttttcaacg cgtctttggc agacgttttt gccgtctgca tgttgcccgc ctgggttaac    240
tatgcactgg actccacaca acttagcaag ttctcatgta tcacttttac gtttggtttt    300
tacgtctccc tgttcatcca ggcctggatg ctcattctgg tcaccctgga gcgatacgga    360
tctctagtct ggatcgcccc gatcaccaga aacaaagcca tagcgaattg tgtactcttt    420
tggcttgttt ccatcttctt ggccgcacct tactactctt ttagaaacga agcaacgaa     480 caccaatgca tcatgagaaa ctatacctgg agcgttggtg aaacatggca catagccctg    540
gatttcttaa ttacgctcat tacatttatc atgccagtga ctattgtgtt agctctgagt    600
ttcaaaatgg ccagatggtc aacctttggt tacagaaacc tcaccagcag aaccagtctt    660
atccttattt tgatactgac agtagcagca gggttctggg gaccttttca cctatttatg    720
tttatagaaa acgtggcagg gcagatttac cacattcaaa aggattgctg gtacttacag    780
ctcagacact tgtgtagctt gatgaccgaa accctagtgt ttctacgttc agttttttaac    840 ccttatattt atatgataat cagttacaag tttaggcagc aggtgcgcag tctactcaag    900
cgtactcagt atgatgcttt ggacacgact cagttagcag aaactatgca gctgaaagcg    960
aaaggtgtgc cggtgtccga ccccgcgccg catgactgcg aatgcttttt gtaa         1014

<210> SEQ ID NO 10
<211> LENGTH: 337
<212> TYPE: PRT
<213> ORGANISM: Rhesus cytomegalovirus
<220> FEATURE:
<223> OTHER INFORMATION: rhesus monkey cytomegalovirus (rhCMV) US28
      homolog rhUS28.3

<400> SEQUENCE: 10

Met Thr Asn Thr Asn Asn Thr Thr Cys His Leu Asn Gly Thr Phe Glu
1               5                   10                  15
```

```
Thr Phe Lys Ile Thr Arg Pro Val Ala Ile Ser Ala Tyr Thr Val Leu
             20                  25                  30
Val Val Ile Gly Leu Leu Gly Asn Ile Val Leu Leu Ser Val Leu Val
         35                  40                  45
Val Lys Arg Lys Leu Lys Phe Pro Asn Asp Ile Tyr Phe Phe Asn Ala
 50                  55                  60
Ser Leu Ala Asp Val Phe Ala Val Cys Met Leu Pro Ala Trp Val Asn
 65                  70                  75                  80
Tyr Ala Leu Asp Ser Thr Gln Leu Ser Lys Phe Ser Cys Ile Thr Phe
                 85                  90                  95
Thr Phe Gly Phe Tyr Val Ser Leu Phe Ile Gln Ala Trp Met Leu Ile
            100                 105                 110
Leu Val Thr Leu Glu Arg Tyr Gly Ser Leu Val Trp Ile Ala Pro Ile
        115                 120                 125
Thr Arg Asn Lys Ala Ile Ala Asn Cys Val Leu Phe Trp Leu Val Ser
130                 135                 140
Ile Phe Leu Ala Ala Pro Tyr Tyr Ser Phe Arg Asn Glu Ser Asn Glu
145                 150                 155                 160
His Gln Cys Ile Met Arg Asn Tyr Thr Trp Ser Val Gly Glu Thr Trp
                165                 170                 175
His Ile Ala Leu Asp Phe Leu Ile Thr Leu Ile Thr Phe Ile Met Pro
            180                 185                 190
Val Thr Ile Val Leu Ala Leu Ser Phe Lys Met Ala Arg Trp Ser Thr
        195                 200                 205
Phe Gly Tyr Arg Asn Leu Thr Ser Arg Thr Ser Leu Ile Leu Ile Leu
210                 215                 220
Ile Leu Thr Val Ala Ala Gly Phe Trp Gly Pro Phe His Leu Phe Met
225                 230                 235                 240
Phe Ile Glu Asn Val Ala Gly Gln Ile Tyr His Ile Gln Lys Asp Cys
                245                 250                 255
Trp Tyr Leu Gln Leu Arg His Leu Cys Ser Leu Met Thr Glu Thr Leu
            260                 265                 270
Val Phe Leu Arg Ser Val Phe Asn Pro Tyr Ile Tyr Met Ile Ile Ser
        275                 280                 285
Tyr Lys Phe Arg Gln Gln Val Arg Ser Leu Leu Lys Arg Thr Gln Tyr
290                 295                 300
Asp Ala Leu Asp Thr Thr Gln Leu Ala Glu Thr Met Gln Leu Lys Ala
305                 310                 315                 320
Lys Gly Val Pro Val Ser Asp Pro Ala Pro His Asp Cys Glu Cys Phe
                325                 330                 335
Leu
```

<210> SEQ ID NO 11
<211> LENGTH: 987
<212> TYPE: DNA
<213> ORGANISM: Rhesus cytomegalovirus
<220> FEATURE:
<223> OTHER INFORMATION: rhesus monkey cytomegalovirus (rhCMV) US28 homolog rhUS28.4
<221> NAME/KEY: CDS
<222> LOCATION: (1)..(987)
<223> OTHER INFORMATION: rhUS28.4

<400> SEQUENCE: 11

```
atgaattcga gccagcacaa cataagcgtg tttctctcca ttggagcagg gcccgtcatt    60
accggataca cgtgcgtttt tctgttcggg attctggac acttttactt gtattggaaa   120
```

-continued

```
aaccatcaga gacgacaccg gacaaacagt ttcagtgatg ttttatttcg acatctcatg    180
atcaccgaag aggtctttac cctcaccatt cccgtctggg cgtatcactt aactactcac    240
ggcaacttac cgggctcgtg gtgccgaagt ctcaccttcg tttttttatct aacggtattc    300 gctcgtgcct tcttttacct gctcctcatc tgggaccgat acagcgtaat catctgcaga    360
caccctctcc ccgttaatct gaactacagt caggtcatag gcctgtctgt ctggctggtt    420
gccgtactgt cagcatcacc gttctccatt tttaacgaa gtgtgaaaca atgcctgggc    480
aacatgggca gcatacccag cgaatcgtct gccgttctta acctggaagt gcacctgtgc    540
tccttctggt taccgctcat catgtcggct aactgttact accaagcaaa acgccgagca    600
tcgcctgacc aactccacga actttaccga tgcagtttgc taattaccat tatcacaact    660
tacgctatcg tatggtttcc tttccatctc gctttactca tagacgccct gattagcata    720
agccatgtag aaccctctag cgctctccac tgggcatcca ttgtcgttac ctgtaaatca    780
tttacatttg tatatgcggg cataagccca ctagtgtatt tcacatgctg ccccaccgta    840
cgtcgcgaac tgctgatgtc tctacgtcca ttcttcacct ggatttccag caaaacgcgg    900
cgaggctacg ctccgattaa aacacaacct ttaaacatcc ccgacgagcc gatagataac    960
aagtcaccgc acctgttaaa cgaataa                                        987
```

```
<210> SEQ ID NO 12
<211> LENGTH: 328
<212> TYPE: PRT
<213> ORGANISM: Rhesus cytomegalovirus
<220> FEATURE:
<223> OTHER INFORMATION: rhesus monkey cytomegalovirus (rhCMV) US28
      homolog rhUS28.4

<400> SEQUENCE: 12

Met Asn Ser Ser Gln His Asn Ile Ser Val Phe Leu Ser Ile Gly Ala
  1               5                  10                  15

Gly Pro Val Ile Thr Gly Tyr Thr Cys Val Phe Leu Phe Gly Ile Leu
             20                  25                  30

Gly His Phe Tyr Leu Tyr Trp Lys Asn His Gln Arg Arg His Arg Thr
         35                  40                  45

Asn Ser Phe Ser Asp Val Leu Phe Arg His Leu Met Ile Thr Glu Glu
     50                  55                  60

Val Phe Thr Leu Thr Ile Pro Val Trp Ala Tyr His Leu Thr Thr His
 65                  70                  75                  80

Gly Asn Leu Pro Gly Ser Trp Cys Arg Ser Leu Thr Phe Val Phe Tyr
                 85                  90                  95

Leu Thr Val Phe Ala Arg Ala Phe Phe Tyr Leu Leu Leu Ile Trp Asp
            100                 105                 110

Arg Tyr Ser Val Ile Ile Cys Arg His Pro Leu Pro Val Asn Leu Asn
        115                 120                 125

Tyr Ser Gln Val Ile Gly Leu Ser Val Trp Leu Val Ala Val Leu Ser
    130                 135                 140

Ala Ser Pro Phe Ser Ile Phe Asn Gly Ser Val Lys Gln Cys Leu Gly
145                 150                 155                 160

Asn Met Gly Ser Ile Pro Ser Glu Ser Ala Val Leu Asn Leu Glu
                165                 170                 175

Val His Leu Cys Ser Phe Trp Leu Pro Leu Ile Met Ser Ala Asn Cys
            180                 185                 190

Tyr Tyr Gln Ala Lys Arg Arg Ala Ser Pro Asp Gln Leu His Glu Leu
```

```
                195             200             205
Tyr Arg Cys Ser Leu Leu Ile Thr Ile Ile Thr Tyr Ala Ile Val
    210             215             220

Trp Phe Pro Phe His Leu Ala Leu Leu Ile Asp Ala Leu Ile Ser Ile
225             230             235             240

Ser His Val Glu Pro Ser Ser Ala Leu His Trp Ala Ser Ile Val Val
            245             250             255

Thr Cys Lys Ser Phe Thr Phe Val Tyr Ala Gly Ile Ser Pro Leu Val
            260             265             270

Tyr Phe Thr Cys Cys Pro Thr Val Arg Arg Glu Leu Leu Met Ser Leu
            275             280             285

Arg Pro Phe Phe Thr Trp Ile Ser Ser Lys Thr Arg Arg Gly Tyr Ala
    290             295             300

Pro Ile Lys Thr Gln Pro Leu Asn Ile Pro Asp Glu Pro Ile Asp Asn
305             310             315             320

Lys Ser Pro His Leu Leu Asn Glu
            325

<210> SEQ ID NO 13
<211> LENGTH: 1452
<212> TYPE: DNA
<213> ORGANISM: Rhesus cytomegalovirus
<220> FEATURE:
<223> OTHER INFORMATION: rhesus monkey cytomegalovirus (rhCMV) US28
      homolog rhUS28.5
<221> NAME/KEY: CDS
<222> LOCATION: (1)..(1452)
<223> OTHER INFORMATION: rhUS28.5

<400> SEQUENCE: 13
atgactacca ccacaatgag tgctaccacg aattccagta ccacgcctca agcaagcagc      60
accacgatga caacgaagac aagcactcct ggcaatacaa ctactggcac tacgtccacc     120
ctgacaacga tatcaacaac ttctaatgct accagcataa cgtctaattt aagcactacc     180
ggaaaccaaa ctgcaactac caatgctact accttcagtt ccacattaac aacatctaca     240
aatataagca gtacattttc gacagtttct accgtcgcat ccaatgcaac atgtaattct     300
acaatcacaa cgaatattac aactgctttt actacagcag caaacactac cgcaagcagc     360
ctcaccagca tcgtaacttc acttgccact accattgaaa ccacatcatt tgattatgat     420
gagtcagcag aagcttgcaa cttaacagac atcgttcata ctactagatc agtgacagtt     480
actttctata ctatcatatt catactcggc cttttgggaa actttctggt tcttatgacc     540
atcatttgga accgtcgcat ttcctttatg gttgaaatat atttcgttaa tctagcaatc     600
tccgatctta tgtttgtatg tactttacca ttttggataa tgtatcttct tgagcacgac     660
gtcatgtcac atgcatcctg tgtagcaatg acagccattt tttattgcgc gctgtttgcc     720
agcactgttt cctcttgct aattgtttta gacagatgtt acgctattct attaggtaca     780
gaaaaagcaa atagacgttt attgcgcaat gctgtttctg atgcatgct catgtgggga     840 ttgtgtttca ttttagcatt acctcatttt atctttatga agaaaggaac caacgtatgt     900
gtagcagagt atgaaccagg acttaacaat ttctatgtta ttttttatcaa tactgaggtg     960 aacctatgca cctagttttt gccagccgca gccattatct actggtatct taaactaacc    1020 aaaagcactca aaacccatga cgactgcgt cataggctaa cgtctctaaa catagtgtta    1080
gctgttgtca ttgtatttgc tttgtttttgg ctgccgtata atctcatgct tatgatgtat    1140
agcttagttc acatgcagat accttgggaa tgcagctctg aaaaaatact gagacgaagt    1200
```

-continued

```
ttaattatta cagaatccat cgccctcagt cactgttgca tcaacccat tatctacttg    1260 ctcttcggac ctcgctgtcg aagcgagttc tgtcacctgt tgcgatgttg ctttacgcgc    1320
ttatgtccac acagatcctg gagttccata cgtgcagaga cggtgtccat cagtctcagt    1380
cactcacagg tatctgcatc atctgaggat gatgacaacg atgtgcatga tgaattgcaa    1440
tttttaattt ga                                                       1452
```

<210> SEQ ID NO 14
<211> LENGTH: 483
<212> TYPE: PRT
<213> ORGANISM: Rhesus cytomegalovirus
<220> FEATURE:
<223> OTHER INFORMATION: rhesus monkey cytomegalovirus (rhCMV) US28 homolog rhUS28.5

<400> SEQUENCE: 14

```
Met Thr Thr Thr Thr Met Ser Ala Thr Thr Asn Ser Ser Thr Thr Pro
  1               5                  10                  15

Gln Ala Ser Ser Thr Thr Met Thr Thr Lys Thr Ser Thr Pro Gly Asn
             20                  25                  30

Thr Thr Thr Gly Thr Thr Ser Thr Leu Thr Thr Ile Ser Thr Thr Ser
         35                  40                  45

Asn Ala Thr Ser Ile Thr Ser Asn Leu Ser Thr Thr Gly Asn Gln Thr
     50                  55                  60

Ala Thr Thr Asn Ala Thr Thr Phe Ser Ser Thr Leu Thr Thr Ser Thr
 65                  70                  75                  80

Asn Ile Ser Ser Thr Phe Ser Thr Val Ser Thr Val Ala Ser Asn Ala
                 85                  90                  95

Thr Cys Asn Ser Thr Ile Thr Thr Asn Ile Thr Thr Ala Phe Thr Thr
            100                 105                 110

Ala Ala Asn Thr Thr Ala Ser Ser Leu Thr Ser Ile Val Thr Ser Leu
        115                 120                 125

Ala Thr Thr Ile Glu Thr Thr Ser Phe Asp Tyr Asp Glu Ser Ala Glu
    130                 135                 140

Ala Cys Asn Leu Thr Asp Ile Val His Thr Thr Arg Ser Val Thr Val
145                 150                 155                 160

Thr Phe Tyr Thr Ile Ile Phe Ile Leu Gly Leu Leu Gly Asn Phe Leu
                165                 170                 175

Val Leu Met Thr Ile Ile Trp Asn Arg Arg Ile Ser Phe Met Val Glu
            180                 185                 190

Ile Tyr Phe Val Asn Leu Ala Ile Ser Asp Leu Met Phe Val Cys Thr
        195                 200                 205

Leu Pro Phe Trp Ile Met Tyr Leu Leu Glu His Asp Val Met Ser His
    210                 215                 220

Ala Ser Cys Val Ala Met Thr Ala Ile Phe Tyr Cys Ala Leu Phe Ala
225                 230                 235                 240

Ser Thr Val Phe Leu Leu Leu Ile Val Leu Asp Arg Cys Tyr Ala Ile
                245                 250                 255

Leu Leu Gly Thr Glu Lys Ala Asn Arg Arg Leu Leu Arg Asn Ala Val
            260                 265                 270

Ser Gly Cys Met Leu Met Trp Gly Leu Cys Phe Ile Leu Ala Leu Pro
        275                 280                 285

His Phe Ile Phe Met Lys Lys Gly Thr Asn Val Cys Val Ala Glu Tyr
    290                 295                 300
```

```
Glu Pro Gly Leu Asn Asn Phe Tyr Val Ile Phe Ile Asn Thr Glu Val
305                 310                 315                 320
Asn Leu Cys Thr Leu Val Leu Pro Ala Ala Ala Ile Ile Tyr Trp Tyr
                325                 330                 335
Leu Lys Leu Thr Lys Ala Leu Lys Thr His Glu Arg Leu Arg His Arg
            340                 345                 350
Leu Thr Ser Leu Asn Ile Val Leu Ala Val Ile Val Phe Ala Leu
        355                 360                 365
Phe Trp Leu Pro Tyr Asn Leu Met Leu Met Met Tyr Ser Leu Val His
    370                 375                 380
Met Gln Ile Pro Trp Glu Cys Ser Ser Glu Lys Ile Leu Arg Arg Ser
385                 390                 395                 400
Leu Ile Ile Thr Glu Ser Ile Ala Leu Ser His Cys Cys Ile Asn Pro
                405                 410                 415
Ile Ile Tyr Leu Leu Phe Gly Pro Arg Cys Arg Ser Glu Phe Cys His
            420                 425                 430
Leu Leu Arg Cys Cys Phe Thr Arg Leu Cys Pro His Arg Ser Trp Ser
        435                 440                 445
Ser Ile Arg Ala Glu Thr Val Ser Ile Ser Leu Ser His Ser Gln Val
    450                 455                 460
Ser Ala Ser Ser Glu Asp Asp Asp Asn Asp Val His Asp Glu Leu Gln
465                 470                 475                 480

Phe Leu Ile

<210> SEQ ID NO 15
<211> LENGTH: 1296
<212> TYPE: DNA
<213> ORGANISM: Human cytomegalovirus
<220> FEATURE:
<223> OTHER INFORMATION: human cytomegalovirus (HCMV) AD169 strain
      open reading frame UL78
<221> NAME/KEY: CDS
<222> LOCATION: (1)..(1296)
<223> OTHER INFORMATION: HCMV AD169 UL78

<400> SEQUENCE: 15
atgtcccctt ctgtggagga gactacctca gtcaccgagt ccatcatgtt cgctattgtg    60
agtttcaaac acatgggccc gttcgaaggc tactctatgt cggccgatcg cgccgcctcg   120
gatctactca tcggcatgtt cggctccgtt agcctggtca acctgctgac tatcatcggt   180
tgcctctggg tgttgcgtgt tacgcggccg cccgtgtccg tgatgatttt tacttggaat   240
ctggtactta gtcagttttt ttccatcctg gccaccatgt tgtccaaggg tatcatgctg   300
cgtggcgctc taaatctcag cctctgtcgc ttagtgctct ttgtcgacga cgtgggccta   360
tattcgacgg cgttgttttt cctctttctg atactggatc gtctgtcggc catatcttac   420
ggccgtgatc tctggcatca tgagacgcgc gaaaacgccg gcgtggcgct ctacgcggtc   480
gcctttgcct gggttctttc catcgtagcc gctgtgccca ccgccgctac gggttcactg   540
gactaccgtt ggctaggctg tcagatccct atacagtatg ccgcggtgga cctcaccatc   600
aagatgtggt ttttgctggg ggcgcccatg atcgccgtac tggctaacgt ggtagagttg   660
gcctacagcg atcggcgcga ccacgtctgg tcctacgtgg tcgtgtctg caccttctac   720
gtgacgtgtc tcatgctgtt tgtgcccta ctgcttca gagtcctacg cggtgtactg   780
cagcccgcta gcgcggccgg caccggtttc ggcattatgg attacgtgga attggctacg   840
cgtaccctc tcaccatgcg tcttggcatt ctgccgctct ttatcattgc gttcttctcc   900
```

```
cgcgagccca ccaaggatct ggatgactcc tttgattatc tggtcgagag atgtcagcaa    960
agctgccacg tcatttcgt acgtcggttg gtgcaggcgt tgaagcgggc tatgtatagc   1020
gtggagctgg ccgtgtgtta ctttctacg tccgtccgag acgtcgccga ggcggtgaaa   1080
aagtcctcca gccgttgtta cgccgacgcg acgtcggcgg ccgttgtggt aacgacaacc   1140
acgtcggaga agccacgtt ggtggagcac gcggaaggca tggcttccga aatgtgtcct   1200
gggactacga tcgatgtttc ggccgaaagt tcctccgtcc tctgcaccga cggcgaaaac   1260
accgtcgcgt cggacgcgac ggtgacggca ttatga                            1296
```

<210> SEQ ID NO 16
<211> LENGTH: 431
<212> TYPE: PRT
<213> ORGANISM: Human cytomegalovirus
<220> FEATURE:
<223> OTHER INFORMATION: human cytomegalovirus (HCMV) AD169 strain
      open reading frame UL78

<400> SEQUENCE: 16

```
Met Ser Pro Ser Val Glu Glu Thr Thr Ser Val Thr Glu Ser Ile Met
  1               5                  10                  15

Phe Ala Ile Val Ser Phe Lys His Met Gly Pro Phe Glu Gly Tyr Ser
                 20                  25                  30

Met Ser Ala Asp Arg Ala Ala Ser Asp Leu Leu Ile Gly Met Phe Gly
             35                  40                  45

Ser Val Ser Leu Val Asn Leu Leu Thr Ile Ile Gly Cys Leu Trp Val
         50                  55                  60

Leu Arg Val Thr Arg Pro Pro Val Ser Val Met Ile Phe Thr Trp Asn
 65                  70                  75                  80

Leu Val Leu Ser Gln Phe Phe Ser Ile Leu Ala Thr Met Leu Ser Lys
                 85                  90                  95

Gly Ile Met Leu Arg Gly Ala Leu Asn Leu Ser Leu Cys Arg Leu Val
                100                 105                 110

Leu Phe Val Asp Asp Val Gly Leu Tyr Ser Thr Ala Leu Phe Phe Leu
            115                 120                 125

Phe Leu Ile Leu Asp Arg Leu Ser Ala Ile Ser Tyr Gly Arg Asp Leu
        130                 135                 140

Trp His His Glu Thr Arg Glu Asn Ala Gly Val Ala Leu Tyr Ala Val
145                 150                 155                 160

Ala Phe Ala Trp Val Leu Ser Ile Val Ala Ala Val Pro Thr Ala Ala
                165                 170                 175

Thr Gly Ser Leu Asp Tyr Arg Trp Leu Gly Cys Gln Ile Pro Ile Gln
            180                 185                 190

Tyr Ala Ala Val Asp Leu Thr Ile Lys Met Trp Phe Leu Leu Gly Ala
        195                 200                 205

Pro Met Ile Ala Val Leu Ala Asn Val Val Glu Leu Ala Tyr Ser Asp
    210                 215                 220

Arg Arg Asp His Val Trp Ser Tyr Val Gly Arg Val Cys Thr Phe Tyr
225                 230                 235                 240

Val Thr Cys Leu Met Leu Phe Val Pro Tyr Tyr Cys Phe Arg Val Leu
                245                 250                 255

Arg Gly Val Leu Gln Pro Ala Ser Ala Ala Gly Thr Gly Phe Gly Ile
            260                 265                 270

Met Asp Tyr Val Glu Leu Ala Thr Arg Thr Leu Leu Thr Met Arg Leu
        275                 280                 285
```

```
Gly Ile Leu Pro Leu Phe Ile Ile Ala Phe Phe Ser Arg Glu Pro Thr
        290                 295                 300

Lys Asp Leu Asp Asp Ser Phe Asp Tyr Leu Val Glu Arg Cys Gln Gln
305                 310                 315                 320

Ser Cys His Gly His Phe Val Arg Arg Leu Val Gln Ala Leu Lys Arg
                325                 330                 335

Ala Met Tyr Ser Val Glu Leu Ala Val Cys Tyr Phe Ser Thr Ser Val
            340                 345                 350

Arg Asp Val Ala Glu Ala Val Lys Lys Ser Ser Arg Cys Tyr Ala
        355                 360                 365

Asp Ala Thr Ser Ala Ala Val Val Thr Thr Thr Thr Ser Glu Lys
    370                 375                 380

Ala Thr Leu Val Glu His Ala Glu Gly Met Ala Ser Glu Met Cys Pro
385                 390                 395                 400

Gly Thr Thr Ile Asp Val Ser Ala Glu Ser Ser Ser Val Leu Cys Thr
                405                 410                 415

Asp Gly Glu Asn Thr Val Ala Ser Asp Ala Thr Val Thr Ala Leu
        420                 425                 430

<210> SEQ ID NO 17
<211> LENGTH: 1140
<212> TYPE: DNA
<213> ORGANISM: Rhesus cytomegalovirus
<220> FEATURE:
<223> OTHER INFORMATION: rhesus monkey cytomegalovirus (rhCMV) UL78
      homolog (rhUL78)
<221> NAME/KEY: CDS
<222> LOCATION: (1)..(1140)
<223> OTHER INFORMATION: rhUL78

<400> SEQUENCE: 17
atgattacgg agcgcgtcct cgcaggcatc ctcgcgggca tgacggccgc ggggagtttg      60
gtcattctcc tcgcggttgt tatgtggttg aacatgttag atcgcgctgg catgccaatg    120
gccgttgggc attacacagg gaacctggtg ttgactcagg tcatctgtat cttctccatg    180
ctggcgtcta aaattgttgg catgacgagt gcggccaaca tgggcttctg cggcatcgtg    240 gttttctgg aagacactgg cctctatgtc acctcgctgc tcttcatgtt tatgatcctg    300
gatcgcatgg cggcttttct taacgggcgt cttttctgga ggcagcagac gacgaagcag    360
aatctgagta caagcgtgta cattattctg ttttgctggg tgttgggaat ggccgcggct    420
gttcccagcg cggctgtggc tgcacccaat tccaggtggg aacgctgcga aattccagtg    480
tcatatgccg caatcgacat gattgtgaag ctctggtttg tgctgttggc acccgtcgtg    540
ctgattatgg ctgtgatcat tcaatcttcc tatcatcgtg atcgggagag gatctggtac    600
tatgccagac gtgtgttcat gttctacacg gcctgctttg tcatgatggt gccttattac    660
ttcgtcagag tcatgctgag cgactttgct tggttgata taaaaacaaa acggcgaac    720 agcgacggtt gtgattcgac atttcttgat tatctgaaca tgttcactca cgtgatttac    780
agttttaagt tggtggtgtt tgctttgttc attgtcctgt tttgctccat aaacccgatg    840
gaaacgctgg aagaatgctt ggagagggcc gatgctgaga ggcaaagtcg gtcagaagca    900 tcccaggtg aaaggaggct gccaatcaac acatgctgta taagttgat tgaattgata    960 aagcagtatg taagcactct ctctaaagcc acgagggaca attctggcga aagggccaat   1020
ttgccagaga atgctgaaga tattggaaca actggcagtg atcagctacc gactgaggtc   1080
accgtgaccc caattcatc ggctgtgttt agcactggag aacggtgtc tccagtctaa   1140
```

```
<210> SEQ ID NO 18
<211> LENGTH: 379
<212> TYPE: PRT
<213> ORGANISM: Rhesus cytomegalovirus
<220> FEATURE:
<223> OTHER INFORMATION: rhesus monkey cytomegalovirus (rhCMV) UL78
      homolog (rhUL78)

<400> SEQUENCE: 18

Met Ile Thr Glu Arg Val Leu Ala Gly Ile Leu Ala Gly Met Thr Ala
 1               5                  10                  15

Ala Gly Ser Leu Val Ile Leu Leu Ala Val Val Met Trp Leu Asn Met
             20                  25                  30

Leu Asp Arg Ala Gly Met Pro Met Ala Val Gly His Tyr Thr Gly Asn
         35                  40                  45

Leu Val Leu Thr Gln Val Ile Cys Ile Phe Ser Met Leu Ala Ser Lys
     50                  55                  60

Ile Val Gly Met Thr Ser Ala Ala Asn Met Gly Phe Cys Gly Ile Val
 65                  70                  75                  80

Val Phe Leu Glu Asp Thr Gly Leu Tyr Val Thr Ser Leu Leu Phe Met
                 85                  90                  95

Phe Met Ile Leu Asp Arg Met Ala Ala Phe Leu Asn Gly Arg Leu Phe
            100                 105                 110

Trp Arg Gln Gln Thr Thr Lys Gln Asn Leu Ser Thr Ser Val Tyr Ile
        115                 120                 125

Ile Leu Phe Cys Trp Val Leu Gly Met Ala Ala Val Pro Ser Ala
    130                 135                 140

Ala Val Ala Ala Pro Asn Ser Arg Trp Glu Arg Cys Glu Ile Pro Val
145                 150                 155                 160

Ser Tyr Ala Ala Ile Asp Met Ile Val Lys Leu Trp Phe Val Leu Leu
                165                 170                 175

Ala Pro Val Val Leu Ile Met Ala Val Ile Ile Gln Ser Ser Tyr His
            180                 185                 190

Arg Asp Arg Glu Arg Ile Trp Tyr Tyr Ala Arg Arg Val Phe Met Phe
        195                 200                 205

Tyr Thr Ala Cys Phe Val Met Met Val Pro Tyr Tyr Phe Val Arg Val
    210                 215                 220

Met Leu Ser Asp Phe Ala Leu Val Asp Ile Lys Thr Lys Thr Ala Asn
225                 230                 235                 240

Ser Asp Gly Cys Asp Ser Thr Phe Leu Asp Tyr Leu Asn Met Phe Thr
                245                 250                 255

His Val Ile Tyr Ser Phe Lys Leu Val Val Phe Ala Leu Phe Ile Val
            260                 265                 270

Leu Phe Cys Ser Ile Asn Pro Met Glu Thr Leu Glu Glu Cys Leu Glu
        275                 280                 285

Arg Ala Asp Ala Glu Arg Gln Ser Arg Ser Glu Ala Ser Gln Gly Glu
    290                 295                 300

Arg Arg Leu Pro Ile Asn Thr Cys Cys Ile Lys Leu Ile Glu Leu Ile
305                 310                 315                 320

Lys Gln Tyr Val Ser Thr Leu Ser Lys Ala Thr Arg Asp Asn Ser Gly
                325                 330                 335

Glu Arg Ala Asn Leu Pro Glu Asn Ala Glu Asp Ile Gly Thr Thr Gly
            340                 345                 350

Ser Asp Gln Leu Pro Thr Glu Val Thr Val Thr Pro Asn Ser Ser Ala
        355                 360                 365
```

```
Val Phe Ser Thr Gly Gly Thr Val Ser Pro Val
    370                 375
```

<210> SEQ ID NO 19
<211> LENGTH: 1173
<212> TYPE: DNA
<213> ORGANISM: Human cytomegalovirus
<220> FEATURE:
<223> OTHER INFORMATION: human cytomegalovirus (HCMV) AD169 strain
      open reading frame UL33
<221> NAME/KEY: CDS
<222> LOCATION: (1)..(1173)
<223> OTHER INFORMATION: HCMV AD169 UL33

<400> SEQUENCE: 19

```
atgacagggc cgctattcgc cattcgaacc accgaagccg tactcaacac attcatcatc    60
ttcgtgggcg gtccacttaa cgccatagtg ttgatcacgc agctgctcac gaatcgcgtg   120
cttggctatt cgacgcccac catttacatg accaacctct actctactaa ttttctcacg   180
cttactgtgc taccctttat cgtactcagc aaccagtggc tgttgccggc cggcgtggcc   240
tcgtgtaaat ttctatcggt gatctactac tcaagctgca cagtgggctt tgccaccgta   300
gctctgatcg ccgccgatcg ttatcgcgtc cttcataaac gaacatacgc acgccaatca   360
taccgttcaa cctatatgat tttgctattg acatggctcg ctggactaat tttttccgtg   420
cccgcagctg tttacaccac ggtggtgatg catcacgatg ccaacgatac caataatact   480
aatgggcacg ccacctgtgt actgtacttc gtagctgaag aagtgcacac agtgctgctt   540
tcgtggaaag tgctgctgac gatggtatgg ggtgccgcac ccgtgataat gatgacgtgg   600
ttctacgcat tcttctactc aaccgtacag cgcacgtcac agaaacaaag gagtcgtacc   660
ttaacctttg ttagcgtgct actcatctcc ttcgtggcgc tacaaactcc ctacgtctct   720
ctcatgatct tcaacagtta tgccacaacc gcctggccca tgcagtgtga acacctcaca   780
ctgcgacgca ccattggcac gctggcgcgt gtggtgcccc acctacactg cctcattaat   840
cccatcctgt acgcgctgct gggtcatgat tttctgcaac gcatgcggca gtgtttccgc   900
ggtcagttgc tggaccgccg cgctttcctg agatcgcagc agaatcagcg agctacagcg   960
gagacaaatc tagcggctgg caacaattca caatcagtgg ctacgtcatt agacaccaat  1020
agcaaaaact acaatcagca cgccaaacgc agcgtgtctt tcaattttcc cagcggtacg  1080
tggaaaggcg gccagaaaac cgcgtccaac gacacatcca caaaaatccc ccatcgactc  1140
tcacaatcgc atcataacct cagcggggta tga                               1173
```

<210> SEQ ID NO 20
<211> LENGTH: 390
<212> TYPE: PRT
<213> ORGANISM: Human cytomegalovirus
<220> FEATURE:
<223> OTHER INFORMATION: human cytomegalovirus (HCMV) AD169 strain
      open reading frame UL33

<400> SEQUENCE: 20

```
Met Thr Gly Pro Leu Phe Ala Ile Arg Thr Thr Glu Ala Val Leu Asn
  1               5                  10                  15

Thr Phe Ile Ile Phe Val Gly Gly Pro Leu Asn Ala Ile Val Leu Ile
                 20                  25                  30

Thr Gln Leu Leu Thr Asn Arg Val Leu Gly Tyr Ser Thr Pro Thr Ile
             35                  40                  45

Tyr Met Thr Asn Leu Tyr Ser Thr Asn Phe Leu Thr Leu Thr Val Leu
```

-continued

```
                50                  55                  60
Pro Phe Ile Val Leu Ser Asn Gln Trp Leu Pro Ala Gly Val Ala
 65                  70                  75                  80

Ser Cys Lys Phe Leu Ser Val Ile Tyr Tyr Ser Cys Thr Val Gly
                 85                  90                  95

Phe Ala Thr Val Ala Leu Ile Ala Ala Asp Arg Tyr Arg Val Leu His
                100                 105                 110

Lys Arg Thr Tyr Ala Arg Gln Ser Tyr Arg Ser Thr Tyr Met Ile Leu
                115                 120                 125

Leu Leu Thr Trp Leu Ala Gly Leu Ile Phe Ser Val Pro Ala Ala Val
130                 135                 140

Tyr Thr Thr Val Val Met His His Asp Ala Asn Asp Thr Asn Asn Thr
145                 150                 155                 160

Asn Gly His Ala Thr Cys Val Leu Tyr Phe Val Ala Glu Glu Val His
                165                 170                 175

Thr Val Leu Leu Ser Trp Lys Val Leu Leu Thr Met Val Trp Gly Ala
                180                 185                 190

Ala Pro Val Ile Met Met Thr Trp Phe Tyr Ala Phe Phe Tyr Ser Thr
                195                 200                 205

Val Gln Arg Thr Ser Gln Lys Gln Arg Ser Arg Thr Leu Thr Phe Val
210                 215                 220

Ser Val Leu Leu Ile Ser Phe Val Ala Leu Gln Thr Pro Tyr Val Ser
225                 230                 235                 240

Leu Met Ile Phe Asn Ser Tyr Ala Thr Thr Ala Trp Pro Met Gln Cys
                245                 250                 255

Glu His Leu Thr Leu Arg Arg Thr Ile Gly Thr Leu Ala Arg Val Val
                260                 265                 270

Pro His Leu His Cys Leu Ile Asn Pro Ile Leu Tyr Ala Leu Leu Gly
                275                 280                 285

His Asp Phe Leu Gln Arg Met Arg Gln Cys Phe Arg Gly Gln Leu Leu
                290                 295                 300

Asp Arg Arg Ala Phe Leu Arg Ser Gln Gln Asn Gln Arg Ala Thr Ala
305                 310                 315                 320

Glu Thr Asn Leu Ala Ala Gly Asn Asn Ser Gln Ser Val Ala Thr Ser
                325                 330                 335

Leu Asp Thr Asn Ser Lys Asn Tyr Asn Gln His Ala Lys Arg Ser Val
                340                 345                 350

Ser Phe Asn Phe Pro Ser Gly Thr Trp Lys Gly Gln Lys Thr Ala
                355                 360                 365

Ser Asn Asp Thr Ser Thr Lys Ile Pro His Arg Leu Ser Gln Ser His
370                 375                 380

His Asn Leu Ser Gly Val
385                 390
```

<210> SEQ ID NO 21
<211> LENGTH: 1239
<212> TYPE: DNA
<213> ORGANISM: Human cytomegalovirus
<220> FEATURE:
<223> OTHER INFORMATION: human cytomegalovirus (HCMV) AD169 strain
      open reading frame UL33 splice variant (UL33 spliced)
<221> NAME/KEY: CDS
<222> LOCATION: (1)..(1239)
<223> OTHER INFORMATION: HCMV AD169 UL33 spliced

<400> SEQUENCE: 21

-continued

```
atggacacca tcatccacaa ctcgacccgc aacaacactc ctccgcacat caatgacact    60
tgcaacatga cagggccgct attcgccatt cgaaccaccg aagccgtact caacacattc   120
atcatcttcg tgggcggtcc acttaacgcc atagtgttga tcacgcagct gctcacgaat   180
cgcgtgcttg gctattcgac gcccaccatt tacatgacca acctctactc tactaatttt   240
ctcacgctta ctgtgctacc ctttatcgta ctcagcaacc agtggctgtt gccggccggc   300
gtggcctcgt gtaaatttct atcggtgatc tactactcaa gctgcacagt gggcttttgcc  360 accgtagctc tgatcgccgc cgatcgttat cgcgtccttc ataaacgaac atacgcacgc   420
caatcatacc gttcaaccta tatgattttg ctattgacat ggctcgctgg actaattttt   480
tccgtgcccg cagctgttta caccacggtg gtgatgcatc acgatgccaa cgataccaat   540
aatactaatg ggcacgccac ctgtgtactg tacttcgtag ctgaagaagt gcacacagtg   600
ctgctttcgt ggaaagtgct gctgacgatg gtatggggtg ccgcacccgt gataatgatg   660
acgtggttct acgcattctt ctactcaacc gtacagcgca cgtcacagaa acaaaggagt   720
cgtaccttaa cctttgttag cgtgctactc atctccttcg tggcgctaca aactccctac   780
gtctctctca tgatcttcaa cagttatgcc acaaccgcct ggcccatgca gtgtgaacac   840
ctcacactgc gacgcaccat tggcacgctg gcgcgtgtgg tgccccacct acactgcctc   900
attaatccca tcctgtacgc gctgctgggt catgattttc tgcaacgcat gcggcagtgt   960
ttccgcggtc agttgctgga ccgccgcgct ttcctgagat cgcagcagaa tcagcgagct  1020
acagcggaga caaatctagc ggctggcaac aattcacaat cagtggctac gtcattagac  1080
accaatagca aaaactacaa tcagcacgcc aaacgcagcg tgtctttcaa ttttcccagc  1140
ggtacgtgga aggcggcca gaaaaccgcg tccaacgaca catccacaaa atcccccat    1200 cgactctcac aatcgcatca taacctcagc ggggtatga                         1239
```

<210> SEQ ID NO 22
<211> LENGTH: 412
<212> TYPE: PRT
<213> ORGANISM: Human cytomegalovirus
<220> FEATURE:
<223> OTHER INFORMATION: human cytomegalovirus (HCMV) AD169 strain
      open reading frame UL33 splice variant (UL33 spliced)

<400> SEQUENCE: 22

```
Met Asp Thr Ile Ile His Asn Ser Thr Arg Asn Asn Thr Pro Pro His
  1               5                  10                  15

Ile Asn Asp Thr Cys Asn Met Thr Gly Pro Leu Phe Ala Ile Arg Thr
             20                  25                  30

Thr Glu Ala Val Leu Asn Thr Phe Ile Ile Phe Val Gly Gly Pro Leu
         35                  40                  45

Asn Ala Ile Val Leu Ile Thr Gln Leu Leu Thr Asn Arg Val Leu Gly
     50                  55                  60

Tyr Ser Thr Pro Thr Ile Tyr Met Thr Asn Leu Tyr Ser Thr Asn Phe
 65                  70                  75                  80

Leu Thr Leu Thr Val Leu Pro Phe Ile Val Leu Ser Asn Gln Trp Leu
                 85                  90                  95

Leu Pro Ala Gly Val Ala Ser Cys Lys Phe Leu Ser Val Ile Tyr Tyr
            100                 105                 110

Ser Ser Cys Thr Val Gly Phe Ala Thr Val Ala Leu Ile Ala Ala Asp
        115                 120                 125

Arg Tyr Arg Val Leu His Lys Arg Thr Tyr Ala Arg Gln Ser Tyr Arg
    130                 135                 140
```

```
Ser Thr Tyr Met Ile Leu Leu Thr Trp Leu Ala Gly Leu Ile Phe
145                 150                 155                 160

Ser Val Pro Ala Ala Val Tyr Thr Thr Val Met His His Asp Ala
            165                 170                 175

Asn Asp Thr Asn Asn Thr Asn Gly His Ala Thr Cys Val Leu Tyr Phe
        180                 185                 190

Val Ala Glu Glu Val His Thr Val Leu Leu Ser Trp Lys Val Leu Leu
        195                 200                 205

Thr Met Val Trp Gly Ala Ala Pro Val Ile Met Met Thr Trp Phe Tyr
210                 215                 220

Ala Phe Phe Tyr Ser Thr Val Gln Arg Thr Ser Gln Lys Gln Arg Ser
225                 230                 235                 240

Arg Thr Leu Thr Phe Val Ser Val Leu Leu Ile Ser Phe Val Ala Leu
            245                 250                 255

Gln Thr Pro Tyr Val Ser Leu Met Ile Phe Asn Ser Tyr Ala Thr Thr
            260                 265                 270

Ala Trp Pro Met Gln Cys Glu His Leu Thr Leu Arg Arg Thr Ile Gly
275                 280                 285

Thr Leu Ala Arg Val Val Pro His Leu His Cys Leu Ile Asn Pro Ile
290                 295                 300

Leu Tyr Ala Leu Leu Gly His Asp Phe Leu Gln Arg Met Arg Gln Cys
305                 310                 315                 320

Phe Arg Gly Gln Leu Leu Asp Arg Arg Ala Phe Leu Arg Ser Gln Gln
            325                 330                 335

Asn Gln Arg Ala Thr Ala Glu Thr Asn Leu Ala Ala Gly Asn Asn Ser
            340                 345                 350

Gln Ser Val Ala Thr Ser Leu Asp Thr Asn Ser Lys Asn Tyr Asn Gln
            355                 360                 365

His Ala Lys Arg Ser Val Ser Phe Asn Phe Pro Ser Gly Thr Trp Lys
        370                 375                 380

Gly Gly Gln Lys Thr Ala Ser Asn Asp Thr Ser Thr Lys Ile Pro His
385                 390                 395                 400

Arg Leu Ser Gln Ser His His Asn Leu Ser Gly Val
                405                 410
```

<210> SEQ ID NO 23
<211> LENGTH: 990
<212> TYPE: DNA
<213> ORGANISM: Rhesus cytomegalovirus
<220> FEATURE:
<223> OTHER INFORMATION: rhesus monkey cytomegalovirus (rhCMV) UL33 homolog (rhUL33)
<221> NAME/KEY: CDS
<222> LOCATION: (1)..(990)
<223> OTHER INFORMATION: rhUL33

<400> SEQUENCE: 23

```
atgaccaatc tttactctgc caatttctc accttgatag tacttccttt tatcgtttta      60
agcaatcaac acctttacc tgccagtgca gtaacctgta aatttctctc cctgttgtac     120
tactctagct gcagcgtagg ttttgctaca gtggcactga tagcggccga ccgataccga     180
gtgattcatc gccgaactca agctcgccaa tcctaccgta acacatatat gatagtaggc     240
ttaacgtggc tcattggctt gatctgcgct acccccgggg gggtctacac aaccattgta     300
gctcaccgcg atggggaaag tgatgctcaa agacacaata cttgcattat gcactttgcg     360
tatgatgaag tttacgtcct catggtctgg aaacttctca tcgtttagt ctggggcata     420
```

```
gtgccagttg tcatgatgag ctggttttac gcgttttttt acaatactgt acaaagaaca    480
gccaaaaaac aacaacgtac gttgaaattc gtaaaggtat tactcctgtc attcatcatc    540
atccaaactc cctatgtgtc aatcatgatt tttaacacgt atgccaccgt aggatggccg    600
atggaatgcg ccgatctaac tagacgccga gtcatcaaca cgttttcccg tctcgtcccc    660
aatctacatt gcatggtcaa ccccatcctc tacgctctca tgggaaatga ctttgtgtct    720
aaagtgggcc aatgctttcg gggggaactc acgaaccgtc gaacttttct gcgttccaag    780
caacaagccc gcaactcgga cgatgtaccg acaattgtca gtcaacaacc cgccacaccc    840
accatcgtca ataagcccga aaaaaacccg cacgtaaaac gcggtgtatc tttcagcgtc    900
agcgcatctt ccgaactcgc agcggccaaa aaagccaaag acaaagccaa gcggctttcc    960
atgtcccacc aaaacctacg tctgacgtga                                    990
```

<210> SEQ ID NO 24
<211> LENGTH: 329
<212> TYPE: PRT
<213> ORGANISM: Rhesus cytomegalovirus
<220> FEATURE:
<223> OTHER INFORMATION: rhesus monkey cytomegalovirus (rhCMV) UL33
      homolog (rhUL33)

<400> SEQUENCE: 24

```
Met Thr Asn Leu Tyr Ser Ala Asn Phe Leu Thr Leu Ile Val Leu Pro
  1               5                  10                  15

Phe Ile Val Leu Ser Asn Gln His Leu Leu Pro Ala Ser Ala Val Thr
             20                  25                  30

Cys Lys Phe Leu Ser Leu Leu Tyr Tyr Ser Ser Cys Ser Val Gly Phe
         35                  40                  45

Ala Thr Val Ala Leu Ile Ala Ala Asp Arg Tyr Arg Val Ile His Arg
     50                  55                  60

Arg Thr Gln Ala Arg Gln Ser Tyr Arg Asn Thr Tyr Met Ile Val Gly
 65                  70                  75                  80

Leu Thr Trp Leu Ile Gly Leu Ile Cys Ala Thr Pro Gly Gly Val Tyr
                 85                  90                  95

Thr Thr Ile Val Ala His Arg Asp Gly Glu Ser Asp Ala Gln Arg His
            100                 105                 110

Asn Thr Cys Ile Met His Phe Ala Tyr Asp Glu Val Tyr Val Leu Met
        115                 120                 125

Val Trp Lys Leu Leu Ile Val Leu Val Trp Gly Ile Val Pro Val Val
    130                 135                 140

Met Met Ser Trp Phe Tyr Ala Phe Phe Tyr Asn Thr Val Gln Arg Thr
145                 150                 155                 160

Ala Lys Lys Gln Gln Arg Thr Leu Lys Phe Val Lys Val Leu Leu Leu
                165                 170                 175

Ser Phe Ile Ile Ile Gln Thr Pro Tyr Val Ser Ile Met Ile Phe Asn
            180                 185                 190

Thr Tyr Ala Thr Val Gly Trp Pro Met Glu Cys Ala Asp Leu Thr Arg
        195                 200                 205

Arg Arg Val Ile Asn Thr Phe Ser Arg Leu Val Pro Asn Leu His Cys
    210                 215                 220

Met Val Asn Pro Ile Leu Tyr Ala Leu Met Gly Asn Asp Phe Val Ser
225                 230                 235                 240

Lys Val Gly Gln Cys Phe Arg Gly Glu Leu Thr Asn Arg Arg Thr Phe
                245                 250                 255
```

Leu Arg Ser Lys Gln Gln Ala Arg Asn Ser Asp Asp Val Pro Thr Ile
            260                 265                 270

Val Ser Gln Gln Pro Ala Thr Pro Thr Ile Val Asn Lys Pro Glu Lys
        275                 280                 285

Asn Pro His Val Lys Arg Gly Val Ser Phe Ser Val Ser Ala Ser Ser
    290                 295                 300

Glu Leu Ala Ala Ala Lys Lys Ala Lys Asp Lys Ala Lys Arg Leu Ser
305                 310                 315                 320

Met Ser His Gln Asn Leu Arg Leu Thr
                325

<210> SEQ ID NO 25
<211> LENGTH: 1328
<212> TYPE: DNA
<213> ORGANISM: Rhesus cytomegalovirus
<220> FEATURE:
<223> OTHER INFORMATION: rhesus monkey cytomegalovirus (rhCMV) UL33
      splice variant homolog (rhUL33 spliced)
<221> NAME/KEY: CDS
<222> LOCATION: (1)..(1328)
<223> OTHER INFORMATION: rhUL33 spliced

<400> SEQUENCE: 25

| | | | | | |
|---|---|---|---|---|---|
| atggcagtca | ctttacgagg | cggcagcccg | ataaacttta | aactcatgat | tgtcagccac | 60 |
| agaaaccgga | aatttcacga | gatacggctg | tttcagcgtt | ctgctatccg | tccaggcggg | 120 |
| ttatggaaac | cattcttcac | aaccgaacga | gtgaaactaa | ttccattttg | cacatcaaca | 180 |
| ccacctgcaa | tgtgaccgac | tcactgtacg | ccgccaaact | aggcgaagcc | ctcgtgaaca | 240 |
| gcgcgctagc | tttattcggt | accccctca | acgccatcgt | cctcgtcaca | cagctattgg | 300 |
| ccaaccgagt | tcatggatac | tccaccccga | ttatctacat | gaccaatctt | tactctgcca | 360 |
| attttctcac | cttgatagta | cttccttta | tcgttttaag | caatcaacac | cttttacctg | 420 |
| ccagtgcagt | aacctgtaaa | tttctctccc | tgttgtacta | ctctagctgc | agcgtaggtt | 480 |
| ttgctacagt | ggcactgata | gcggccgacc | gataccgagt | gattcatcgc | cgaactcaag | 540 |
| ctcgccaatc | ctaccgtaac | acatatatga | tagtaggctt | aacgtggctc | attggcttga | 600 |
| tctgcgctac | ccccgggggg | gtctacacaa | ccattgtagc | tcaccgcgat | ggggaaagtg | 660 |
| atgctcaaag | acacaatact | tgcattatgc | actttgcgta | tgatgaagtt | tacgtcctca | 720 |
| tggtctggaa | acttctcatc | gtttagtct | ggggcatagt | gccagttgtc | atgatgagct | 780 |
| ggttttacgc | gttttttac | aatactgtac | aaagaacagc | caaaaacaa | caacgtacgt | 840 |
| tgaaattcgt | aaaggtatta | ctcctgtcat | tcatcatcat | ccaaactccc | tatgtgtcaa | 900 |
| tcatgatttt | taacacgtat | gccaccgtag | gatggccgat | ggaatgcgcc | gatctaacta | 960 |
| gacgccgagt | catcaacacg | ttttcccgtc | tcgtccccaa | tctacattgc | atggtcaacc | 1020 |
| ccatcctcta | cgctctcatg | ggaaatgact | ttgtgtctaa | agtgggccaa | tgctttcggg | 1080 |
| gggaactcac | gaaccgtcga | acttttctgc | gttccaagca | acaagcccgc | aactcggacg | 1140 |
| atgtaccgac | aattgtcagt | caacaacccg | ccacacccac | catcgtcaat | aagcccgaaa | 1200 |
| aaaacccgca | cgtaaaacgc | ggtgtatctt | tcagcgtcag | cgcatcttcc | gaactcgcag | 1260 |
| cggccaaaaa | agccaaagac | aaagccaagc | ggctttccat | gtcccaccaa | aacctacgtc | 1320 |
| tgacgtga | | | | | | 1328 |

<210> SEQ ID NO 26
<211> LENGTH: 441

<210> 26
<211> 390
<212> TYPE: PRT
<213> ORGANISM: Rhesus cytomegalovirus
<220> FEATURE:
<223> OTHER INFORMATION: rhesus monkey cytomegalovirus (rhCMV) UL33 splice variant homolog (rhUL33 spliced)

<400> SEQUENCE: 26

```
Met Ala Val Thr Leu Arg Gly Gly Ser Pro Ile Asn Phe Lys Leu Met
 1               5                  10                  15

Ile Val Ser His Arg Asn Arg Lys Phe His Glu Ile Arg Leu Phe Gln
             20                  25                  30

Arg Ser Ala Ile Arg Pro Gly Gly Leu Trp Lys Pro Phe Phe Thr Thr
         35                  40                  45

Glu Arg Glu Thr Asn Ser Ile Leu His Ile Asn Thr Thr Cys Asn Val
     50                  55                  60

Thr Asp Ser Leu Tyr Ala Ala Lys Leu Gly Glu Ala Leu Val Asn Ser
 65                  70                  75                  80

Ala Leu Ala Leu Phe Gly Thr Pro Leu Asn Ala Ile Val Leu Val Thr
                 85                  90                  95

Gln Leu Leu Ala Asn Arg Val His Gly Tyr Ser Thr Pro Ile Ile Tyr
            100                 105                 110

Met Thr Asn Leu Tyr Ser Ala Asn Phe Leu Thr Leu Ile Val Leu Pro
        115                 120                 125

Phe Ile Val Leu Ser Asn Gln His Leu Leu Pro Ala Ser Ala Val Thr
130                 135                 140

Cys Lys Phe Leu Ser Leu Leu Tyr Tyr Ser Ser Cys Ser Val Gly Phe
145                 150                 155                 160

Ala Thr Val Ala Leu Ile Ala Ala Asp Arg Tyr Arg Val Ile His Arg
                165                 170                 175

Arg Thr Gln Ala Arg Gln Ser Tyr Arg Asn Thr Tyr Met Ile Val Gly
            180                 185                 190

Leu Thr Trp Leu Ile Gly Leu Ile Cys Ala Thr Pro Gly Gly Val Tyr
        195                 200                 205

Thr Thr Ile Val Ala His Arg Asp Gly Glu Ser Asp Ala Gln Arg His
210                 215                 220

Asn Thr Cys Ile Met His Phe Ala Tyr Asp Glu Val Tyr Val Leu Met
225                 230                 235                 240

Val Trp Lys Leu Leu Ile Val Leu Val Trp Gly Ile Val Pro Val Val
                245                 250                 255

Met Met Ser Trp Phe Tyr Ala Phe Phe Tyr Asn Thr Val Gln Arg Thr
            260                 265                 270

Ala Lys Lys Gln Gln Arg Thr Leu Lys Phe Val Lys Val Leu Leu Leu
        275                 280                 285

Ser Phe Ile Ile Ile Gln Thr Pro Tyr Val Ser Ile Met Ile Phe Asn
290                 295                 300

Thr Tyr Ala Thr Val Gly Trp Pro Met Glu Cys Ala Asp Leu Thr Arg
305                 310                 315                 320

Arg Arg Val Ile Asn Thr Phe Ser Arg Leu Val Pro Asn Leu His Cys
                325                 330                 335

Met Val Asn Pro Ile Leu Tyr Ala Leu Met Gly Asn Asp Phe Val Ser
            340                 345                 350

Lys Val Gly Gln Cys Phe Arg Gly Glu Leu Thr Asn Arg Arg Thr Phe
        355                 360                 365

Leu Arg Ser Lys Gln Gln Ala Arg Asn Ser Asp Asp Val Pro Thr Ile
370                 375                 380
```

```
Val Ser Gln Gln Pro Ala Thr Pro Thr Ile Val Asn Lys Pro Glu Lys
385                 390                 395                 400

Asn Pro His Val Lys Arg Gly Val Ser Phe Ser Val Ser Ala Ser Ser
                405                 410                 415

Glu Leu Ala Ala Ala Lys Lys Ala Lys Asp Lys Ala Lys Arg Leu Ser
            420                 425                 430

Met Ser His Gln Asn Leu Arg Leu Thr
            435                 440

<210> SEQ ID NO 27
<211> LENGTH: 2100
<212> TYPE: DNA
<213> ORGANISM: Rhesus cytomegalovirus
<220> FEATURE:
<223> OTHER INFORMATION: rhesus monkey cytomegalovirus (rhCMV) UL33
      splice variant homolog (rhUL33 spliced) nucleotide sequence
      segment that extends 1000 nucleotides upstream and downstream
      of the rhUL33 reading frame
<221> NAME/KEY: exon
<222> LOCATION: (603)..(752)
<223> OTHER INFORMATION: exon 1
<221> NAME/KEY: intron
<222> LOCATION: (753)..(830)
<221> NAME/KEY: exon
<222> LOCATION: (831)..(2006)
<223> OTHER INFORMATION: exon 2
<221> NAME/KEY: misc_feature
<222> LOCATION: (1017)..(2006)
<223> OTHER INFORMATION: unspliced gene

<400> SEQUENCE: 27
cggccaagat gtcccaagag gttctgacat gaacaatcac ttttccgaga tagatgagtt     60
tgttagtggc atttaccaga gaactattgg agtgacgctc aagatgaagc ttcactggcc    120
gtatttcgaa catattgtta gatatagcta gtaaagaatc ttctaaagcc atgacgtctt    180
tctgacgaag ttgaataaat tctatctcac cagtacccaa aggctgacac tcagacaact    240
ttgccaaggc cgttgcaccc accatggcat tctgaatcac agtaacatcc gtccgagaat    300
cgtcaccaaa aacggtggcc tccaaagttc gcaggtgagg ccgagccttt actggatctc    360
ggaagggata catgtgtgct cgccgagtga cagcattagc attaacctca aactcatcta    420
aaagcgatga taaatcagga atatgatagc gcaattctcg atagtaggcc aaccagagga    480
ctaattggtt gaacagacag ctccgtctgt gcaaaaactt ttcgccgcat tttctgagaa    540
ttttaggatg ctgctctaaa tctacgttct ctttagtcgg cagggtcttt aaaaagttag    600
tgatggcagt cactttacga ggcggcagcc cgataaactt taaactcatg attgtcagcc    660
acagaaaccg gaaatttcac gagatacggc tgtttcagcg ttctgctatc cgtccaggcg    720
ggttatggaa accattcttc acaaccgaac ggtgagtgac atttaagaca gtttaatagc    780
caacactcgt aacgtctcgg aagctgataa gtttcgtttt tccacagagt gaaactaatt    840
ccattttgca catcaacacc acctgcaatg tgaccgactc actgtacgcc gccaaactag    900
gcgaagccct cgtgaacagc gcgctagctt tattcggtac cccctcaac gccatcgtcc      960 tcgtcacaca gctattggcc aaccgagttc atggatactc caccccgatt atctacatga   1020
ccaatcttta ctctgccaat tttctcacct tgatagtact ccttttatc gttttaagca    1080 atcaacacct tttacctgcc agtgcagtaa cctgtaaatt tctctccctg ttgtactact   1140
ctagctgcag cgtaggtttt gctacagtgg cactgatagc ggccgaccga taccgagtga   1200
ttcatcgccg aactcaagct cgccaatcct accgtaacac atatatgata gtaggcttaa   1260
```

```
cgtggctcat tggcttgatc tgcgctaccc ccggggggt ctacacaacc attgtagctc    1320
accgcgatgg ggaaagtgat gctcaaagac acaatacttg cattatgcac tttgcgtatg    1380
atgaagttta cgtcctcatg gtctggaaac ttctcatcgt tttagtctgg ggcatagtgc    1440
cagttgtcat gatgagctgg ttttacgcgt tttttttacaa tactgtacaa agaacagcca    1500
aaaaacaaca acgtacgttg aaattcgtaa aggtattact cctgtcattc atcatcatcc    1560
aaactcccta tgtgtcaatc atgattttta acacgtatgc caccgtagga tggccgatgg    1620
aatgcgccga tctaactaga cgccgagtca tcaacacgtt ttcccgtctc gtccccaatc    1680
tacattgcat ggtcaaccc atcctctacg ctctcatggg aaatgacttt gtgtctaaag    1740
tgggccaatg ctttcggggg gaactcacga accgtcgaac ttttctgcgt tccaagcaac    1800
aagcccgcaa ctcggacgat gtaccgacaa ttgtcagtca acaacccgcc acacccacca    1860
tcgtcaataa gcccgaaaaa aacccgcacg taaaacgcgg tgtatctttc agcgtcagcg    1920
catcttccga actcgcagcg gccaaaaaag ccaaagacaa agccaagcgg ctttccatgt    1980
cccaccaaaa cctacgtctg acgtgaattt cctagaggc tgcctccacg ggtttacata    2040
catatctcgg tacttgctac acttgatcac tttactgcgg acaccacggc caatcgcatc    2100
```

```
<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence:rhUS28
      homolog rhUS28.1 amplification primer sequence (upper strand)

<400> SEQUENCE: 28
tatgaataac acatcttgca acttc                                            25

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:rhUS28
      homolog rhUS28.1 amplification primer sequence (lower strand)

<400> SEQUENCE: 29
cacacagacc acatgtac                                                    18

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:rhUS28
      homolog rhUS28.2 amplification primer sequence (upper strand)

<400> SEQUENCE: 30
attcaacatg accaacgccg g                                                21

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence:rhUS28
      homolog rhUS28.2 amplification primer sequence (lower strand)

<400> SEQUENCE: 31
gcatttccgt ggattcg                                                     17
```

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence:rhUS28
      homolog rhUS28.3 amplification primer sequence (upper strand)

<400> SEQUENCE: 32
catgaccaac actaac                                                    16

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence:rhUS28
      homolog rhUS28.3 amplification primer sequence (lower strand)

<400> SEQUENCE: 33
gagtcttttg tgagcc                                                    16

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence:rhUS28
      homolog rhUS28.4 amplification primer sequence (upper strand)

<400> SEQUENCE: 34
tatgaattcg agccagcac                                                 19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence:rhUS28
      homolog rhUS28.4 amplification primer sequence (lower strand)

<400> SEQUENCE: 35
gtacgcgact aagacagag                                                 19

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:rhUS28
      homolog rhUS28.5 amplification primer sequence (upper strand)

<400> SEQUENCE: 36
aaagatgact accaccac                                                  18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:rhUS28
      homolog rhUS28.5 amplification primer sequence (lower strand)

<400> SEQUENCE: 37
ataacctagc acctcccc                                                  18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:rhUS28
      homolog rhUL78 amplification primer sequence (upper strand)

<400> SEQUENCE: 38
ctgaaaccat gattacgg                                                    18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:rhUS28
      homolog rhUL78 amplification primer sequence (lower strand)

<400> SEQUENCE: 39
cacgcagcac aagagcac                                                    18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence:rhUS28
      homolog rhUL33 amplification primer sequence (upper strand)

<400> SEQUENCE: 40
catgaccaat ctttactc                                                    18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence:rhUS28
      homolog rhUL33 amplification primer sequence (lower strand)

<400> SEQUENCE: 41
gtgtcgccac tcctaccc                                                    18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:rhUS28
      homolog rhUL33 splice amplification primer sequence
      (upper strand)

<400> SEQUENCE: 42
aagttagtga tggcagtc                                                    18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence:rhUS28
      homolog rhUL33 splice amplification primer sequence
      (lower strand)

<400> SEQUENCE: 43
gtatgtaaac ccgtggag                                                    18

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence:nested PCR
     CMV specific primer able to amplify the rhCMV immediate early 2
     gene

<400> SEQUENCE: 44
gccaatgcat cctctggatg tattgtga                                    28

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:nested PCR
     CMV specific primer able to amplify the rhCMV immediate early 2
     gene

<400> SEQUENCE: 45
tgcttgggga atctctgcac                                             20

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence:nested PCR
     CMV specific primer able to amplify the rhCMV immediate early 2
     gene

<400> SEQUENCE: 46
cccttcctga ctactaatgt ac                                          22

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:nested PCR
     CMV specific primer able to amplify the rhCMV immediate early 2
     gene

<400> SEQUENCE: 47
ttggggaatc tctgcacaag                                             20

<210> SEQ ID NO 48
<211> LENGTH: 354
<212> TYPE: PRT
<213> ORGANISM: Human cytomegalovirus
<220> FEATURE:
<223> OTHER INFORMATION: human cytomegalovirus (HCMV) AD169 strain
     open reading frame US28

<400> SEQUENCE: 48

Met Thr Pro Thr Thr Thr Thr Ala Glu Leu Thr Thr Glu Phe Asp Tyr
 1               5                  10                  15

Asp Glu Asp Ala Thr Pro Cys Val Phe Thr Asp Val Leu Asn Gln Ser
            20                  25                  30

Lys Pro Val Thr Leu Phe Leu Tyr Gly Val Val Phe Leu Phe Gly Ser
        35                  40                  45

Ile Gly Asn Phe Leu Val Ile Phe Thr Ile Thr Trp Arg Arg Arg Ile
    50                  55                  60

-continued

```
Gln Cys Ser Gly Asp Val Tyr Phe Ile Asn Leu Ala Ala Ala Asp Leu
 65                  70                  75                  80

Leu Phe Val Cys Thr Leu Pro Leu Trp Met Gln Tyr Leu Leu Asp His
             85                  90                  95

Asn Ser Leu Ala Ser Val Pro Cys Thr Leu Leu Thr Ala Cys Phe Tyr
            100                 105                 110

Val Ala Met Phe Ala Ser Leu Cys Phe Ile Thr Glu Ile Ala Leu Asp
            115                 120                 125

Arg Tyr Tyr Ala Ile Val Tyr Met Arg Tyr Arg Pro Val Lys Gln Ala
    130                 135                 140

Cys Leu Phe Ser Ile Phe Trp Trp Ile Phe Ala Val Ile Ile Ala Ile
145                 150                 155                 160

Pro His Phe Met Val Val Thr Lys Lys Asp Asn Gln Cys Met Thr Asp
                165                 170                 175

Tyr Asp Tyr Leu Glu Val Ser Tyr Pro Ile Ile Leu Asn Val Glu Leu
            180                 185                 190

Met Leu Gly Ala Phe Val Ile Pro Leu Ser Val Ile Ser Tyr Cys Tyr
        195                 200                 205

Tyr Arg Ile Ser Arg Ile Val Ala Val Ser Gln Ser Arg His Lys Gly
    210                 215                 220

Arg Ile Val Arg Val Leu Ile Ala Val Val Leu Val Phe Ile Ile Phe
225                 230                 235                 240

Trp Leu Pro Tyr His Leu Thr Leu Phe Val Asp Thr Leu Lys Leu Leu
                245                 250                 255

Lys Trp Ile Ser Ser Ser Cys Glu Phe Glu Arg Ser Leu Lys Arg Ala
            260                 265                 270

Leu Ile Leu Thr Glu Ser Leu Ala Phe Cys His Cys Cys Leu Asn Pro
            275                 280                 285

Leu Leu Tyr Val Phe Val Gly Thr Lys Phe Arg Gln Glu Leu His Cys
        290                 295                 300

Leu Leu Ala Glu Phe Arg Gln Arg Leu Phe Ser Arg Asp Val Ser Trp
305                 310                 315                 320

Tyr His Ser Met Ser Phe Ser Arg Arg Ser Ser Pro Ser Arg Arg Glu
                325                 330                 335

Thr Ser Ser Asp Thr Leu Ser Asp Glu Val Cys Arg Val Ser Gln Ile
            340                 345                 350

Ile Pro
```